(12) United States Patent
Kofoed et al.

(10) Patent No.: US 11,274,135 B2
(45) Date of Patent: Mar. 15, 2022

(54) DOUBLE-ACYLATED GLP-1 DERIVATIVES

(71) Applicant: Novo Nordisk A/S, Bagsvaerd (DK)

(72) Inventors: Jacob Kofoed, Vaerloese (DK); Patrick W. Garibay, Holte (DK)

(73) Assignee: Novo Nordisk A/S, Bagsvaerd (DK)

(*) Notice: Subject to any disclaimer, the term of this patent is extended or adjusted under 35 U.S.C. 154(b) by 0 days.

(21) Appl. No.: 14/399,086

(22) PCT Filed: May 2, 2013

(86) PCT No.: PCT/EP2013/059113
§ 371 (c)(1),
(2) Date: Nov. 5, 2014

(87) PCT Pub. No.: WO2013/167455
PCT Pub. Date: Nov. 14, 2013

(65) Prior Publication Data
US 2015/0152157 A1  Jun. 4, 2015

Related U.S. Application Data

(60) Provisional application No. 61/646,469, filed on May 14, 2012.

(30) Foreign Application Priority Data

May 8, 2012  (EP) .................................. 12167093

(51) Int. Cl.
C07K 14/605 (2006.01)
A61K 38/26 (2006.01)
A61K 38/00 (2006.01)

(52) U.S. Cl.
CPC ............ *C07K 14/605* (2013.01); *A61K 38/26* (2013.01); *A61K 38/00* (2013.01)

(58) Field of Classification Search
CPC ....... C07K 14/605; A61K 38/26; A61K 38/00
See application file for complete search history.

(56) References Cited

U.S. PATENT DOCUMENTS

| | | | |
|---|---|---|---|
| 6,268,343 B1 | 7/2001 | Knudsen et al. | |
| 9,006,178 B2* | 4/2015 | Kofoed | A61K 47/48038 514/11.7 |
| 2003/0144471 A1* | 7/2003 | Jonassen | C07K 1/006 530/300 |
| 2008/0207507 A1* | 8/2008 | Lau | C07K 14/605 514/1.1 |
| 2014/0303083 A1 | 10/2014 | Lau et al. | |
| 2015/0133374 A1 | 5/2015 | Kofoed et al. | |
| 2017/0145069 A1 | 5/2017 | Lau et al. | |
| 2018/0244742 A1 | 8/2018 | Kofoed et al. | |

FOREIGN PATENT DOCUMENTS

| | | |
|---|---|---|
| CN | 1893980 A | 1/2007 |
| EP | 1512692 A2 | 3/2005 |
| JP | 2003531871 A | 10/2003 |
| JP | 2007-505840 A | 3/2007 |
| JP | 2007537141 A | 12/2007 |
| WO | 9808871 A1 | 3/1998 |
| WO | WO 98/08871 * | 3/1998 |
| WO | 99/43706 A1 | 9/1999 |
| WO | 00/07617 A1 | 2/2000 |
| WO | 01/51071 A2 | 7/2001 |
| WO | 2006/051103 A2 | 5/2006 |
| WO | 06097537 A2 | 9/2006 |
| WO | WO 2006/097537 * | 9/2006 |
| WO | WO2010/015668 * | 2/2010 |
| WO | 2011/080103 A1 | 7/2011 |
| WO | WG2011/080103 * | 7/2011 |

(Continued)

OTHER PUBLICATIONS 9-page linker search result document, Centre for Integrative Bioinformatics VU, Universiteit amsterdam, printed Apr. 3, 2016.*
Prasad et al., Delivering multiple anticancer peptides as a single prodrug using lysyl-lysine as a facile linker, J Pept Sci. Jul. 2007;13(7):458-67.*
Madsen et al., Structure-Activity and Protraction Relationship of Long-Acting Glucagon-like Peptide-1 Derivatives: Importance of Fatty Acid Length, Polarity, and Bulkiness, J. Med. Chem., 2007, 50 (24), pp. 6126-6132.*
PDF of Abstract and diagram of Madsen et al., Structure-Activity and Protraction Relationship of Long-Acting Glucagon-like Peptide-1 Derivatives: Importance of Fatty Acid Length, Polarity, and Bulkiness, J. Med. Chem., 2007, 50 (24), pp. 6126-6132.*

(Continued)

*Primary Examiner* — Larry D Riggs, II
*Assistant Examiner* — Joseph Fischer
(74) *Attorney, Agent, or Firm* — Jianjie Hu

(57) ABSTRACT

The invention relates to a derivative of a GLP-1 peptide, which peptide comprises a first K residue and a second K residue, at positions corresponding to position 26, and 34, respectively, of GLP-1(7-37) (SEQ ID NO:1), and a maximum of eight amino acid changes as compared to GLP-1 (7-37); which derivative comprises two protracting moieties attached to said first and second K residue, respectively, via a linker, wherein the protracting moiety is Chem. 2: HOOC—$C_6H_4$—O—$(CH_2)_y$—CO—*, in which y is an integer in the range of 6-13; and the linker comprises Chem. 3a: *—NH—$(CH_2)_q$—CH[$(CH_2)_w$—$NR_1R_2$]—CO—*, wherein q is an integer in the range of 0-5, $R_1$ and $R_2$ independently represent *—H or *—$CH_3$, and w is an integer in the range of 0-5; or a pharmaceutically acceptable salt, amide, or ester thereof. The invention also relates to the pharmaceutical use thereof, for example in the treatment and/or prevention of all forms of diabetes and related diseases, as well as to corresponding novel peptide and linker intermediates. The derivatives are potent, stable, protracted, and suitable for oral administration.

15 Claims, No Drawings

Specification includes a Sequence Listing.

(56) References Cited

FOREIGN PATENT DOCUMENTS

| WO | WO-2011080103 A1 * | 7/2011 | ............. A61K 38/00 |
| WO | WO-2012062804 A1 * | 5/2012 | ............. A61P 43/00 |
| WO | 2013/037690 A1 | 3/2013 | |
| WO | WO-2013037690 A1 * | 3/2013 | ............. A61P 15/08 |
| WO | 2013/167454 A1 | 11/2013 | |

OTHER PUBLICATIONS

Lambeir et al., Critical Reviews in Clinical Laboratory Sciences, 40:3, 209-294 (2003) (Year: 2003).*
Arulmozhi and Portha, european journal of pharmaceutical sciences 2 8 (2 0 0 6) 96-108 (Year: 2006).*
Madsen et al., J. Med. Chem. 2007, 50, 6126-6132 (Year: 2007).*
Knudsen L B et al.Potent Derivatives of Glucagon-like Peptide-1 with Pharmacokinetic Properties Suitable for Once Daily Administration, Journal :Journal of Medicinal Chemistry.Year 2000, vol. 43,pp. 1664-1669.
Leeper et al., "Synthesis of Bridged Thiazolium Salts as Models for Thiamin," Journal of the Chemical Society, Perkin Transactions 1, 1995, No. 7, pp. 861-873.
Arulmozhi et al.,"GLP-1 based therapy for type 2 diabetes." European journal of pharmaceutical sciences, May 2006, vol. 28, No. I-2, pp. 96-108.
Lambeir et al.,"Dipeptidyl-peptidase IV from bench to bedside: an update on structural properties, functions, and clinical aspects of the enzyme DPP IV." Critical reviews in clinical laboratory sciences, 2003, vol. 40, No. 3, pp. 209-294.

* cited by examiner

SEQUENCE LISTING

<160> NUMBER OF SEQ ID NOS: 7

<210> SEQ ID NO 1
<211> LENGTH: 31
<212> TYPE: PRT
<213> ORGANISM: Homo sapiens
<220> FEATURE:
<221> NAME/KEY: mat_peptide
<222> LOCATION: (1)..(31)

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 2
<211> LENGTH: 31
<212> TYPE: PRT
<213> ORGANISM: Artificial
<220> FEATURE:
<223> OTHER INFORMATION: GLP-1 analogue
<220> FEATURE:
<221> NAME/KEY: mat_peptide
<222> LOCATION: (1)..(31)
<220> FEATURE:
<221> NAME/KEY: MISC_FEATURE
<222> LOCATION: (2)..(2)
<223> OTHER INFORMATION: Xaa2 is Aib

<400> SEQUENCE: 2

His Xaa Glu Gly Thr Phe Thr Ser Asp Val Ser Ser Tyr Leu Glu Glu
1               5                   10                  15

Gln Ala Ala Lys Glu Phe Ile Glu Trp Leu Val Lys Gly Arg Gly
            20                  25                  30

<210> SEQ ID NO 3
<211> LENGTH: 32
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = L-histidine, imidazopropionyl (Imp),
      alpha-hydroxy-histidine, D-histidine, desamino-histidine (desH),
      2-amino-histidine, beta-hydroxy-histidine, homohistidine,
      Nalpha-acetyl-histidine, Nalpha-formyl-histidine,
<220> FEATURE:
<221> NAME/KEY: MISC_FEATURE
<222> LOCATION: (2)..(2)
<223> OTHER INFORMATION: Xaa = Ala, Gly, Val, Leu, Ile, Thr, Ser, Lys,
      Aib, (1-aminocyclopropyl) carboxylic acid, (1-aminocyclobutyl)
      carboxylic acid, (1-aminocyclopentyl) carboxylic acid,
      (1-aminocyclohexyl) carboxylic acid, (1-aminocycloheptyl)
<220> FEATURE:
<221> NAME/KEY: MISC_FEATURE
<222> LOCATION: (6)..(6)
<223> OTHER INFORMATION: Xaa = Phe or Leu
<220> FEATURE:
<221> NAME/KEY: MISC_FEATURE
<222> LOCATION: (10)..(10)
<223> OTHER INFORMATION: Xaa = Val or Leu
<220> FEATURE:
<221> NAME/KEY: MISC_FEATURE
<222> LOCATION: (12)..(12)
<223> OTHER INFORMATION: Xaa = Ser, Val or Leu
<220> FEATURE:
<221> NAME/KEY: MISC_FEATURE
<222> LOCATION: (13)..(13)
<223> OTHER INFORMATION: Xaa = Tyr or Gln

```
<220> FEATURE:
<221> NAME/KEY: MISC_FEATURE
<222> LOCATION: (14)..(14)
<223> OTHER INFORMATION: Xaa = Leu or Met
<220> FEATURE:
<221> NAME/KEY: MISC_FEATURE
<222> LOCATION: (16)..(16)
<223> OTHER INFORMATION: Xaa = Gly, Glu or Aib
<220> FEATURE:
<221> NAME/KEY: MISC_FEATURE
<222> LOCATION: (17)..(17)
<223> OTHER INFORMATION: Xaa = Gln, Glu or Arg
<220> FEATURE:
<221> NAME/KEY: MISC_FEATURE
<222> LOCATION: (19)..(19)
<223> OTHER INFORMATION: Xaa = Ala or Val
<220> FEATURE:
<221> NAME/KEY: MISC_FEATURE
<222> LOCATION: (21)..(21)
<223> OTHER INFORMATION: Xaa = Glu or Leu
<220> FEATURE:
<221> NAME/KEY: MISC_FEATURE
<222> LOCATION: (24)..(24)
<223> OTHER INFORMATION: Xaa = Ala, Glu or Arg
<220> FEATURE:
<221> NAME/KEY: MISC_FEATURE
<222> LOCATION: (25)..(25)
<223> OTHER INFORMATION: Xaa = Trp or His
<220> FEATURE:
<221> NAME/KEY: MISC_FEATURE
<222> LOCATION: (27)..(27)
<223> OTHER INFORMATION: Xaa = Val
<220> FEATURE:
<221> NAME/KEY: MISC_FEATURE
<222> LOCATION: (29)..(29)
<223> OTHER INFORMATION: Xaa = Gly or Aib
<220> FEATURE:
<221> NAME/KEY: MISC_FEATURE
<222> LOCATION: (30)..(30)
<223> OTHER INFORMATION: Xaa = Arg or Gly
<220> FEATURE:
<221> NAME/KEY: MISC_FEATURE
<222> LOCATION: (31)..(31)
<223> OTHER INFORMATION: Xaa = Gly or Arg
<220> FEATURE:
<221> NAME/KEY: MISC_FEATURE
<222> LOCATION: (32)..(32)
<223> OTHER INFORMATION: Xaa = Ser, Gly, Ala, Glu, Pro, Arg or absent

<400> SEQUENCE: 3

Xaa Xaa Glu Gly Thr Xaa Thr Ser Asp Xaa Ser Xaa Xaa Xaa Glu Xaa
1               5                   10                  15

Xaa Ala Xaa Lys Xaa Phe Ile Xaa Xaa Leu Xaa Lys Xaa Xaa Xaa Xaa
            20                  25                  30

<210> SEQ ID NO 4
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = Aib

<400> SEQUENCE: 4

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 5
```

```
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Imp
<220> FEATURE:
<221> NAME/KEY: MISC_FEATURE
<222> LOCATION: (2)..(2)
<223> OTHER INFORMATION: Xaa = Aib

<400> SEQUENCE: 5

Xaa Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 6
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = Aib

<400> SEQUENCE: 6

His Xaa Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg Gly
            20                  25                  30

<210> SEQ ID NO 7
<211> LENGTH: 31
<212> TYPE: PRT
<213> ORGANISM: Artificial Sequence
<220> FEATURE:
<223> OTHER INFORMATION: Synthetich
<220> FEATURE:
<221> NAME/KEY: MISC_FEATURE
<222> LOCATION: (2)..(2)
<223> OTHER INFORMATION: Xaa = Aib

<400> SEQUENCE: 7

His Xaa Glu Gly Thr Phe Thr Ser Asp Val Ser Ser Tyr Leu Glu Glu
1               5                   10                  15

Gln Ala Ala Lys Glu Phe Ile Glu Trp Leu Val Lys Gly Arg Gly
            20                  25                  30
```

DOUBLE-ACYLATED GLP-1 DERIVATIVES

TECHNICAL FIELD

The present invention relates to derivatives of analogues of Glucagon-Like Peptide 1 (GLP-1), more in particular to double-acylated GLP-1 derivatives acylated at $K^{26}$ and at $K^{34}$, and their pharmaceutical use.

CROSS-REFERENCE TO RELATED APPLICATIONS

This application is a 35 U.S.C. § 371 National Stage application of International Application PCT/EP2013/059113 (WO 2013/167455), filed May 2, 2013, which claimed priority of European Patent Application 12167093.9, filed May 8, 2012 and of U.S. Provisional Application 61/646,469; filed May 14, 2012; the contents of which is incorporated herein by reference.

SEQUENCE LISTING

The instant application contains a Sequence Listing which has been submitted in ASCII format via EFS-Web and is hereby incorporated by reference in its entirety. Said ASCII copy, created on Oct. 5, 2015, is named 8499SeqList_ST25.txt and is 5,065 bytes in size.

BACKGROUND

Journal of Medicinal Chemistry (2000), vol. 43, no. 9, p. 1664-669 discloses derivatives of GLP-1(7-37) that are double-acylated at $K^{26,34}$.

WO 99/43706 A1 discloses a number of mono- and double-acylated GLP-1 derivatives.

WO 98/08871 A1 discloses a number of GLP-1 derivatives including some that are double-acylated.

WO 2011/080103 A1 discloses a number of GLP-1 derivatives that are double-acylated at $K^{26,37}$.

SUMMARY

The invention relates to derivatives of GLP-1 peptides.

Liraglutide is a mono-acylated GLP-1 derivative for once daily administration which is marketed as of 2009 by Novo Nordisk NS. This compound is disclosed in WO 98/08871 A1 (Example 37).

WO 06/097537 A2 discloses among other GLP-1 derivatives semaglutide (Example 4), which is a mono-acylated GLP-1 derivative for once weekly administration which is under development by Novo Nordisk NS.

The derivatives of the invention are acylated at the native lysines at positions 26 and 34. The side chains are albumin binding moieties comprising a protracting moiety selected from fatty acids with a distal carboxy-phenoxy group being acylated, optionally via a linker, to a lysine residue of the GLP-1 peptide, preferably at the epsilon-amino group thereof.

The GLP-1 peptide may be GLP-1(7-37) (SEQ ID NO:1), or an analogue thereof having a total of up to eight amino acid changes as compared to GLP-1(7-37). The changes are, independently, one or more additions, one or more deletions, and/or one or more substitutions.

More in particular, the invention relates to a derivative of a GLP-1 peptide, which peptide comprises a first K residue at a position corresponding to position 26 of GLP-1(7-37) (SEQ ID NO:1), a second K residue at a position corresponding to position 34 of GLP-1(7-37) (SEQ ID NO:1), and a maximum of eight amino acid changes as compared to GLP-1(7-37), which derivative comprises two protracting moieties attached to said first and second K residue, respectively, each via a linker, wherein the protracting moiety is Chem. 2: HOOC—$C_6H_4$—O—$(CH_2)_y$—CO—*, in which y is an integer in the range of 6-13; and each linker comprises Chem. 3a: *—NH—$(CH_2)_q$—CH[$(CH_2)_w$—$NR_1R_2$]—CO—*, wherein q is an integer in the range of 0-5, $R_1$ and $R_2$ independently represent a hydrogen radical (*—H) or methyl (*—$CH_3$), and w is an integer in the range of 0-5; or a pharmaceutically acceptable salt, amide, or ester thereof.

The invention also relates to such derivative for use as a medicament, in particular for use in the treatment and/or prevention of all forms of diabetes and related diseases, such as eating disorders, cardiovascular diseases, gastrointestinal diseases, diabetic complications, critical illness, and/or polycystic ovary syndrome; and/or for improving lipid parameters, improving p-cell function, and/or for delaying or preventing diabetic disease progression.

The invention furthermore relates to intermediate products in the form of novel GLP-1 analogues, which are relevant for the preparation of certain derivatives of the invention.

The invention furthermore relates to an intermediate compound in the form of a novel protected compound (Chem. 39, Example 19) that may be used in the synthesis of the compound of Example 13 herein, and similar compounds.

The derivatives of the invention are biologically active. Also, or alternatively, they have a protracted pharmacokinetic profile. Also, or alternatively, they have a high oral bioavailability. These properties are of importance in the development of next generation GLP-1 compounds for subcutaneous, intravenous, and/or in particular oral administration.

DESCRIPTION

In what follows, Greek letters may be represented by their symbol or the corresponding written name, for example: α=alpha; β=beta; ε=epsilon; γ=gamma; ω=omega; etc. Also, the Greek letter of μ may be represented by "u", e.g. in μl=ul, or in μM=uM.

An asterisk (*) in a chemical formula designates i) a point of attachment, ii) a radical, and/or iii) an unshared electron.

In a first aspect, the invention relates to a derivative of a GLP-1 peptide, which peptide comprises a first K residue at a position corresponding to position 26 of GLP-1(7-37) (SEQ ID NO:1), a second K residue at a position corresponding to position 34 of GLP-1(7-37) (SEQ ID NO:1), and a maximum of eight amino acid changes as compared to GLP-1(7-37), which derivative comprises two protracting moieties attached to said first and second K residue, respectively, via a linker, wherein the protracting moiety is Chem. 2:

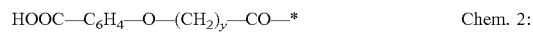

HOOC—$C_6H_4$—O—$(CH_2)_y$—CO—*    Chem. 2:

in which y is an integer in the range of 6-13; and the linker comprises

*—NH—$(CH_2)_q$—CH[$(CH_2)_w$—$NR_1R_2$]—CO—*,    Chem. 3:

wherein q is an integer in the range of 0-5, $R_1$ and $R_2$ independently represent *—H or *—$CH_3$, and w is an integer in the range of 0-5; or a pharmaceutically acceptable salt, amide, or ester thereof.

GLP-1 Peptides and Analogues

The term "GLP-1 peptide" as used herein refers to the human Glucagon-Like Peptide-1 (GLP-1(7-37)), the sequence of which is included in the sequence listing as SEQ ID NO:1, or an analogue thereof. The peptide having the sequence of SEQ ID NO:1 may also be designated "native" GLP-1.

The term "GLP-1 analogue" or "analogue of GLP-1" as used herein refers to a peptide, or a compound, which is a variant of GLP-1(7-37) (SEQ ID NO:1).

In the sequence listing, the first amino acid residue of SEQ ID NO:1 (histidine) is assigned no. 1. However, in what follows—according to established practice in the art—this histidine residue is referred to as no. 7, and subsequent amino acid residues are numbered accordingly, ending with glycine no. 37. Therefore, generally, any reference herein to an amino acid residue number or a position number of the GLP-1(7-37) sequence is to the sequence starting with His at position 7 and ending with Gly at position 37.

GLP-1 analogues of the derivatives of the invention may be described by reference to i) the number of the amino acid residue in native GLP-1(7-37) which corresponds to the amino acid residue which is changed (i.e., the corresponding position in native GLP-1), and to ii) the actual change.

The GLP-1 analogue forming part of the derivative of the invention comprises a maximum of eight amino acid changes when compared with native GLP-1(7-37) (SEQ ID NO:1). In other words, it is a GLP-1(7-37) peptide in which a number of amino acid residues have been changed when compared to native GLP-1(7-37) (SEQ ID NO:1). These changes may represent, independently, one or more amino acid substitutions, additions, and/or deletions.

The following are non-limiting examples of appropriate analogue nomenclature.

For example, the analogue [Imp$^7$, Aib$^8$]-GLP-1-(7-37) designates a GLP-1(7-37) peptide which, when compared to native GLP-1, has the following substitutions: Substitution of histidine at position 7 with imidazopropionyl (that may also be designated des-amino histidine (desH)), and substitution of alanine at position 8 with Aib (α-aminoisobutyric acid). This analogue may also be briefly designated (7Imp, 8Aib), where reference to GLP-1(7-37) is implied.

Analogues "comprising" certain specified changes may comprise further changes, when compared to SEQ ID NO:1.

As is apparent from the above examples, amino acid residues may be identified by their full name, their one-letter code, and/or their three-letter code. These three ways are fully equivalent.

The expressions "a position equivalent to" or "corresponding position" may be used to characterise the site of change in a variant GLP-1(7-37) sequence by reference to native GLP-1(7-37) (SEQ ID NO:1). Equivalent or corresponding positions, as well as the number of changes, are easily deduced, e.g. by simple handwriting and eyeballing; and/or a standard protein or peptide alignment program may be used, such as "align" which is a Needleman-Wunsch alignment. The algorithm is described in Needleman, S. B. and Wunsch, C. D., (1970), Journal of Molecular Biology, 48: 443-453, and the align program by Myers and W. Miller in "Optimal Alignments in Linear Space" CABIOS (computer applications in the biosciences) (1988) 4:11-17. For the alignment, the default scoring matrix BLOSUM50 and the default identity matrix may be used, and the penalty for the first residue in a gap may be set at −12, or preferably at −10, and the penalties for additional residues in a gap at −2, or preferably at −0.5.

An example of such alignment is inserted hereinbelow, in which sequence no. 1 (SEQ_ID_NO_1) is SEQ ID NO:1, and sequence no. 2 (SEQ ID NO: 2)(ANALOGUE) is the analogue (8Aib, 22E, 30E) thereof:

```
# Aligned_sequences: 2
# 1: SEQ_ID_NO_1
# 2: ANALOGUE
# Matrix: EBLOSUM62
# Gap_penalty: 10.0
# Extend_penalty: 0.5
# Length: 31
# Identity:   28/31 (90.3%)
# Similarity: 28/31 (90.3%)
# Gaps:        0/31 ( 0.0%)
# Score: 145.0
SEQ_ID_NO_1   1 HAEGTFTSDVSSYLEGQAAKEFIAWLVKGRG  31
                |.||||| .|||||||.|||||||||||||||
ANALOGUE      1 HXEGTFTEDVSSYLEEQAAKEFIAWLVKGRG  31
(SEQ ID NO: 2)
```

As can be inferred from the above alignment, in case of non-natural amino acids such as Aib being included in the sequence, these may, for alignment purposes, be replaced with X. If desired, X can later be manually corrected.

The term "peptide", as e.g. used in the context of the GLP-1 analogues of the derivatives of the invention, refers to a compound which comprises a series of amino acids interconnected by amide (or peptide) bonds.

The peptides of the invention comprise at least five constituent amino acids connected by peptide bonds. In particular embodiments the peptide comprises at least 10, preferably at least 15, more preferably at least 20, even more preferably at least 25, or most preferably at least 28 amino acids.

In particular embodiments, the peptide is composed of at least five constituent amino acids, preferably composed of at least 10, at least 15, at least 20, at least 25, or most preferably composed of at least 28 amino acids.

In additional particular embodiments, the peptide is a) composed of, or b) consists of, i) 28, ii) 29, iii) 30, iv) 31, v) 32, or vi) 33 amino acids.

In a still further particular embodiment the peptide consists of amino acids interconnected by peptide bonds.

Amino acids are molecules containing an amine group and a carboxylic acid group, and, optionally, one or more additional groups, often referred to as a side chain.

The term "amino acid" includes proteogenic amino acids (encoded by the genetic code, including natural amino acids, and standard amino acids), as well as non-proteogenic (not found in proteins, and/or not coded for in the standard genetic code), and synthetic amino acids. Thus, the amino acids may be selected from the group of proteinogenic amino acids, non-proteinogenic amino acids, and/or synthetic amino acids.

Non-limiting examples of amino acids which are not encoded by the genetic code are gamma-carboxyglutamate, ornithine, and phosphoserine. Non-limiting examples of synthetic amino acids are the D-isomers of the amino acids such as D-alanine and D-leucine, Aib (α-aminoisobutyric acid), β-alanine, and des-amino-histidine (desH, alternative name imidazopropionic acid, abbreviated Imp).

In what follows, all specific amino acids for which the optical isomer is not stated is to be understood to mean the L-isomer (unless otherwise specified), e.g. when reference is made to the specific amino acid of glutamine, this is intended to refer to L-glutamine, unless otherwise is stated. On the other hand, where amino acids are described by more general formulas such as brutto formulas or structural formulas and when no stereo chemistry is shown, these formulas are intended to cover all stereo isomers.

The GLP-1 derivatives and analogues of the invention have GLP-1 activity. This term refers to the ability to bind to the GLP-1 receptor and initiate a signal transduction pathway resulting in insulinotropic action or other physiological effects as is known in the art. For example, the analogues and derivatives of the invention can be tested for GLP-1 activity using one or more of the assays described in Examples 20-21 herein. The GLP-1 receptor binding assay described in Example 22 herein may also, if relevant, be used as a measure of GLP-1 activity, or, more precisely, GLP-1 receptor affinity (the low HSA experiment).

GLP-1 Derivatives

The term "derivative" as used herein in the context of a GLP-1 peptide or analogue means a chemically modified GLP-1 peptide or analogue, in which one or more substituents have been covalently attached to the peptide. The substituent may also be referred to as a side chain.

In a particular embodiment, the side chain is capable of forming non-covalent aggregates with albumin, thereby promoting the circulation of the derivative with the blood stream, and also having the effect of protracting the time of action of the derivative, due to the fact that the aggregate of the GLP-1-derivative and albumin is only slowly disintegrated to release the active pharmaceutical ingredient. Thus, the substituent, or side chain, as a whole is preferably referred to as an albumin binding moiety.

In another particular embodiment the albumin binding moiety comprises a portion which is particularly relevant for the albumin binding and thereby the protraction, which portion may accordingly be referred to as a protracting moiety. The protracting moiety may be at, or near, the opposite end of the albumin binding moiety, relative to its point of attachment to the peptide.

In a still further particular embodiment the albumin binding moiety comprises a portion inbetween the protracting moiety and the point of attachment to the peptide, which portion may be referred to as a linker, linker moiety, spacer, or the like. The linker may be optional, and hence in that case the albumin binding moiety may be identical to the protracting moiety.

In particular embodiments, the albumin binding moiety and/or the protracting moiety is lipophilic, and/or negatively charged at physiological pH (7.4).

The albumin binding moiety, the protracting moiety, or the linker may be covalently attached to a lysine residue of the GLP-1 peptide by acylation.

In a preferred embodiment, an active ester of the albumin binding moiety, preferably comprising a protracting moiety and a linker, is covalently linked to an amino group of a lysine residue, preferably the epsilon amino group thereof, under formation of an amide bond (this process being referred to as acylation).

Unless otherwise stated, when reference is made to an acylation of a lysine residue, it is understood to be to the epsilon-amino group thereof.

A derivative comprising two protracting moieties attached to a first and a second K residue (viz. to $K^{26}$ and $K^{34}$) via a linker may be referred to as a derivative which has been acylated twice, double-acylated, or dual acylated at the epsilon-amino groups of the first and second lysine residues, e.g. at position 26 and 34, respectively, of the GLP-1 peptide.

For the present purposes, the terms "albumin binding moiety", "protracting moiety", and "linker" may include the unreacted as well as the reacted forms of these molecules. Whether or not one or the other form is meant is clear from the context in which the term is used.

In one aspect, each protracting moiety comprises, or consists of, a protracting moiety independently selected from Chem. 2:

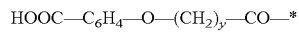

Chem. 2:

in which y is an integer in the range of 6-13.

In one embodiment, *—$(CH_2)_y$—* refers to straight alkylene in which y is an integer in the range of 6-13.

The term "fatty acid" refers to aliphatic monocarboxylic acids having from 4 to 28 carbon atoms, it is preferably unbranched, and/or even numbered, and it may be saturated or unsaturated.

The nomenclature is as is usual in the art, for example in the above formulas *—COOH as well as HOOC—* refers to carboxy; *—$C_6H_4$—* to phenylene; *—CO—*, as well as *—OC—*, to carbonyl (O=C<**); $C_6H_5$—O—* to phenoxy. Furthermore, CO—* refers to C(=O)—*. For example, in any formula (R—CO—*) herein (where R is as defined by each formula), R—CO—*, refers to R—C(=O)—*. In particular embodiments, the aromatics, such as the phenoxy, and the phenylene radicals, may be para.

As explained above, the GLP-1 derivatives of the present invention are double-acylated, i.e. two albumin binding moieties are covalently attached to the GLP-1 peptide.

In a particular embodiment, the two albumin binding moieties (i.e. the entire side chains) are similar, preferably substantially identical, or, most preferably, identical.

In another particular embodiment, the two protracting moieties are similar, preferably substantially identical, or, most preferably, identical.

In a still further particular embodiment, the two linkers are similar, preferably substantially identical, or, most preferably identical.

The term "substantially identical" includes differences from identity which are due to formation of one or more salts, esters, and/or amides; preferably formation of one or more salts, methyl esters, and simple amides; more preferably formation of no more than two salts, methyl esters, and/or simple amides; even more preferably formation of no more than one salt, methyl ester, and/or simple amide; or most preferably formation of no more than one salt.

In the context of chemical compounds such as the albumin binding moeities, protracting moieties, and linkers, similarity and/or identity may be determined using any suitable computer program and/or algorithm known in the art.

For example, the similarity of two protracting moieties, two linkers, and/or two entire side chains may suitably be determined using molecular fingerprints. Fingerprints is a mathematical method of representing a chemical structure (see e.g. Chemoinformatics: A textbook, Johann Gasteiger and Thomas Engel (Eds), Wiley-VCH Verlag, 2003).

Examples of suitable fingerprints include, without limitation, UNITY fingerprints, MDL fingerprints, and/or ECFP fingerprints, such as ECFP_6 fingerprints (ECFP stands for extended-connectivity fingerprints).

In particular embodiments, the two protracting moieties, the two linkers, and/or the two entire side chains are represented as a) ECFP_6 fingerprints; b) UNITY fingerprints; and/or c) MDL fingerprints.

The Tanimoto coefficient is preferably used for calculating the similarity of the two fingerprints, whether a), b), or c) is used.

In particular embodiments, whether a), b), or c) is used, the two protracting moieties, the two linkers, and/or the two entire side chains, respectively, have a similarity of at least 0.5 (50%); preferably at least 0.6 (60%); more preferably at least 0.7 (70%), or at least 0.8 (80%); even more preferably at least 0.9 (90%); or most preferably at least 0.99 (99%), such as a similarity of 1.0 (100%).

UNITY fingerprints may be calculated using the programme SYBYL (available from Tripos, 1699 South Hanley Road, St. Louis, Mo. 63144-2319 USA). ECFP_6 and MDL fingerprints may be calculated using the programme Pipeline Pilot (available from Accelrys Inc., 10188 Telesis Court, Suite 100, San Diego, Calif. 92121, USA).

For more details, see for example J. Chem. Inf. Model. 2008, 48, 542-549; J. Chem. Inf. Comput. Sci. 2004, 44, 170-178; J. Med. Chem. 2004, 47, 2743-2749; J. Chem. Inf. Model. 2010, 50, 742-754; as well as SciTegic Pipeline Pilot Chemistry Collection: Basic Chemistry User Guide, March 2008, SciTegic Pipeline Pilot Data Modeling Collection, 2008—both from Accelrys Software Inc., San Diego, US, and the guides http://www.tripos.com/tripos_resources/fileroot/pdfs/Unity_111408. pdf, and http://www.tripos.com/data/SYBYL/SYBYL_072505. pdf.

An example of a similarity calculation is inserted hereinbelow, in which a known entire side chain of a known GLP-1 derivative was compared with a methyl ester thereof:

tion (the alpha atom is the C-atom next to the carboxylic acid function, and each upstream C-atom is then designated using the subsequent Greek letters beta, gamma, delta, and so on, until the C-atom to which the *—NH group is attached is reached, and it is in case of lysine the epsilon atom. Accordingly, when w=0, $R_1$ and $R_2$ both represent *—H, and q=4, the formula Chem. 3a refers to a di-radical of epsilon-lysine (eps-Lys; Chem. 6).

Another non-limiting example of a linker comprising this first linker element of Chem. 3a is $N^\alpha,N^\alpha$-dimethyl lysine, or rather a di-radical of this residue (6-amino-(S)-2-(dimethylamino)hexanoyl). Also $N^\alpha,N^\alpha$-dimethyl lysine may preferably be used as a linker in its omega-version, where omega refers to the fact that it is the amino group at the distal C-atom of the alkyl substituent chain that is radicalised (to *—NH). Also for $N^\alpha,N^\alpha$-dimethyl lysine the omega position is herein generally referred to as the epsilon position (the alpha atom is the C-atom next to the carboxylic acid function, and each upstream C-atom is then designated using the subsequent Greek letters beta, gamma, delta, and so on, until the C-atom to which the *—NH group is attached is reached, and it is in case of N,N-dimethyl lysine the epsilon atom. Accordingly, when w=0, $R_1$ and $R_2$ both represent *—$CH_3$, and q=4, the formula Chem. 3a refers to a di-radical of $N^\alpha,N^\alpha$-dimethyl epsilon lysine (in brief "N,N-dimethyl-eps-Lys"; Chem. 6a).

In a preferred embodiment, this first linker element is in its L-form.

The linker may comprise 1 or 2 times Chem. 3a. When z is 2 the Chem. 3a elements are preferably interconnected via

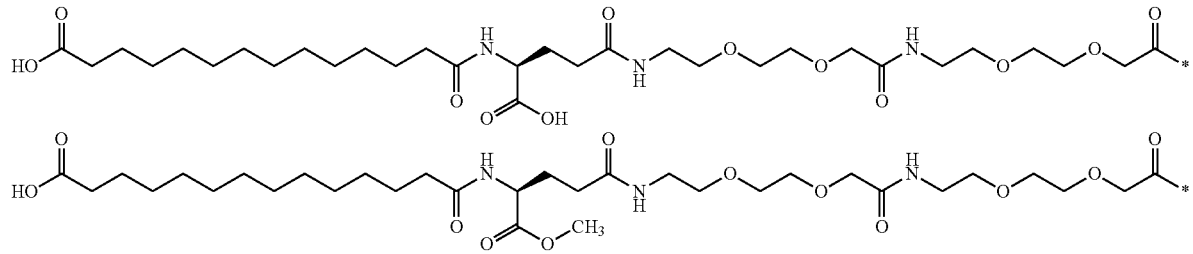

Using a) ECFP_6 fingerprints the similarity is 0.798, using b) UNITY fingerprints the similarity is 0.957; and using MDL fingerprints the similarity is 0.905.

In case of two identical side chains (albumin binding moieties) the derivative may be designated symmetrical.

In particular embodiments, the similarity coefficient is at least 0.80, preferably at least 0.85, more preferably at least 0.90, even more preferably at least 0.95, or most preferably at least 0.99.

Each of the two linkers of the derivative of the invention comprises the following first linker element (A): Chem. 3a:

*—NH—$(CH_2)_q$—CH[$(CH_2)_w$—$NR_1R_2$]—CO—*, wherein q is an integer in the range of 0-5, $R_1$ and $R_2$ independently represent *—H (a hydrogen radical), or *—$CH_3$ (methyl), and w is an integer in the range of 0-5.

One non-limiting example of a linker comprising this first linker element of Chem. 3a is lysine, or rather a di-radical of lysine. Lysine may preferably be used as a linker in its omega-version, where omega refers to the fact that it is the amino group at the distal C-atom of the alkyl substituent chain that is radicalised (to *—NH). For lysine the omega position is herein generally referred to as the epsilon posian amide bond. For example, the linker may comprise two times epsilon-Lys (2xeps-Lys; 2xChem. 6).

The linker (each of the first and second linker) may further (i.e., in addition to one or two times the first linker element (A)) comprise one or more additional linker elements, e.g. linker elements independently selected from the second (B), and/or third (C) linker elements, as defined in the following:

A second linker element (B):

Chem. 12

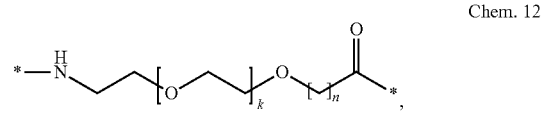

wherein k is an integer in the range of 1-5, and n is an integer in the range of 1-5.

In a particular embodiment, when k=1 and n=1, this linker element may be designated OEG, or 8-amino-3,6-dioxaoctanic acid, and/or it may be represented by the following formula:

*—NH—$(CH_2)_2$—O—$(CH_2)_2$—O—$CH_2$—CO—*.     Chem. 12a:

A third linker element (C), gamma-glutamic acid (gGlu):

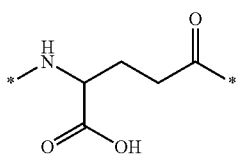

Chem. 14

In gamma-Glu (gGlu) it is the gamma carboxy group of the amino acid glutamic acid which is here used for connection to another linker element, or to the epsilon-amino group of lysine.

In one, non-limiting, particular embodiment, each linker consists of Chem. 14 and two times Chem. 6 (Chem.14-2xChem.6), interconnected via amide bonds and in the sequence indicated, connected at its *—NH end to the CO—* end of the protracting moiety, and at its CO—* end to the epsilon amino group of the first or the second K residue of the GLP-1 analogue.

For example, the first linker consists of (Chem.14-2xChem.6), interconnected via amide bonds and in the sequence indicated, connected at its *—NH end to the CO—* end of the first protracting moiety, and at its CO—* end to the epsilon amino group of the first K residue of the GLP-1 analogue; and the second linker consists of (Chem.14-2xChem.6), interconnected via amide bonds and in the sequence indicated, connected at its *—NH end to the CO—* end of the second protracting moiety, and at its CO—* end to the epsilon amino group of the second K residue of the GLP-1 analogue.

Needless to say, just for the sake of good order: Here and in the following the phrase "in the sequence indicated" means, that the *—NH end of the first-mentioned linker element (here Chem. 14) is connected to the CO—* end of the protractor, and the CO—* end of the last-mentioned linker element (here the last one of the two times Chem. 6) is connected to the epsilon amino group of the K residue in question of the GLP-1 analogue.

The derivatives of the invention may exist in different stereoisomeric forms having the same molecular formula and sequence of bonded atoms, but differing only in the three-dimensional orientation of their atoms in space. The stereoisomerism of the exemplified derivatives of the invention is indicated in the experimental section, in the names as well as the structures, using standard nomenclature. Unless otherwise stated the invention relates to all stereoisomeric forms of the claimed derivative.

The concentration in plasma of the GLP-1 derivatives of the invention may be determined using any suitable method. For example, LC-MS (Liquid Chromatography Mass Spectroscopy) may be used, or immunoassays such as RIA (Radio Immuno Assay), ELISA (Enzyme-Linked Immuno Sorbent Assay), and LOCI (Luminescence Oxygen Channeling Immunoassay). General protocols for suitable RIA and ELISA assays are found in, e.g., WO09/030738 on p. 116-118. A preferred assay is the LOCI assay, e.g. described in Example 24 herein.

Intermediate Products

The invention also relates to an intermediate product in the form of a GLP-1 analogue selected from the following analogues of GLP-1(7-37) (SEQ ID NO:1): (i) 8Aib; (ii) 7Imp, 8Aib; (iii) 8Aib, 22E; or (iv) 8Aib, 22E, 30E; or a pharmaceutically acceptable salt, amide, or ester of any of the analogues of (i), (ii), (iii), or (iv).

The invention furthermore relates to an intermediate product in the form of a novel protected linker compound that may be used in the synthesis of the compound of Example 13 herein and similar compounds, namely the compound (S)-2-Dimethylamino-6-(9H-fluoren-9-yl-methoxycarbonylamino)-hexanoic acid, with the structure of Chem. 39:

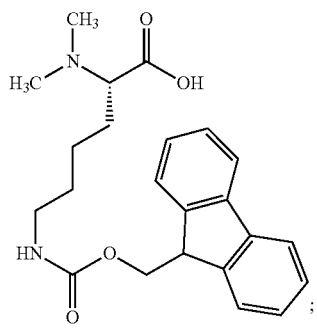 [SMILES: CN(C)[C@@H](CCCCNC(=O)OCC1c2ccccc2-c2ccccc21)C(=O)O]

or a pharmaceutically acceptable salt, amide, or ester thereof.

Pharmaceutically Acceptable Salt, Amide, or Ester

The intermediate products, analogues and derivatives of the invention may be in the form of a pharmaceutically acceptable salt, amide, or ester.

Salts are e.g. formed by a chemical reaction between a base and an acid, e.g.: $2\ NH_3 + H_2SO_4 \rightarrow (NH_4)_2SO_4$.

The salt may be a basic salt, an acid salt, or it may be neither nor (i.e. a neutral salt). Basic salts produce hydroxide ions and acid salts hydronium ions in water.

The salts of the derivatives of the invention may be formed with added cations or anions that react with anionic or cationic groups, respectively. These groups may be situated in the peptide moiety, and/or in the side chain of the derivatives of the invention.

Non-limiting examples of anionic groups of the derivatives of the invention include free carboxylic groups in the side chain, if any, as well as in the peptide moiety. The peptide moiety often includes a free carboxylic acid group at the C-terminus, and it may also include free carboxylic groups at internal acid amino acid residues such as Asp and Glu.

Non-limiting examples of cationic groups in the peptide moiety include the free amino group at the N-terminus, if present, as well as any free amino group of internal basic amino acid residues such as His, Arg, and Lys.

The ester of the derivatives of the invention may, e.g., be formed by the reaction of a free carboxylic acid group with an alcohol or a phenol, which leads to replacement of at least one hydroxyl group by an alkoxy or aryloxy group.

The ester formation may involve the free carboxylic group at the C-terminus of the peptide, and/or any free carboxylic group in the side chain.

The amide of the derivatives of the invention may, e.g., be formed by the reaction of an activated form of a free carboxylic acid group with an amine or a substituted amine, or by reaction of a free or substituted amino group with an activated form of a carboxylic acid.

The amide formation may involve the free carboxylic group at the C-terminus of the peptide, any free carboxylic group in the side chain, the free amino group at the N-terminus of the peptide, and/or any free or substituted amino group of the peptide in the peptide and/or the side chain.

In a particular embodiment, the peptide or derivative is in the form of a pharmaceutically acceptable salt. In another particular embodiment, the derivative is in the form of a pharmaceutically acceptable amide, preferably with an amide group at the C-terminus of the peptide. In a still further particular embodiment, the peptide or derivative is in the form a pharmaceutically acceptable ester.

Functional Properties

In a first aspect, the derivatives of the invention have a good potency. Also, or alternatively, in a second aspect, they have a protracted pharmacokinetic profile. Also, or alternatively, in a third aspect, they have a high oral bioavailability. Also, or alternatively, the number of mutations in the GLP-1 peptide (GLP-1 analogue) is low.

Biological Activity (Potency)

According to the first aspect, the derivatives of the invention, as well as the constituent GLP-1 peptides as such, are biologically active, or potent. In fact, the derivatives of the invention have a surprisingly good potency.

More in particular, the Chem. 3a linker element has proven to be, surprisingly and unexpectedly, superior as compared to known linker elements when it comes to biological activity or potency of the resulting end-product, the GLP-1 derivative.

For example, when a linker consisting of (Chem. 14-2xChem.6), or (Chem.14-2xChem.6a), is used instead of the "gGlu-2xOEG" (Chem. 14-2xChem. 13) linker, which is well-established in the art and has a very good reputation, the resulting GLP-1 derivatives of the present invention are, surprisingly and unexpectedly, much more potent as compared to these best-in-class state-of-the-art GLP-1 derivatives.

This seems, surprisingly and unexpectedly, to be even more pronounced when the protractor is of the Chem. 2 type, as compared to other state of the art and well-established protractors such as alpha-omega dicarboxylic acids.

In a particular embodiment, potency and/or activity refers to in vitro potency, i.e. performance in a functional GLP-1 receptor assay, more in particular to the capability of activating the human GLP-1 receptor.

The in vitro potency may, e.g., be determined in a medium containing membranes expressing the human GLP-1 receptor, and/or in an assay with whole cells expressing the human GLP-1 receptor.

For example, purified plasma membranes from a stable transfected cell line expressing the human GLP-1 receptor may be stimulated with the GLP-1 analogue or derivative in question, and the potency of cAMP production measured, e.g. based on competition between endogenously formed cAMP and exogenously added biotin-labelled cAMP, which may be captured using a specific antibody, e.g. as described in Example 20.

Also, or alternatively, the response of the human GLP-1 receptor may be measured in a reporter gene assay, e.g. in a stably transfected BHK cell line that expresses the human GLP-1 receptor and contains the DNA for the cAMP response element (CRE) coupled to a promoter and the gene for firefly luciferase (CRE luciferase). When cAMP is produced as a result of activation of the GLP-1 receptor this in turn results in the luciferase being expressed. Luciferase may be determined by adding luciferin, which by the enzyme is converted to oxyluciferin and produces bioluminescence, which is measured and is a measure of the in vitro potency. One non-limiting example of such an assay is described in Example 21.

The term half maximal effective concentration ($EC_{50}$) generally refers to the concentration which induces a response halfway between the baseline and maximum, by reference to the dose response curve. $EC_{50}$ is used as a measure of the potency of a compound and represents the concentration where 50% of its maximal effect is observed.

The in vitro potency of the derivatives of the invention may be determined as described above, and the $EC_{50}$ of the derivative in question determined. The lower the $EC_{50}$ value, the better the potency.

In a further particular embodiment, the derivative of the invention has an in vitro potency corresponding to an $EC_{50}$ at or below 10000 pM, more preferably below 5000 pM, even more preferably below 1000 pM, or most preferably below 500 pM (e.g. determined as described in Example 20. In a still further particular embodiment, the derivative of the invention has a potency corresponding to an $EC_{50}$ at 0% HSA of below 400 pM, preferably below 300 pM, more preferably below 200 pM, even more preferably below 150 pM, or most preferably below 100 pM (e.g. determined as described in Example 21).

Also, or alternatively, the ability of the derivatives of the invention to bind to the GLP-1 receptor (receptor affinity) may be measured, and, if relevant, used as a measure of the GLP-1 activity. For example, purified plasma membranes from a stable transfected cell line expressing the human GLP-1 receptor may be stimulated with the GLP-1 analogue or derivative in question, and their ability to displace of $^{125}$I-GLP-1 from the receptor measured. This may be determined, e.g., as described in Example 22. Generally, the binding to the GLP-1 receptor at low albumin concentration should be as good as possible, corresponding to a low $IC_{50}$ value. In particular embodiments, the $IC_{50}$ value of a derivative of the invention, in the presence of 0.001% HSA (low albumin), is below the corresponding $IC_{50}$ value for semaglutide, preferably below 90% thereof, more preferably below 80% thereof, even more preferably below 70% thereof, or most preferably below 50% thereof.

In another particular embodiment the derivatives of the invention are potent in vivo, which may be determined as is known in the art in any suitable animal model, as well as in clinical trials.

The diabetic db/db mouse is one example of a suitable animal model, and the blood glucose lowering effect, and/or the body weight lowering effect may be determined in such mice in vivo, for body weight lowering effect preferably after one acute administration.

The LYD pig is another example of a suitable animal model, and the reduction in food intake may be determined in a PD study in such pigs in vivo, e.g. as described in Example 25. The derivatives of the invention are very potent in vivo, which is evidenced by a nice reduction in food intake in this PD study in pigs.

Protraction—Receptor Binding/Low and High Albumin

According to the second aspect, the derivatives of the invention are protracted.

The ability of the derivatives of the invention to bind to the GLP-1 receptor in the presence of a low and a high concentration of albumin, respectively, may be determined as described in Example 22.

Generally, the binding to the GLP-1 receptor at low albumin concentration should be as good as possible, corresponding to a low $IC_{50}$ value.

The $IC_{50}$ value at high albumin concentration is a measure of the influence of albumin on the binding of the derivative to the GLP-1 receptor. As is known, the GLP-1 derivatives also bind to albumin. This is a generally desirable effect, which extends their residence in plasma. Therefore, the $IC_{50}$ value at high albumin will generally be higher than the $IC_{50}$ value at low albumin, corresponding to a reduced binding to the GLP-1 receptor, caused by albumin binding competing with the binding to the GLP-1 receptor.

Also, or alternatively, the binding of the derivatives to albumin may be measured using the assay of Example 21, which may be performed in the absence of serum albumin as well as in the presence of serum albumin. An increase of the in vitro potency, $EC_{50}$ value, in the presence of serum albumin indicates an affinity to serum albumin and represents a method to predict a protracted pharmacokinetic profile of the test substance in animal models.

Protraction—Half Life In Vivo

According to the second aspect, the derivatives of the invention are protracted.

Protraction may be determined as terminal half-life ($T_{1/2}$) in vivo in rats after i.v. administration, as described in Example 24. In particular embodiments, the half-life in rat is at least 10 hours, preferably at least 12 hours, or most preferably at least 15 hours.

Or, protraction may be determined in another animal species, for example as terminal half-life ($T_{1/2}$) in vivo in minipigs after i.v. administration, as described in Example 23. In particular embodiments, the terminal half-life in minipigs is at least 8 hours, preferably at least 24 hours, still more preferably at least 40 hours, even more preferably at least 60 hours, or most preferably at least 80 hours.

Surprisingly, the present inventors identified a novel class of GLP-1 derivatives object of the present invention, which have a high potency, and at the same time preferably a long half-life.

Oral Bioavailability

According to the third aspect, the derivatives of the invention have a high oral bioavailability.

The oral bioavailability of commercial GLP-1 derivatives is very low. The oral bioavailability of GLP-1 derivatives under development for i.v. or s.c. administration is also low.

Accordingly, there is a need in the art for GLP-1 derivatives of an improved oral bioavailability. Such derivatives could be suitable candidates for oral administration, as long as mainly their potency is generally satisfactory, and/or as long as their half-life is also generally satisfactory.

Generally, the term bioavailability refers to the fraction of an administered dose of an active pharmaceutical ingredient (API), such as a derivative of the invention that reaches the systemic circulation unchanged. By definition, when an API is administered intravenously, its bioavailability is 100%. However, when it is administered via other routes (such as orally), its bioavailability decreases (due to degradation and/or incomplete absorption and first-pass metabolism). Knowledge about bioavailability is important when calculating dosages for non-intravenous routes of administration.

Absolute oral bioavailability compares the bioavailability (estimated as the area under the curve, or AUC) of the API in systemic circulation following oral administration, with the bioavailability of the same API following intravenous administration. It is the fraction of the API absorbed through non-intravenous administration compared with the corresponding intravenous administration of the same API. The comparison must be dose normalised if different doses are used; consequently, each AUC is corrected by dividing by the corresponding dose administered.

A plasma API concentration vs time plot is made after both oral and intravenous administration. The absolute bioavailability (F) is the dose-corrected AUC-oral divided by AUC-intravenous.

In a particular embodiment, the derivative of the invention has an absolute oral bioavailability which is higher than that of semaglutide, preferably at least 10% higher, more preferably at least 20% higher, even more preferably at least 30% higher, or most preferably at least 40% higher. In additional particular embodiments, it has an absolute oral bioavailability which is at least 1.5 times that of semaglutide, preferably at least 2.0 times, more preferably at least 3.0 times, even more preferably at least 4.0 times, or most preferably at least 5.0 times that of semaglutide.

Before testing oral bioavailability the derivatives of the invention may suitably be formulated as is known in the art of oral formulations of insulinotropic compounds, e.g. using any one or more of the formulations described in WO 2008/145728.

In a particular embodiment, the derivatives of the invention have a very good gastro intestinal stability. The gastro intestinal stability may be determined in vitro, by incubation of the derivative with a suitably diluted extract from the gastro intestinal system from human beings, or from a relevant animal species such as minipig, LYD pig, dog, or rat, under physiologically relevant conditions, and for a physiologically relevant period of time. The stability may be further improved when the derivative is combined with one or more relevant enzyme inhibitors, in an effective amount. Gastro intestinal stability in vitro may be measured using standard methods known in the art. The gastro intestinal stability of the derivatives of the invention is preferably improved as compared to semaglutide, and/or as compared to the derivative of Example 2 of WO 2011/080103 A1. The derivative of the invention is preferably at least as stable as any one or both of these two comparative compounds, preferably the stability is improved by at least 10%, at least 20%, at least 30%, at least 40%, or at least 50%; more preferably by at least 75%, at least 100%, at least 150%, at least 175%, or at least 200%—as compared to the stability of any of these two comparative compounds.

Biophysical Properties

According to the fourth aspect, the derivatives of the invention have good biophysical properties. These properties include but are not limited to physical stability and/or solubility. These and other biophysical properties may be measured using standard methods known in the art of protein chemistry. In a particular embodiment, these properties are improved as compared to native GLP-1 (SEQ ID NO:1). Changed oligomeric properties of the derivatives may be at least partly responsible for the improved biophysical properties.

Additional particular embodiments of the derivatives of the invention are described in the sections headed "PARTICULAR EMBODIMENTS" and "ADDITIONAL PARTICULAR EMBODIMENTS" before the experimental section.

Production Processes

The production of peptides like GLP-1(7-37) and GLP-1 analogues is well known in the art.

The GLP-1 moiety of the derivatives of the invention, viz. GLP-1(7-37) or an analogue thereof, may for instance be produced by classical peptide synthesis, e.g., solid phase peptide synthesis using t-Boc or Fmoc chemistry or other well established techniques, see, e.g., Greene and Wuts, "Protective Groups in Organic Synthesis", John Wiley & Sons, 1999, Florencio Zaragoza Dörwald, "Organic Synthesis on solid Phase", Wiley-VCH Verlag GmbH, 2000, and "Fmoc Solid Phase Peptide Synthesis", Edited by W. C. Chan and P. D. White, Oxford University Press, 2000.

Also, or alternatively, they may be produced by recombinant methods, viz. by culturing a host cell containing a DNA sequence encoding the analogue and capable of expressing the peptide in a suitable nutrient medium under conditions permitting the expression of the peptide. Non-limiting examples of host cells suitable for expression of these peptides are: *Escherichia coli, Saccharomyces cerevisiae*, as well as mammalian BHK or CHO cell lines.

Those derivatives of the invention which include non-natural amino acids and/or a covalently attached N-terminal mono- or dipeptide mimetic may e.g. be produced as described in the experimental part. Or see e.g., Hodgson et al: "The synthesis of peptides and proteins containing non-natural amino acids", Chemical Society Reviews, vol. 33, no. 7 (2004), p. 422-430; and WO 2009/083549 A1 entitled "Semi-recombinant preparation of GLP-1 analogues".

Specific examples of methods of preparing a number of the derivatives of the invention are included in the experimental part.

Pharmaceutical Compositions

Pharmaceutical composition comprising a derivative of the invention or a pharmaceutically acceptable salt, amide, or ester thereof, and a pharmaceutically acceptable excipient may be prepared as is known in the art.

The term "excipient" broadly refers to any component other than the active therapeutic ingredient(s). The excipient may be an inert substance, an inactive substance, and/or a not medicinally active substance.

The excipient may serve various purposes, e.g. as a carrier, vehicle, diluent, tablet aid, and/or to improve administration, and/or absorption of the active substance.

The formulation of pharmaceutically active ingredients with various excipients is known in the art, see e.g. Remington: The Science and Practice of Pharmacy (e.g. 19$^{th}$ edition (1995), and any later editions).

Non-limiting examples of excipients are: Solvents, diluents, buffers, preservatives, tonicity regulating agents, chelating agents, and stabilisers.

Examples of formulations include liquid formulations, i.e. aqueous formulations, i.e. formulations comprising water. A liquid formulation may be a solution, or a suspension. An aqueous formulation typically comprises at least 50% w/w water, or at least 60%, 70%, 80%, or even at least 90% w/w of water.

Alternatively a pharmaceutical composition may be a solid formulation, e.g. a freeze-dried or spray-dried composition, which may be used as is, or whereto the physician or the patient adds solvents, and/or diluents prior to use.

The pH in an aqueous formulation may be anything between pH 3 and pH 10, for example from about 7.0 to about 9.5; or from about 3.0 to about 7.0.

A pharmaceutical composition may comprise a buffer. The buffer may e.g. be selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid, and mixtures thereof.

A pharmaceutical composition may comprise a preservative. The preservative may e.g. be selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol), and mixtures thereof. The preservative may be present in a concentration from 0.1 mg/ml to 20 mg/ml.

A pharmaceutical composition may comprise an isotonic agent. The isotonic agent may e.g. be selected from the group consisting of a salt (e.g. sodium chloride), a sugar or sugar alcohol, an amino acid (e.g. glycine, histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), and mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, alfa and beta HPCD, soluble starch, hydroxyethyl starch and carboxymethylcellulose-Na may be used. Sugar alcohol is defined as a C4-C8 hydrocarbon having at least one —OH group and includes, for example, mannitol, sorbitol, inositol, galactitol, dulcitol, xylitol, and arabitol.

A pharmaceutical composition may comprise a chelating agent. The chelating agent may e.g. be selected from salts of ethylenediaminetetraacetic acid (EDTA), citric acid, and aspartic acid, and mixtures thereof.

A pharmaceutical composition may comprise a stabiliser. The stabiliser may e.g. be one or more oxidation inhibitors, aggregation inhibitors, surfactants, and/or one or more protease inhibitors.

The term "aggregate formation" refers to a physical interaction between the polypeptide molecules resulting in formation of oligomers, which may remain soluble, or large visible aggregates that precipitate from the solution. Aggregate formation by a polypeptide during storage of a liquid pharmaceutical composition can adversely affect biological activity of that polypeptide, resulting in loss of therapeutic efficacy of the pharmaceutical composition. Furthermore, aggregate formation may cause other problems such as blockage of tubing, membranes, or pumps when the polypeptide-containing pharmaceutical composition is administered using an infusion system.

A pharmaceutical composition may comprise an amount of an amino acid base sufficient to decrease aggregate formation of the peptide during storage of the composition. The term "amino acid base" refers to one or more amino acids (such as methionine, histidine, imidazole, arginine, lysine, isoleucine, aspartic acid, tryptophan, threonine), or analogues thereof. Any amino acid may be present either in its free base form or in its salt form. Any stereoisomer (i.e., L, D, or a mixture thereof) of the amino acid base may be present.

Methionine (or other sulphuric amino acids or amino acid analogous) may be added to inhibit oxidation of methionine residues to methionine sulfoxide when the peptide is a polypeptide comprising at least one methionine residue susceptible to such oxidation. Any stereoisomer of methionine (L or D) or combinations thereof can be used.

A pharmaceutical composition may comprise a stabiliser selected from the group of high molecular weight polymers or low molecular compounds. The stabiliser may e.g. be selected from polyethylene glycol (e.g. PEG 3350), polyvinyl alcohol (PVA), polyvinylpyrrolidone, carboxy-/hydroxycellulose or derivates thereof (e.g. HPC, HPC-SL, HPC-L and HPMC), cyclodextrins, sulphur-containing substances as monothioglycerol, thioglycolic acid and 2-methylthioethanol, and different salts (e.g. sodium chloride).

A pharmaceutical composition may comprise additional stabilising agents such as, but not limited to, methionine and EDTA, which protect the polypeptide against methionine oxidation, and a nonionic surfactant, which protects the polypeptide against aggregation associated with freeze-thawing or mechanical shearing.

A pharmaceutical composition may comprise one or more surfactants, for example a surfactant, at least one surfactant, or different surfactants. The term "surfactant" refers to any molecules or ions that are comprised of a water-soluble (hydrophilic) part, and a fat-soluble (lipophilic) part. The surfactant may e.g. be selected from the group consisting of anionic surfactants, cationic surfactants, nonionic surfactants, and/or zwitterionic surfactants.

A pharmaceutical composition may comprise one or more protease inhibitors, such as, e.g., EDTA (ethylenediamine tetraacetic acid), and/or benzamidineHCl.

Additional, optional, ingredients of a pharmaceutical composition include, e.g., wetting agents, emulsifiers, antioxidants, bulking agents, metal ions, oily vehicles, proteins (e.g., human serum albumin, gelatine), and/or a zwitterion (e.g., an amino acid such as betaine, taurine, arginine, glycine, lysine and histidine).

Still further, a pharmaceutical composition may be formulated as is known in the art of oral formulations of insulinotropic compounds, e.g. using any one or more of the formulations described in WO 2008/145728.

An administered dose may contain from 0.01 mg-100 mg of the derivative, or from 0.01-50 mg, or from 0.01-20 mg, or from 0.01 mg-10 mg of the derivative.

The derivative may be administered in the form of a pharmaceutical composition. It may be administered to a patient in need thereof at several sites, for example, at topical sites such as skin or mucosal sites; at sites which bypass absorption such as in an artery, in a vein, or in the heart; and at sites which involve absorption, such as in the skin, under the skin, in a muscle, or in the abdomen.

The route of administration may be, for example, lingual; sublingual; buccal; in the mouth; oral; in the stomach; in the intestine; nasal; pulmonary, such as through the bronchioles, the alveoli, or a combination thereof; parenteral, epidermal; dermal; transdermal; conjunctival; uretal; vaginal; rectal; and/or ocular. In a particular embodiment the route of administration is per oral.

A composition may be administered in several dosage forms, for example as a solution; a suspension; an emulsion; a microemulsion; multiple emulsions; a foam; a salve; a paste; a plaster; an ointment; a tablet; a coated tablet; a chewing gum; a rinse; a capsule such as hard or soft gelatine capsules; a suppositorium; a rectal capsule; drops; a gel; a spray; a powder; an aerosol; an inhalant; eye drops; an ophthalmic ointment; an ophthalmic rinse; a vaginal pessary; a vaginal ring; a vaginal ointment; an injection solution; an in situ transforming solution such as in situ gelling, setting, precipitating, and in situ crystallisation; an infusion solution; or as an implant. A composition may further be compounded in a drug carrier or drug delivery system, e.g. in order to improve stability, bioavailability, and/or solubility. A composition may be attached to such system through covalent, hydrophobic, and/or electrostatic interactions. The purpose of such compounding may be, e.g., to decrease adverse effects, achieve chronotherapy, and/or increase patient compliance.

A composition may also be used in the formulation of controlled, sustained, protracting, retarded, and/or slow release drug delivery systems.

Parenteral administration may be performed by subcutaneous, intramuscular, intraperitoneal, or intravenous injection by means of a syringe, optionally a pen-like syringe, or by means of an infusion pump.

A composition may be administered nasally in the form of a solution, a suspension, or a powder; or it may be administered pulmonally in the form of a liquid or powder spray.

Transdermal administration is a still further option, e.g. by needle-free injection, from a patch such as an iontophoretic patch, or via a transmucosal route, e.g. buccally.

A composition may be a stabilised formulation. The term "stabilised formulation" refers to a formulation with increased physical and/or chemical stability, preferably both. In general, a formulation must be stable during use and storage (in compliance with recommended use and storage conditions) until the expiration date is reached.

The term "physical stability" refers to the tendency of the polypeptide to form biologically inactive and/or insoluble aggregates as a result of exposure to thermo-mechanical stress, and/or interaction with destabilising interfaces and surfaces (such as hydrophobic surfaces). The physical stability of an aqueous polypeptide formulation may be evaluated by means of visual inspection, and/or by turbidity measurements after exposure to mechanical/physical stress (e.g. agitation) at different temperatures for various time periods. Alternatively, the physical stability may be evaluated using a spectroscopic agent or probe of the conformational status of the polypeptide such as e.g. Thioflavin T or "hydrophobic patch" probes.

The term "chemical stability" refers to chemical (in particular covalent) changes in the polypeptide structure leading to formation of chemical degradation products potentially having a reduced biological potency, and/or increased immunogenic effect as compared to the intact polypeptide. The chemical stability can be evaluated by measuring the amount of chemical degradation products at various time-points after exposure to different environmental conditions, e.g. by SEC-HPLC, and/or RP-HPLC.

The treatment with a derivative according to the present invention may also be combined with one or more additional pharmacologically active substances, e.g. selected from antidiabetic agents, antiobesity agents, appetite regulating agents, antihypertensive agents, agents for the treatment and/or prevention of complications resulting from or associated with diabetes and agents for the treatment and/or prevention of complications and disorders resulting from or associated with obesity. Examples of these pharmacologically active substances are: Insulin, sulphonylureas, biguanides, meglitinides, glucosidase inhibitors, glucagon antagonists, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents as HMG CoA inhibitors (statins), gastric inhibitory polypeptides (GIP analogs), compounds lowering food intake, RXR agonists and agents acting on the ATP-dependent potassium channel of the β-cells; Cholestyramine, colestipol, clofibrate, gemfibrozil, lovastatin, pravastatin, simvastatin, probucol, dextrothyroxine, neteglinide, repaglinide; β-blockers such as alprenolol, atenolol, timolol, pindolol, propranolol and metoprolol, ACE (angiotensin converting enzyme) inhibitors such as benazepril, captopril, enalapril, fosinopril, lisinopril, alatriopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin; CART (cocaine amphetamine regulated transcript) agonists, NPY (neuropeptide Y) antagonists, PYY agonists, Y2 receptor agonists, Y4 receptor agonits, mixed Y2/Y4 receptor agonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, oxyntomodulin and analogues, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, RXR (retinoid X receptor) modulators, TR β agonists; histamine H3 antagonists, gastric inhibitory polypeptide agonists or antagonists, gastrin and gastrin analogs.

The treatment with a derivative according to this invention may also be combined with a surgery that influences the glucose levels, and/or lipid homeostasis such as gastric banding or gastric bypass.

Pharmaceutical Indications

The present invention also relates to a derivative of the invention for use as a medicament.

In particular embodiments, the derivative of the invention may be used for the following medical treatments, all preferably relating one way or the other to diabetes:

(i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of cognitive disorders;

(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; and/or delaying gastric emptying;

(vi) prevention and/or treatment of diabetic complications, such as neuropathy, including peripheral neuropathy; nephropathy; or retinopathy;

(vii) improving lipid parameters, such as prevention and/or treatment of dyslipidemia, lowering total serum lipids; lowering HDL; lowering small, dense LDL; lowering VLDL: lowering triglycerides; lowering cholesterol; increasing HDL; lowering plasma levels of lipoprotein a (Lp(a)) in a human; inhibiting generation of apolipoprotein a (apo(a)) in vitro and/or in vivo;

(iix) prevention and/or treatment of cardiovascular diseases, such as syndrome X; atherosclerosis; myocardial infarction; coronary heart disease; stroke, cerebral ischemia; an early cardiac or early cardiovascular disease, such as left ventricular hypertrophy; coronary artery disease; essential hypertension; acute hypertensive emergency; cardiomyopathy; heart insufficiency; exercise tolerance; chronic heart failure; arrhythmia; cardiac dysrhythmia; syncopy; atherosclerosis; mild chronic heart failure; angina pectoris; cardiac bypass reocclusion; intermittent claudication (atherosclerosis oblitterens); diastolic dysfunction; and/or systolic dysfunction;

(ix) prevention and/or treatment of gastrointestinal diseases, such as inflammatory bowel syndrome; small bowel syndrome, or Crohn's disease; dyspepsia; and/or gastric ulcers;

(x) prevention and/or treatment of critical illness, such as treatment of a critically ill patient, a critical illness polynephropathy (CIPNP) patient, and/or a potential CIPNP patient; prevention of critical illness or development of CIPNP; prevention, treatment and/or cure of systemic inflammatory response syndrome (SIRS) in a patient; and/or for the prevention or reduction of the likelihood of a patient suffering from bacteraemia, septicaemia, and/or septic shock during hospitalisation; and/or (xi) prevention and/or treatment of polycystic ovary syndrome (PCOS).

In a particular embodiment, the indication is selected from the group consisting of (i)-(iii) and (v)-(iix), such as indications (i), (ii), and/or (iii); or indication (v), indication (vi), indication (vii), and/or indication (iix).

In another particular embodiment, the indication is (i). In a further particular embodiment the indication is (v). In a still further particular embodiment the indication is (iix).

The following indications are particularly preferred: Type 2 diabetes, and/or obesity.

Particular Embodiments

The following are particular embodiments of the invention:

1. A derivative of a GLP-1 peptide, which peptide comprises a first K residue at a position corresponding to position 26 of GLP-1(7-37) (SEQ ID NO:1), a second K residue at a position corresponding to position 34 of GLP-1(7-37) (SEQ ID NO:1), and a maximum of eight amino acid changes as compared to GLP-1 (7-37), which derivative comprises two protracting moieties attached to said first and second K residue, respectively, via a linker, wherein the protracting moiety is Chem. 2:

in which y is an integer in the range of 6-13; and the linker comprises

wherein q is an integer in the range of 0-5, $R_1$ and $R_2$ independently represent *—H or *—$CH_3$, and w is an integer in the range of 0-5;

or a pharmaceutically acceptable salt, amide, or ester thereof.

2. The derivative of embodiment 1, wherein w is 0.

3. The derivative of any of embodiments 1-2, wherein the linker comprises

4. The derivative of any of embodiments 1-3, wherein q is an integer in the range of 3-5.

5. The derivative of any of embodiments 1-4, wherein q is 4.

6. The derivative of any of embodiments 1-5, wherein $R_1$ and $R_2$ are identical.

7. The derivative of any of embodiments 1-6, wherein $R_1$ and $R_2$ both represent *—H.
8. The derivative of any of embodiments 1-7, wherein the linker comprises

*—NH—$(CH_2)_q$—CH[$(CH_2)_w$—$NH_2$]—CO—*. Chem. 3:

9. The derivative of any of embodiments 1-8, wherein the linker comprises

*—NH—$(CH_2)_q$—CH($NH_2$)—CO—*. Chem. 4:

10. The derivative of any of embodiments 1-9, wherein Chem. 3a is a di-radical of lysine.
11. The derivative of any of embodiments 1-10, wherein Chem. 4a is a di-radical of lysine.
12. The derivative of any of embodiments 1-11, wherein Chem. 3 is a di-radical of lysine.
13. The derivative of any of embodiments 1-12, wherein Chem. 4 is a di-radical of lysine.
14. The derivative of any of embodiments 1-13, wherein the linker comprises

*—NH—$(CH_2)_4$—CH($NH_2$)—CO—*. Chem. 6:

15. The derivative of any of embodiments 1-14, wherein $R_1$ and $R_2$ both represent *—$CH_3$.
16. The derivative of any of embodiments 1-15, wherein Chem. 3a is a di-radical of an $N^\alpha,N^\alpha$-dimethyl lysine residue (6-amino-(S)-2-(dimethylamino)hexanoyl).
17. The derivative of any of embodiments 1-16, wherein Chem. 4a is a di-radical of lysine.
18. The derivative of any of embodiments 1-17, wherein the linker comprises

*—NH—$(CH_2)_4$—CH(N($CH_3$)$_2$)—CO—*. Chem. 6a:

19. The derivative of any of embodiments 1-18, wherein the linker comprises z times Chem. 3a, wherein z is an integer in the range of 1-2.
20. The derivative of any of embodiments 1-19, wherein the linker comprises z times Chem. 4a, wherein z is an integer in the range of 1-2.
21. The derivative of any of embodiments 1-20, wherein the linker comprises z times Chem. 3, wherein z is an integer in the range of 1-2.
22. The derivative of any of embodiments 1-21, wherein the linker comprises z times Chem. 4, wherein z is an integer in the range of 1-2.
23. The derivative of any of embodiments 1-22, wherein the linker comprises z times Chem. 6a, wherein z is an integer in the range of 1-2.
24. The derivative of any of embodiments 1-23, wherein the linker comprises z times Chem. 6, wherein z is an integer in the range of 1-2.
25. The derivative of any of embodiments 1-24, wherein z is 1.
26. The derivative of any of embodiments 1-25, wherein z is 2.
27. The derivative of any of embodiments 1-26, wherein when z is 2 the two Chem. 3a, Chem. 4a, Chem. 3, Chem. 4, Chem. 6a, or the Chem. 6 elements, respectively, are interconnected via an amide bond.
28. The derivative of any of embodiments 1-27, wherein the linker comprises

*—NH—$(CH_2)_4$—CH($NH_2$)—CO—NH—$(CH_2)_4$—CH($NH_2$)—CO—*. 2xChem. 6:

29. The derivative of any of embodiments 1-28, wherein the linker comprises

*—NH—$(CH_2)_4$—CH(N($CH_3$)$_2$)—CO—NH—$(CH_2)_4$—CH(N($CH_3$)$_2$)—CO—*. 2xChem. 6a:

30. The derivative of any of embodiments 1-29, wherein the Chem. 3a, Chem. 4a, Chem. 3, Chem. 4, Chem. 6a, Chem. 6, 2xChem. 6, or 2xChem. 6a element, respectively, is connected at its CO—* end to the epsilon amino group of the first or the second K residue of the GLP-1 peptide.
31. The derivative of any of embodiments 1-30, wherein Chem. 3a, Chem. 4a, Chem. 6, Chem. 6a, Chem. 3, Chem. 4, 2xChem. 6, or 2xChem. 6a, respectively, is a first linker element.
32. The derivative of any of embodiments 1-31, wherein the linker comprises a second linker element, Chem. 12:

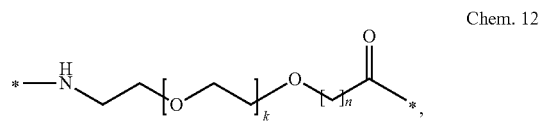
Chem. 12 wherein k is an integer in the range of 1-5, and n is an integer in the range of 1-5.
33. The derivative of embodiment 32, wherein k is 1.
34. The derivative of any of embodiments 32-33, wherein n is 1.
35. The derivative of any of embodiments 32-34, wherein the second linker element is

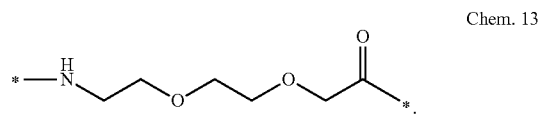
Chem. 13

36. The derivative of any of embodiments 32-35, wherein Chem. 13 is included m times, wherein m is 0, or an integer in the range of 1-2.
37. The derivative of any of embodiments 32-36, wherein m is 0.
38. The derivative of any of embodiments 32-36, wherein m is 1.
39. The derivative of any of embodiments 32-26, wherein m is 2.
40. The derivative of any of embodiments 32-39, wherein, when m is different from 1, the Chem. 13 elements are interconnected via amide bond(s).
41. The derivative of any of embodiments 1-40, wherein the linker comprises a third linker element of Chem. 14:

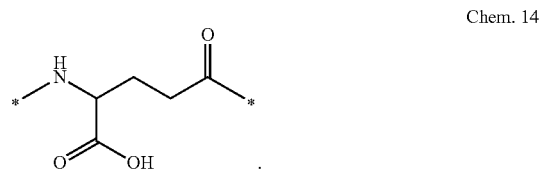
Chem. 14

42. The derivative of embodiment 41, wherein Chem. 14 is included p times, wherein p is 0, or an integer in the range of 1-3.
43. The derivative of embodiment 42, wherein p is 0.
44. The derivative of embodiment 42, wherein p is 1.
45. The derivative any of embodiments 42-44, wherein Chem. 14 is a di-radical of L-Glu.
46. The derivative of any of embodiments 42-45, wherein, when p is different from 0 and different from 1, the Chem. 14 elements are interconnected via amide bond(s).

47. The derivative of any of embodiments 1-46, wherein the linker and the protracting moiety are interconnected via an amide bond.
48. The derivative of any of embodiments 1-47, wherein the linker and the GLP-1 peptide are interconnected via an amide bond.
49. The derivative of any of embodiments 1-48, wherein the linker is attached to the epsilon-amino group of the first or the second K residue.
50. The derivative of any of embodiments 1-49, wherein the linker consists of Chem. 14 and two times Chem. 6 (Chem.14-2xChem.6), interconnected via amide bonds and in the sequence indicated, connected at its *—NH end to the CO—* end of the protracting moiety, and at its CO—* end to the epsilon amino group of the first or the second K residue of the GLP-1 peptide.
51. The derivative of any of embodiments 1-49, wherein the linker consists of Chem. 14, two times Chem. 13, and two times Chem. 6 (Chem.14-2xChem.13-2xChem.6), interconnected via amide bonds and in the sequence indicated, connected at its *—NH end to the CO—* end of the protracting moiety, and at its CO—* end to the epsilon amino group of the first or the second K residue of the GLP-1 peptide.
52. The derivative of any of embodiments 1-49, wherein the linker consists of Chem. 14, two times Chem. 13, and Chem. 6 (Chem.14-2xChem.13-Chem.6), interconnected via amide bonds and in the sequence indicated, connected at its *—NH end to the CO—* end of the protracting moiety, and at its CO—* end to the epsilon amino group of the first or the second K residue of the GLP-1 peptide.
53. The derivative of any of embodiments 1-49, wherein the linker consists of Chem. 14, and two times Chem. 6a (Chem.14-2xChem.6a), interconnected via amide bonds and in the sequence indicated, connected at its *—NH end to the CO—* end of the protracting moiety, and at its CO—* end to the epsilon amino group of the first or the second K residue of the GLP-1 peptide.
54. The derivative of any of embodiments 1-53, wherein y is an odd number.
55. The derivative of any of embodiments 1-53, wherein y is an even number.
56. The derivative of embodiment 54, wherein y is 9.
57. The derivative of embodiment 54, wherein y is 11.
58. The derivative of embodiment 55, wherein y is 10.
59. The derivative of any of embodiments 1-58, wherein Chem. 2 is represented by Chem. 2a

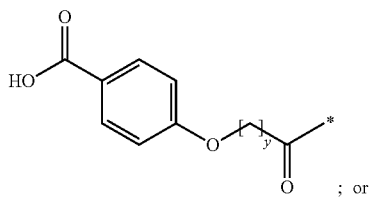

(i)

; or

Chem. 2b

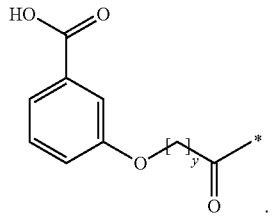

(ii)

60. The derivative of any of embodiments 1-59, wherein the two protracting moieties are substantially identical.
61. The derivative of any of embodiments 1-60, wherein the two protracting moieties have a similarity of at least 0.5; preferably at least 0.6; more preferably at least 0.7, or at least 0.8; even more preferably at least 0.9; or most preferably at least 0.99, such as a similarity of 1.0.
62. The derivative of any of embodiments 1-61, wherein the two linkers are substantially identical.
63. The derivative of any of embodiments 1-62, wherein the two linkers have a similarity of at least 0.5; preferably at least 0.6; more preferably at least 0.7, or at least 0.8; even more preferably at least 0.9; or most preferably at least 0.99, such as a similarity of 1.0.
64. The derivative of any of embodiments 1-83, wherein the two side chains consisting of protracting moiety and linker are substantially identical.
65. The derivative of any of embodiments 1-64, wherein the two side chains consisting of protracting moiety and linker have a similarity of at least 0.5; preferably at least 0.6; more preferably at least 0.7, or at least 0.8; even more preferably at least 0.9; or most preferably at least 0.99, such as a similarity of 1.0.
66. The derivative of any of embodiments 60-65, wherein the two chemical structures to be compared are represented as fingerprints, such as a) ECFP_6 fingerprints; b) UNITY fingerprints; and/or c) MDL fingerprints; and wherein for each of a), b) and c) the Tanimoto coefficient is preferably used for calculating the similarity of the two fingerprints.
67. The derivative of any of embodiments 1-66, wherein the first K residue is designated $K^{26}$.
68. The derivative of any of embodiments 1-67, wherein the second K residue is designated $K^{34}$.
69. The derivative of any of embodiments 1-68, wherein the position corresponding to position 26 of GLP-1(7-37) (SEQ ID NO:1) is identified by handwriting and eyeballing.
70. The derivative of any of embodiments 1-69, wherein the position corresponding to position 34 of GLP-1(7-37) (SEQ ID NO:1) is identified by handwriting and eyeballing.
71. The derivative of any of embodiments 1-70, wherein the number of amino acid changes as compared to GLP-1(7-37) (SEQ ID NO:1) are identified by handwriting and eyeballing.
72. The derivative of any of embodiments 1-71, wherein the position corresponding to position 26 of GLP-1(7-37) (SEQ ID NO:1) is identified by use of a standard protein or peptide alignment program.
73. The derivative of any of embodiments 1-72, wherein the position corresponding to position 34 of GLP-1(7-37) (SEQ ID NO:1) is identified by use of a standard protein or peptide alignment program.

74. The derivative of any of embodiments 1-73, wherein the number of amino acid changes as compared to GLP-1(7-37) (SEQ ID NO:1) are identified by use of a standard protein or peptide alignment program.
75. The derivative of any of embodiments 72-74, wherein the alignment program is a Needleman-Wunsch alignment.
76. The derivative of any of embodiments 72-75, wherein the default scoring matrix and the default identity matrix is used.
77. The derivative of any of embodiments 72-76, wherein the scoring matrix is BLOSUM62.
78. The derivative of any of embodiments 72-77, wherein the penalty for the first residue in a gap is −10 (minus ten).
79. The derivative of any of embodiments 72-78, wherein the penalties for additional residues in a gap is −0.5 (minus point five).
80. The derivative of any of embodiments 1-79, wherein the peptide comprises no K residues other than the first and the second K residue.
81. The derivative of any of embodiments 1-80, wherein the peptide is GLP-1(7-37) (SEQ ID NO:1).
82. The derivative of any of embodiments 1-80, wherein the peptide is an analogue of GLP-1(7-37) (SEQ ID NO:1).
83. The derivative of embodiment 82, wherein the amino acid change(s) is (are) at one or more positions corresponding to the following positions in GLP-1(7-37) (SEQ ID NO:1): Position 7, 8, 22, and/or 30.
84. The derivative of any of embodiments 82-83, wherein the analogue comprises at least one of the following changes: $Imp^7$, $Aib^8$, $E^{22}$, and/or $E^{30}$.
85. The derivative of any of embodiments 82-84, wherein the analogue comprises $Imp^7$.
86. The derivative of any of embodiments 82-85, wherein the analogue comprises $Aib^8$.
87. The derivative of any of embodiments 82-86, wherein the analogue comprises $E^{22}$.
88. The derivative of any of embodiments 82-86, wherein the analogue does not comprise $E^{22}$.
89. The derivative of any of embodiments 82-88, wherein the analogue comprises $E^{30}$.
90. The derivative of any of embodiments 1-89, wherein, for determination of the changes in the peptide, the amino acid sequence of the peptide is compared to the amino acid sequence of native GLP-1(7-37) (SEQ ID NO:1).
91. The derivative of any of embodiments 1-90, wherein, for determination of a position in a peptide which corresponds to a specified position in native GLP-1(7-37) (SEQ ID NO:1), the amino acid sequence of the peptide is compared to the amino acid sequence of native GLP-1(7-37) (SEQ ID NO:1).
92. The derivative of any of embodiments 1-91, wherein the comparison of the amino acid sequence of the peptide with that of GLP-1(7-37) (SEQ ID NO:1) is done by handwriting and eyeballing.
93. The derivative of any of embodiments 1-92, wherein the comparison of the amino acid sequence of the peptide with that of GLP-1(7-37) (SEQ ID NO:1) is done by use of a standard protein or peptide alignment program.
94. The derivative of embodiment 93, wherein the alignment program is a Needleman-Wunsch alignment.
95. The derivative of any of embodiments 93-94, wherein the default scoring matrix and the default identity matrix is used.
96. The derivative of any of embodiments 93-95, wherein the scoring matrix is BLOSUM62.
97. The derivative of any of embodiments 93-96, wherein the penalty for the first residue in a gap is −10 (minus ten).
98. The derivative of any of embodiments 93-97, wherein the penalties for additional residues in a gap is −0.5 (minus point five).
99. The derivative of any of embodiments 93-98, wherein the position corresponding to any of the indicated positions of GLP-1(7-37) (SEQ ID NO:1) is identified by handwriting and eyeballing.
100. The derivative of any of embodiments 93-99, wherein the position corresponding to any of the indicated positions of GLP-1(7-37) (SEQ ID NO:1) is identified as described for position 26 and position 34 in any of embodiments 55-62.
101. The derivative of any of embodiments 1-100, wherein the peptide has a maximum of three amino acid changes.
102. The derivative of any of embodiments 1-101, wherein the peptide has a maximum of two amino acid changes.
103. The derivative of any of embodiments 1-102, wherein the peptide has a maximum of one amino acid change.
104. The derivative of any of embodiments 1-103, wherein the peptide has 0 (zero) amino acid changes.
105. The derivative of any of embodiments 1-104, wherein the peptide has a minimum of one amino acid modification.
106. The derivative of any of embodiments 1-105, wherein the peptide has a minimum of two amino acid changes.
107. The derivative of any of embodiments 1-106, wherein the peptide has a minimum of three amino acid changes.
108. The derivative of any of embodiments 1-107, wherein the peptide has one amino acid change.
109. The derivative of any of embodiments 1-108, wherein the peptide has two amino acid changes.
110. The derivative of any of embodiments 1-109, wherein the peptide has three amino acid changes.
111. The derivative of any of embodiments 1-110, wherein the changes, if any, are substitutions.
112. The derivative of any of embodiments 1-111, wherein the analogue a) comprises a GLP-1 analogue of Formula I; and/or b) is a GLP-1 analogue of Formula I:

$Xaa_7$-$Xaa_8$-Glu-Gly-Thr-$Xaa_{12}$-Thr-Ser-Asp-$Xaa_{16}$-Ser-$Xaa_{18}$-$Xaa_{19}$-$Xaa_{20}$-Glu-$Xaa_{22}$-$Xaa_{23}$-Ala-$Xaa_{25}$-Lys-$Xaa_{27}$-Phe-Ile-$Xaa_{30}$-$Xaa_{31}$-Leu-$Xaa_{33}$-Lys-$Xaa_{35}$-$Xaa_{36}$-$Xaa_{37}$-$Xaa_{38}$,(SEQ ID NO: 3)   Formula I wherein $Xaa_7$ is L-histidine, imidazopropionyl (Imp), α-hydroxy-histidine, D-histidine, desamino-histidine (desH), 2-amino-histidine, β-hydroxy-histidine, homohistidine, $N^\alpha$-acetyl-histidine, $N^\alpha$-formyl-histidine, α-fluoromethyl-histidine, α-methyl-histidine, 3-pyridylalanine, 2-pyridylalanine, or 4-pyridylalanine;

$Xaa_8$ is Ala, Gly, Val, Leu, Ile, Thr, Ser, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;

$Xaa_{12}$ is Phe or Leu;
$Xaa_{16}$ is Val or Leu;
$Xaa_{18}$ is Ser, Val, or Leu;
$Xaa_{19}$ is Tyr or Gln;
$Xaa_{20}$ is Leu or Met;
$Xaa_{22}$ is Gly, Glu, or Aib;
$Xaa_{23}$ is Gln, Glu, or Arg;
$Xaa_{25}$ is Ala or Val;
$Xaa_{27}$ is Glu or Leu;
$Xaa_{30}$ is Ala, Glu, or Arg;

Xaa$_{31}$ is Trp or His
Xaa$_{33}$ is Val;
Xaa$_{35}$ is Gly or Aib;
Xaa$_{36}$ is Arg or Gly;
Xaa$_{37}$ is Gly or Arg; and
Xaa$_{38}$ is Ser, Gly, Ala, Glu, Pro, Arg, or absent.

113. The derivative of embodiment 112, wherein the peptide of Formula I is an analogue of GLP-1(7-37) (SEQ ID NO:1).
114. The derivative of embodiment 112, wherein the peptide of Formula I is GLP-1(7-37) (SEQ ID NO:1).
115. The derivative of any of embodiments 112-114, wherein Xaa$_7$ is His or Imp (desH); Xaa$_8$ is Ala or Aib; Xaa$_{12}$ is Phe; Xaa$_{16}$ is Val; Xaa$_{18}$ is Ser; Xaa$_{19}$ is Tyr; Xaa$_{20}$ is Leu; Xaa$_{22}$ is Gly or Glu; Xaa$_{23}$ is Gln; Xaa$_{25}$ is Ala; Xaa$_{27}$ is Glu; Xaa$_{30}$ is Ala or Glu; Xaa$_{31}$ is Trp; Xaa$_{33}$ is Val; Xaa$_{34}$ is Gln; Xaa$_{35}$ is Gly; Xaa$_{36}$ is Arg; Xaa$_{37}$ is Gly; and Xaa$_{38}$ is absent.
116. The derivative of any of embodiments 112-115, wherein Xaa$_7$ is His.
117. The derivative of any of embodiments 112-115, wherein Xaa$_7$ is Imp.
118. The derivative of any of embodiments 112-117, wherein Xaa$_8$ is Ala.
119. The derivative of any of embodiments 112-117, wherein Xaa$_8$ is Aib.
120. The derivative of any of embodiments 112-119, wherein Xaa$_{12}$ is Phe.
121. The derivative of any of embodiments 112-120, wherein Xaa$_{16}$ is Val.
122. The derivative of any of embodiments 112-121, wherein Xaa$_{18}$ is Ser.
123. The derivative of any of embodiments 112-122, wherein Xaa$_{19}$ is Tyr.
124. The derivative of any of embodiments 112-123, wherein Xaa$_{20}$ is Leu.
125. The derivative of any of embodiments 112-124, wherein Xaa$_{22}$ is Gly.
126. The derivative of any of embodiments 112-124, wherein Xaa$_{22}$ is Glu.
127. The derivative of any of embodiments 112-124, wherein Xaa$_{22}$ is not Glu.
128. The derivative of any of embodiments 112-127, wherein Xaa$_{23}$ is Gln.
129. The derivative of any of embodiments 112-128, wherein Xaa$_{25}$ is Ala.
130. The derivative of any of embodiments 112-129, wherein Xaa$_{27}$ is Glu.
131. The derivative of any of embodiments 112-130, wherein Xaa$_{30}$ is Ala.
132. The derivative of any of embodiments 112-130, wherein Xaa$_{30}$ is Glu.
133. The derivative of any of embodiments 112-132, wherein Xaa$_{31}$ is Trp.
134. The derivative of any of embodiments 112-133, wherein Xaa$_{33}$ is Val.
135. The derivative of any of embodiments 112-134, wherein Xaa$_{35}$ is Gly.
136. The derivative of any of embodiments 112-135, wherein Xaa$_{36}$ is Arg.
137. The derivative of any of embodiments 112-136, wherein Xaa$_{37}$ is Gly.
138. The derivative of any of embodiments 112-137, wherein Xaa$_{38}$ is absent.
139. The derivative of any of embodiments 1-138, wherein the peptide comprises the following amino acid changes, as compared to GLP-1(7-37) (SEQ ID NO:1):
(i) 8Aib; (ii) 7Imp, 8Aib; (iii) 8Aib, 22E; or (iv) 8Aib, 22E, 30E.
140. The derivative of any of embodiments 1-139, wherein the peptide has the following amino acid changes, as compared to GLP-1(7-37) (SEQ ID NO:1):
(i) 8Aib; (ii) 7Imp, 8Aib; (iii) 8Aib, 22E; or (iv) 8Aib, 22E, 30E.
141. A compound, preferably according to any of embodiments 1-140, selected from the following: Chem. 21, Chem. 22, Chem. 23, Chem. 24, Chem. 25, Chem. 26, Chem. 27, Chem. 28, Chem. 29, Chem. 30, Chem. 31, Chem. 32, Chem. 33, Chem. 34, Chem. 35, Chem. 36, Chem. 37, and Chem. 38; or a pharmaceutically acceptable salt, amide, or ester thereof.
142. A compound, preferably a compound of embodiment 141, characterised by its name, and selected from a listing of each of the names of the compounds of Examples 1-18 herein; or a pharmaceutically acceptable salt, amide, or ester thereof.
143. The derivative of any of embodiments 1-142, which has GLP-1 activity.
144. The derivative of embodiment 143, wherein GLP-1 activity refers to the capability of activating the human GLP-1 receptor.
145. The derivative of embodiment 144, wherein activation of the human GLP-1 receptor is measured in an in vitro assay, as the potency of cAMP production.
146. The derivative of any of embodiments 1-145, which has a potency corresponding to an EC$_{50}$
a) below 10000 pM, preferably below 8000 pM, more preferably below 5000 pM, even more preferably below 4000 pM, or most preferably below 3000 pM;
b) below 2000 pM, preferably below 1200 pM, more preferably below 1000 pM, even more preferably below 800 pM, or most preferably below 600 pM;
c) below 400 pM, preferably below 300 pM, more preferably below 200 pM, even more preferably below 150 pM, or most preferably below 100 pM; or
d) below 80 pM, preferably below 60 pM, more preferably below 50 pM, even more preferably below 40 pM, or most preferably below 30 pM.
147. The derivative of embodiment 146, wherein the potency is determined as EC$_{50}$ for stimulation of the formation of cAMP in a medium containing the human GLP-1 receptor, such as a medium of the following composition (final in-assay concentrations) 50 mM TRIS-HCl; 5 mM HEPES; 10 mM MgCl$_2$, 6H$_2$O; 150 mM NaCl; 0.01% Tween; 0.1% BSA; 0.5 mM IBMX; 1 mM ATP; 1 uM GTP, preferably using a stable transfected cell-line such as BHK467-12A (tk-ts13), and/or using for the determination of cAMP a functional receptor assay, e.g. based on competition between endogenously formed cAMP and exogenously added biotin-labelled cAMP, in which assay cAMP is more preferably captured using a specific antibody, and/or wherein an even more preferred assay is the AlphaScreen cAMP Assay, most preferably the one described in Example 20.
148. The derivative of any of embodiments 144-145, wherein activation of the human GLP-1 receptor is measured in an in vitro assay, in a reporter gene assay.
149. The derivative of embodiment 148, wherein the assay is performed in a stably transfected BHK cell line that expresses the human GLP-1 receptor and contains the DNA for the cAMP response element (CRE) coupled to a promoter and the gene for firefly luciferase (CRE luciferase).

150. The derivative of embodiment 149, wherein when assay incubation is completed luciferin is added and luminescence is measured.
151. The derivative of any of embodiments 148-150, wherein the assay is performed in the absence of serum albumin (0% HSA, final assay concentration).
152. The derivative of any of embodiments 148-151, wherein the assay is performed in the presence of 1% serum albumin (HSA, final assay concentration).
153. The derivative of any of embodiments 148-152, wherein the cells are BHK cells with BHK-ts13 as a parent cell line.
154. The derivative of any of embodiments 148-153, wherein the cells are derived from clone FCW467-12A.
155. The derivative of any of embodiments 148-154, wherein the cells are cultured at 5% $CO_2$ in cell culture medium, aliquoted and stored in liquid nitrogen.
156. The derivative of embodiment 155, wherein the cell culture medium is 10% FBS (Fetal Bovine Serum), 1 mg/ml G418, 240 nM MTX (methotrexate) and 1% pen/strep (penicillin/streptomycin).
157. The derivative of any of embodiments 148-156, wherein before each assay a cell culture aliquot is taken up and washed twice in PBS before being suspended at the desired concentration in assay buffer.
158. The derivative of any of embodiments 148-157, wherein for 96-well plates the suspension is made to give a final concentration of $5 \times 10^3$ cells/well.
159. The derivative of any of embodiments 157-158, wherein the assay buffer is 1% assay buffer, which consists of 2% ovalbumin, 0.2% Pluronic F-68 and 2% HSA in assay medium.
160. The derivative of any of embodiments 157-158, wherein the assay buffer is 0% assay buffer, which consists of 2% ovalbumin and 0.2% Pluronic F-68 in assay medium.
161. The derivative of any of embodiments 159-160, wherein assay medium consists of DMEM w/o phenol red, 10 mM Hepes and 1× Glutamax.
162. The derivative of any of embodiments 148-161, wherein the assay procedure comprises the following steps:
i) Cell stocks are thawed in a 37° C. water bath;
ii) cells are washed three times in PBS;
iii) the cells are counted and adjusted to $5 \times 10^3$ cells/50 µl ($1 \times 10^5$ cells/ml) in assay medium, and a 50 µl aliquot of cells is transferred to each well in the assay plate;
iv) stocks of the test compounds and reference compounds, if any, are diluted to a concentration of 0.2 µM in either 0% assay buffer for the 0% HSA assay or 1% assay buffer for the 1% HSA assay; and compounds are diluted 10-fold to give a suitable range of concentrations (such as: $2 \times 10^{-7}$ M, $2 \times 10^{-8}$ M; $2 \times 10^{-9}$ M, $2 \times 10^{-10}$ M, $2 \times 10^{-11}$ M, $2 \times 10^{-12}$ M and $2 \times 10^{-13}$ M), and for each compound a blank assay buffer control is also included;
v) a 50 µl aliquot of compound or blank is transferred in triplicate from the dilution plate to the assay plate, and compounds are tested at suitable concentrations (such as the following final concentrations: $1 \times 10^{-7}$ M, $1 \times 10^{-8}$ M; $1 \times 10^{-9}$ M, $1 \times 10^{-10}$ M, $1 \times 10^{-11}$ M, $1 \times 10^{-12}$ M and $1 \times 10^{-13}$ M);
vi) the assay plate is incubated for 3 h in a 5% $CO_2$ incubator at 37° C.;
vii) the assay plate is removed from the incubator and allowed to stand at room temperature for 15 min;
ixx) a 100 µl aliquot of luciferin (such as steadylite plus reagent) is added to each well of the assay plate;
ix) each assay plate is covered to protect it from light and shaken for 30 min at room temperature; and
x) each assay plate is read, for example in a Packard TopCount NXT instrument.
163. The derivative of embodiment 162, wherein the data from the TopCount instrument are transferred to Graph-Pad Prism 5 software for desired calculations.
164. The derivative of any of embodiments 148-163, wherein values for each triplicate is averaged, a non-linear regression performed, and the $EC_{50}$ values calculated.
165. The derivative of any of embodiments 162-164, wherein the regression is (log(agonist) vs response-Variable slope (four parameter)).
166. The derivative of any of embodiments 144-145, wherein the potency is determined as described in any of embodiments 148-165.
167. The derivative of embodiment 166, wherein the potency is determined as described in Example 21.
168. The derivative of any of embodiments 143-167, which has a potency corresponding to an $EC_{50}$ at 0% HSA of
a) below 400 pM, preferably below 300 pM, more preferably below 200 pM, even more preferably below 150 pM, or most preferably below 100 pM;
b) below 80 pM, preferably below 60 pM, more preferably below 50 pM, even more preferably below 40 pM, or most preferably below 30 pM; or
c) below 25 pM, preferably below 20 pM, more preferably below 15 pM, even more preferably below 10 pM, or most preferably below 8.0 pM.
169. The derivative of any of embodiments 148-168, the $EC_{50}$ value of which is no more than 20 times the $EC_{50}$ value for semaglutide.
170. The derivative of any of embodiments 148-169, the $EC_{50}$ value of which is no more than 15 times the $EC_{50}$ value for semaglutide.
171. The derivative of any of embodiments 148-170, the $EC_{50}$ value of which is no more than 10 times the $EC_{50}$ value for semaglutide.
172. The derivative of any of embodiments 148-171, the $EC_{50}$ value of which is no more than 5 times the $EC_{50}$ value for semaglutide.
173. The derivative of any of embodiments 148-172, the $EC_{50}$ value of which is no more than 2.5 times the $EC_{50}$ value for semaglutide.
174. The derivative of any of embodiments 148-173, the $EC_{50}$ value of which is lower than the $EC_{50}$ value for semaglutide.
175. The derivative of any of embodiments 148-174, the $EC_{50}$ value of which is less than 0.75 times the $EC_{50}$ value for semaglutide.
176. The derivative of any of embodiments 148-175, the $EC_{50}$ value of which is less than 0.50 times the $EC_{50}$ value for semaglutide.
177. The derivative of any of embodiments 1-176, for which the GLP-1 receptor binding affinity ($IC_{50}$) in the presence of approximately 0.001% HSA (low albumin) is
a) below 500 nM, preferably below 250 nM, more preferably below 100 nM, or most preferably below 50 nM;
b) below 12 nM, preferably below 10 nM, more preferably below 8.0 nM, still more preferably below 6.0 nM, even more preferably below 5.0 nM, or most preferably below 3.0 nM;
c) below 2.0 nM, preferably below 1.0 nM, even more preferably below 0.80 nM, or most preferably below 0.60 nM; or d) below 0.40 nM, preferably below 0.30 nM, even more preferably below 0.20 nM, or most preferably below 0.10 nM.
178. The derivative of embodiment 144, wherein activation of the human GLP-1 receptor is measured as GLP-1 receptor binding affinity ($IC_{50}$) in the presence of approximately 0.001% HSA (low albumin).
179. The derivative of any of embodiments 1-178, for which the GLP-1 receptor binding affinity ($IC_{50}$) in the presence of 2.0% HSA (high albumin) is
a) below 1000 nM, preferably below 900 nM, more preferably below 800 nM;
b) below 700 nM, preferably below 500 nM, more preferably below 300 nM; or
c) below 200 nM, preferably below 100 nM, or more preferably below 50 nM.
180. The derivative of any of embodiments 177-179, wherein the binding affinity to the GLP-1 receptor is measured by way of displacement of $^{125}$I-GLP-1 from the receptor, preferably using a SPA binding assay.
181. The derivative of any of embodiments 177-180, wherein the GLP-1 receptor is prepared using a stable, transfected cell line, preferably a hamster cell line, more preferably a baby hamster kidney cell line, such as BHK tk-ts13.
182. The derivative of any of embodiments 177-181, wherein the $IC_{50}$ value is determined as the concentration which displaces 50% of $^{125}$I-GLP-1 from the receptor.
183. The derivative of any of embodiments 177-182, wherein the GLP-1 receptor binding affinity ($IC_{50}$) is determined as described in Example 22.
184. The derivative of any of embodiments 1-183, which has an oral bioavailability, preferably an absolute oral bioavailability, which is higher than that of semaglutide.
185. The derivative of any of embodiments 1-184, which has an oral bioavailability, preferably an absolute oral bioavailability, which is higher than that of liraglutide.
186. The derivative of any of embodiments 1-185, wherein the derivative is effective at lowering blood glucose in vivo in db/db mice.
187. The derivative of any of embodiments 1-186, wherein the derivative is effective at lowering body weight in vivo in db/db mice.
188. The derivative of any of embodiments 1-187 which, in a PD study in pigs, reduces food intake on day 1, 2, 3, and/or 4 after s.c. administration of a single dose of the derivative, as compared to a vehicle-treated control group.
189. The derivative of embodiment 188 wherein the dose is 0.3, 1, 3, 10 or 30 nmol/kg; preferably 3.0 nmol/kg.
190. The derivative of any of embodiments 188-189, wherein the food intake on day 1 is 80% or lower, preferably 60% or lower, more preferably 50% or lower, or most preferably 40% or lower, wherein the percentage is relative to the food intake of the control group.
191. The derivative of any of embodiments 188-190, wherein the food intake on day 2 is 80% or lower, preferably 60% or lower, or more preferably 40% or lower, wherein the percentage is relative to the food intake of the control group.
192. The derivative of any of embodiments 188-191, wherein the study is conducted and the data compiled and analysed as described in Example 25.
193. The derivative of any of embodiments 1-192, which has a more protracted profile of action than liraglutide.
194. The derivative of embodiment 193, wherein protraction means half-life in vivo in a relevant animal species, such as db/db mice, rat, pig, and/or, preferably, minipig; wherein the derivative is administered i) s.c., and/or, ii) i.v.; preferably ii) i.v.
195. The derivative of any of embodiments 1-194, wherein the terminal half-life ($T_{1/2}$) after i.v. administration in rat is higher than that of semaglutide.
196. The derivative of any of embodiments 1-195, wherein the terminal half-life ($T_{1/2}$) after i.v. administration in rat is at least a) 25% higher, b) 50% higher, c) 75% higher, d) 100% higher (=twice), or e) 150% higher than the terminal half-life of semaglutide.
197. The derivative of any of embodiments 1-196, wherein the terminal half-life ($T_{1/2}$) after i.v. administration in rat is at least two times, preferably at least 2½ times, the terminal half-life of semaglutide.
198. The derivative of any of embodiments 193-197, wherein the half-life is determined in in vivo pharmacokinetic studies in rat, for example as described in Example 24.
199. The derivative of any of embodiments 1-198, wherein the terminal half-life ($T_{1/2}$) after i.v. administration in minipigs is
a) at least 8 hours, preferably at least 16 hours, more preferably at least 24 hours, even more preferably at least 32 hours, or most preferably at least 40 hours;
b) at least 50 hours, preferably at least 55 hours, more preferably at least 60 hours, or even more preferably at least 65 hours; or
c) at least 70 hours, preferably at least 75 hours, more preferably at least 80 hours, still more preferably at least 85 hours, or even more preferably at least 90 hours.
200. The derivative of embodiment 199, wherein the minipigs are male Göttingen minipigs.
201. The derivative of any of embodiments 199-200, wherein the minipigs are 7-14 months of age, and preferably weighing from 16-35 kg.
202. The derivative of any of embodiments 199-201, wherein the minipigs are housed individually, and fed once or twice daily, preferably with SDS minipig diet.
203. The derivative of any of embodiments 199-202, wherein the derivative is dosed, i.v., after at least 2 weeks of acclimatisation.
204. The derivative of any of embodiments 199-203, wherein the animals are fasted for approximately 18 h before dosing and from 0 to 4 h after dosing, and have ad libitum access to water during the whole period.
205. The derivative of any of embodiments 199-204, wherein the GLP-1 derivative is dissolved in 50 mM sodium phosphate, 145 mM sodium chloride, 0.05% tween 80, pH 7.4 to a suitable concentration, preferably from 20-60 nmol/ml.
206. The derivative of any of embodiments 199-205, wherein intravenous injections of the derivative are given in a volume corresponding to 1-2 nmol/kg.
207. The derivative of any of embodiments 199-206, wherein the terminal half-life ($T_{1/2}$) is determined in in vivo pharmacokinetic studies in minipig, for example as described in Example 23.208. An intermediate product in the form of a GLP-1 analogue selected from the following analogues of GLP-1(7-37) (SEQ ID NO:1): (i) 8aib; (ii) 7Imp, 8Aib; (iii) 8Aib, 22E; or (iv) 8Aib, 22E, 30E or a pharmaceutically acceptable salt, amide, or ester of any of the analogues of (i), (ii), (iii), or (iv).
209. The analogue of embodiment 208, wherein the comparison with GLP-1(7-37) (SEQ ID NO:1) is made by handwriting and eyeballing.

210. The analogue of any of embodiments 208-209, wherein the comparison with GLP-1(7-37) (SEQ ID NO:1) is made by use of a standard protein or peptide alignment program.
211. The analogue of embodiment 210, wherein the alignment program is a Needleman-Wunsch alignment.
212. The analogue of any of embodiments 208-211, wherein the default scoring matrix and the default identity matrix is used.
213. The analogue of any of embodiments 208-212, wherein the scoring matrix is BLOSUM62.
214. The analogue of any of embodiments 208-213, wherein the penalty for the first residue in a gap is −10 (minus ten).
215. The analogue of any of embodiments 208-214, wherein the penalties for additional residues in a gap is −0.5 (minus point five).
216. A compound selected from (S)-2-Dimethylamino-6-(9H-fluoren-9-ylmethoxycarbonylamino)-hexanoic acid; and

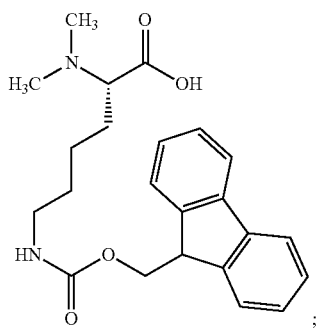

Chem. 39 or a pharmaceutically acceptable salt, amide, or ester thereof.
217. A derivative according to any of embodiments 1-207, or an analogue according to any of embodiments 208-215, for use as a medicament.
218. A derivative according to any of embodiments 1-207, or an analogue according to any of embodiments 208-215, for use in the treatment and/or prevention of all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression.
219. Use of a derivative according to any of embodiments 1-207, or an analogue according to any of embodiments 208-215, in the manufacture of a medicament for the treatment and/or prevention of all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression.
220. A method for treating or preventing all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression—by administering a pharmaceutically active amount of a derivative according to any of embodiments 1-207, or an analogue according to any of embodiments 208-215.

The invention also relates to a derivative of a GLP-1 analogue, which analogue comprises a first K residue at a position corresponding to position 26 of GLP-1(7-37) (SEQ ID NO:1), a second K residue at a position corresponding to position 34 of GLP-1(7-37) (SEQ ID NO:1), and a maximum of eight amino acid changes as compared to GLP-1 (7-37), which derivative comprises a first and a second protracting moiety attached to said first and second K residue, respectively, via a first and a second linker, respectively, wherein the first and the second protracting moiety is Chem. 2:

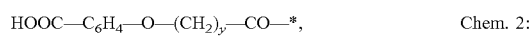

in which y is an integer in the range of 6-13; and the first and the second linker comprises

wherein q is an integer in the range of 0-5, $R_1$ and $R_2$ independently represent *—H (a hydrogen radical) or *—$CH_3$ (methyl), and w is an integer in the range of 0-5; or a pharmaceutically acceptable salt, amide, or ester thereof; as well as any of the above embodiments 2-220 appended hereto as dependent embodiments.

Additional Particular Embodiments

The following are additional particular embodiments of the invention:
1. A derivative of a GLP-1 peptide,
   which peptide comprises a first K residue at a position corresponding to position 26 of GLP-1(7-37) (SEQ ID NO:1), a second K residue at a position corresponding to position 34 of GLP-1(7-37) (SEQ ID NO:1), and a maximum of eight amino acid changes as compared to GLP-1 (7-37),
   which derivative comprises two protracting moieties attached to said first and second K residue, respectively, via a linker, wherein
   the protracting moiety is Chem. 2:

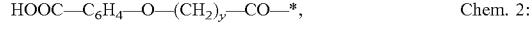

in which y is an integer in the range of 6-13; and the linker comprises

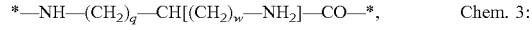

wherein q is an integer in the range of 0-5, and w is an integer in the range of 0-5;
or a pharmaceutically acceptable salt, amide, or ester thereof.
2. The derivative of embodiment 1, wherein Chem. 3 is connected at its CO—* end to the epsilon amino group of the first or the second K residue of the GLP-1 peptide.
3. The derivative of any of embodiments 1-2, wherein the linker comprises z times Chem. 3, wherein z is an integer in the range of 1-2.
4. The derivative of embodiment 3, wherein z is 1.
5. The derivative of embodiment 3, wherein z is 2.
6. The derivative of any of embodiments 3 and 5, wherein when z is 2 the Chem. 3 elements are interconnected via an amide bond.
7. The derivative of any of embodiments 1-6, wherein w is 0.
8. The derivative of any of embodiments 1-7, wherein q is 4.

9. The derivative of any of embodiments 1-8, wherein the linker comprises

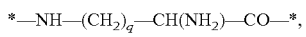 Chem. 4:

wherein q is an integer in the range of 3-5.
10. The derivative of any of embodiments 1-9, wherein q is 4.
11. The derivative of any of embodiments 1-10, wherein Chem. 3, or Chem. 4, respectively, is a di-radical of lysine.
12. The derivative of any of embodiments 1-11, wherein the linker comprises

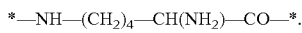 Chem. 6:

13. The derivative of any of embodiments 1-12, wherein the linker comprises

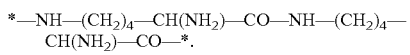 2xChem. 6:

14. The derivative of any of embodiments 1-13, wherein Chem. 3, Chem. 4, Chem. 6, or 2xChem. 6, respectively, is a first linker element.
15. The derivative of any of embodiments 1-14, wherein the linker comprises a second linker element, Chem. 12:

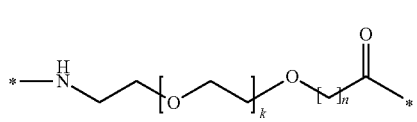 Chem. 12 wherein k is an integer in the range of 1-5, and n is an integer in the range of 1-5.
16. The derivative of embodiment 15, wherein k is 1.
17. The derivative of any of embodiments 15-16, wherein n is 1.
18. The derivative of any of embodiments 15-17, wherein the second linker element is

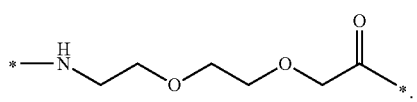 Chem. 13

19. The derivative of any of embodiments 15-18, wherein Chem. 13 is included m times, wherein m is 0, or an integer in the range of 1-2.
20. The derivative of embodiment 10, wherein m is 0, 1, or 2.
21. The derivative of any of embodiments 19-20, wherein m is 0.
22. The derivative of any of embodiments 19-20, wherein m is 1.
23. The derivative of any of embodiments 19-20, wherein m is 2.
24. The derivative of any of embodiments 19-23, wherein, when m is different from 1, the Chem. 13 elements are interconnected via amide bond(s).
25. The derivative of any of embodiments 1-24, wherein the linker comprises a third linker element of Chem. 14:

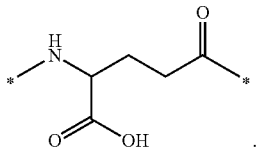 Chem. 14

26. The derivative of embodiment 25, wherein Chem. 14 is included p times, wherein p is 0, or an integer in the range of 1-3.
27. The derivative of embodiment 25, wherein p is 0.
28. The derivative of embodiment 25, wherein p is 1.
29. The derivative any of embodiments 25-28, wherein Chem. 14 is a di-radical of L-Glu.
30. The derivative of any of embodiments 25-29, wherein, when p is different from 0 and different from 1, the Chem. 14 elements are interconnected via amide bond(s).
31. The derivative of any of embodiments 1-30, wherein the linker and the protracting moiety are interconnected via an amide bond.
32. The derivative of any of embodiments 1-31, wherein the linker and the GLP-1 peptide are interconnected via an amide bond.
33. The derivative of any of embodiments 1-32, wherein the linker is attached to the epsilon-amino group of the first or the second K residue.
34. The derivative of any of embodiments 1-33, wherein the linker consists of Chem. 14 and two times Chem. 6 (Chem.14-2xChem.6), interconnected via amide bonds and in the sequence indicated, connected at its *—NH end to the CO—* end of the protracting moiety, and at its CO—* end to the epsilon amino group of the first or the second K residue of the GLP-1 peptide.
35. The derivative of any of embodiments 1-33, wherein the linker consists of Chem. 14, two times Chem. 13, and two times Chem. 6 (Chem.14-2xChem.13-2xChem.6), interconnected via amide bonds and in the sequence indicated, connected at its *—NH end to the CO—* end of the protracting moiety, and at its CO—* end to the epsilon amino group of the first or the second K residue of the GLP-1 peptide.
36. The derivative of any of embodiments 1-33, wherein the linker consists of Chem. 14, two times Chem. 13, and Chem. 6 (Chem.14-2xChem.13-Chem.6), interconnected via amide bonds and in the sequence indicated, connected at its *—NH end to the CO—* end of the protracting moiety, and at its CO—* end to the epsilon amino group of the first or the second K residue of the GLP-1 peptide.
37. The derivative of any of embodiments 1-36, wherein y is an odd number.
38. The derivative of any of embodiments 1-36, wherein y is an even number.
39. The derivative of embodiment 37, wherein y is 9.
40. The derivative of embodiment 37, wherein y is 11.
41. The derivative of embodiment 38, wherein y is 10.
42. The derivative of any of embodiments 1-41, wherein Chem. 2 is represented by

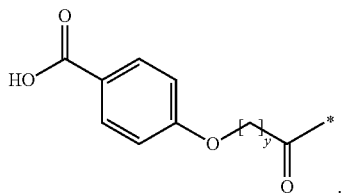

Chem. 2a

43. The derivative of any of embodiments 1-42, wherein the two protracting moieties are substantially identical.
44. The derivative of any of embodiments 1-43, wherein the two protracting moieties have a similarity of at least 0.5; preferably at least 0.6; more preferably at least 0.7, or at least 0.8; even more preferably at least 0.9; or most preferably at least 0.99, such as a similarity of 1.0.
45. The derivative of any of embodiments 1-44, wherein the two linkers are substantially identical.
46. The derivative of any of embodiments 1-45, wherein the two linkers have a similarity of at least 0.5; preferably at least 0.6; more preferably at least 0.7, or at least 0.8; even more preferably at least 0.9; or most preferably at least 0.99, such as a similarity of 1.0.
47. The derivative of any of embodiments 1-46, wherein the two side chains consisting of protracting moiety and linker are substantially identical.
48. The derivative of any of embodiments 1-47, wherein the two side chains consisting of protracting moiety and linker have a similarity of at least 0.5; preferably at least 0.6; more preferably at least 0.7, or at least 0.8; even more preferably at least 0.9; or most preferably at least 0.99, such as a similarity of 1.0.
49. The derivative of any of embodiments 43-48, wherein the two chemical structures to be compared are represented as fingerprints, such as a) ECFP_6 fingerprints; b) UNITY fingerprints; and/or c) MDL fingerprints; and wherein for each of a), b) and c) the Tanimoto coefficient is preferably used for calculating the similarity of the two fingerprints.
50. The derivative of any of embodiments 1-49, wherein the first K residue is designated $K^{26}$.
51. The derivative of any of embodiments 1-50, wherein the second K residue is designated $K^{34}$.
52. The derivative of any of embodiments 1-51, wherein the position corresponding to position 26 of GLP-1(7-37) (SEQ ID NO:1) is identified by handwriting and eyeballing.
53. The derivative of any of embodiments 1-52, wherein the position corresponding to position 34 of GLP-1(7-37) (SEQ ID NO:1) is identified by handwriting and eyeballing.
54. The derivative of any of embodiments 1-53, wherein the number of amino acid changes as compared to GLP-1(7-37) (SEQ ID NO:1) are identified by handwriting and eyeballing.
55. The derivative of any of embodiments 1-54, wherein the position corresponding to position 26 of GLP-1(7-37) (SEQ ID NO:1) is identified by use of a standard protein or peptide alignment program.
56. The derivative of any of embodiments 1-55, wherein the position corresponding to position 34 of GLP-1(7-37) (SEQ ID NO:1) is identified by use of a standard protein or peptide alignment program.
57. The derivative of any of embodiments 1-65, wherein the number of amino acid changes as compared to GLP-1(7-37) (SEQ ID NO:1) are identified by use of a standard protein or peptide alignment program.
58. The derivative of any of embodiments 56-57, wherein the alignment program is a Needleman-Wunsch alignment.
59. The derivative of any of embodiments 57-58, wherein the default scoring matrix and the default identity matrix is used.
60. The derivative of any of embodiments 57-59, wherein the scoring matrix is BLOSUM62.
61. The derivative of any of embodiments 57-60, wherein the penalty for the first residue in a gap is −10 (minus ten).
62. The derivative of any of embodiments 57-61, wherein the penalties for additional residues in a gap is −0.5 (minus point five).
63. The derivative of any of embodiments 1-62, wherein the peptide comprises no K residues other than the first and the second K residue.
64. The derivative of any of embodiments 1-63, wherein the peptide is GLP-1(7-37) (SEQ ID NO:1).
65. The derivative of any of embodiments 1-63, wherein the peptide is an analogue of GLP-1(7-37) (SEQ ID NO:1).
66. The derivative of embodiment 65-, wherein the amino acid change(s) is (are) at one or more positions corresponding to the following positions in GLP-1(7-37) (SEQ ID NO:1): Position 7, 8, 22, and/or 30.
67. The derivative of any of embodiments 65-66, wherein the analogue comprises at least one of the following changes: $Imp^7$, $Aib^8$, $E^{22}$, and/or $E^{30}$.
68. The derivative of any of embodiments 65-67, wherein the analogue comprises $Imp^7$.
69. The derivative of any of embodiments 65-68, wherein the analogue comprises $Aib^8$.
70. The derivative of any of embodiments 65-69, wherein the analogue comprises $E^{22}$.
71. The derivative of any of embodiments 1-69, wherein the analogue does not comprise $E^{22}$.
72. The derivative of any of embodiments 65-71, wherein the analogue comprises $E^{30}$.
73. The derivative of any of embodiments 1-72, wherein, for determination of the changes in the peptide, the amino acid sequence of the peptides compared to the amino acid sequence of native GLP-1(7-37) (SEQ ID NO:1).
74. The derivative of any of embodiments 1-73, wherein, for determination of a position in a peptide which corresponds to a specified position in native GLP-1(7-37) (SEQ ID NO:1), the amino acid sequence of the peptide is compared to the amino acid sequence of native GLP-1(7-37) (SEQ ID NO:1).
75. The derivative of any of embodiments 1-74, wherein the comparison of the amino acid sequence of the peptide with that of GLP-1(7-37) (SEQ ID NO:1) is done by handwriting and eyeballing.
76. The derivative of any of embodiments 1-75, wherein the comparison of the amino acid sequence of the peptide with that of GLP-1(7-37) (SEQ ID NO:1) is done by use of a standard protein or peptide alignment program.
77. The derivative of embodiment 76, wherein the alignment program is a Needleman-Wunsch alignment.
78. The derivative of any of embodiments 76-77, wherein the default scoring matrix and the default identity matrix is used.
79. The derivative of any of embodiments 76-78, wherein the scoring matrix is BLOSUM62.
80. The derivative of any of embodiments 76-79, wherein the penalty for the first residue in a gap is −10 (minus ten).

81. The derivative of any of embodiments 76-80, wherein the penalties for additional residues in a gap is −0.5 (minus point five).
82. The derivative of any of embodiments 76-81, wherein the position corresponding to any of the indicated positions of GLP-1(7-37) (SEQ ID NO:1) is identified by handwriting and eyeballing.
83. The derivative of any of embodiments 76-82, wherein the position corresponding to any of the indicated positions of GLP-1(7-37) (SEQ ID NO:1) is identified as described for position 26 and position 34 in any of embodiments 55-62.
84. The derivative of any of embodiments 1-83, wherein the peptide has a maximum of three amino acid changes.
85. The derivative of any of embodiments 1-84, wherein the peptide has a maximum of two amino acid changes.
86. The derivative of any of embodiments 1-85, wherein the peptide has a maximum of one amino acid change.
87. The derivative of any of embodiments 1-86, wherein the peptide has 0 (zero) amino acid changes.
88. The derivative of any of embodiments 1-87, wherein the peptide has a minimum of one amino acid modification.
89. The derivative of any of embodiments 1-88, wherein the peptide has a minimum of two amino acid changes.
90. The derivative of any of embodiments 1-89, wherein the peptide has a minimum of three amino acid changes.
91. The derivative of any of embodiments 1-90, wherein the peptide has one amino acid change.
92. The derivative of any of embodiments 1-90, wherein the peptide has two amino acid changes.
93. The derivative of any of embodiments 1-90, wherein the peptide has three amino acid changes.
94. The derivative of any of embodiments 1-93, wherein the changes, if any, are substitutions.
95. The derivative of any of embodiments 1-94, wherein the analogue a) comprises a GLP-1 analogue of Formula I; and/or b) is a GLP-1 analogue of Formula I:

$$\text{Xaa}_7\text{-Xaa}_8\text{-Glu-Gly-Thr-Xaa}_{12}\text{-Thr-Ser-Asp-Xaa}_{16}\text{-}$$
$$\text{Ser-Xaa}_{18}\text{-Xaa}_{19}\text{-Xaa}_{20}\text{-Glu-Xaa}_{22}\text{-Xaa}_{23}\text{-Ala-}$$
$$\text{Xaa}_{25}\text{-Lys-Xaa}_{27}\text{-Phe-Ile-Xaa}_{30}\text{-Xaa}_{31}\text{-Leu-}$$
$$\text{Xaa}_{33}\text{-Lys-Xaa}_{35}\text{-Xaa}_{36}\text{-Xaa}_{37}\text{-Xaa}_{38},\text{(SEQ ID NO: 3)} \quad \text{Formula I:}$$

wherein $Xaa_7$ is L-histidine, imidazopropionyl (Imp), α-hydroxy-histidine, D-histidine, desamino-histidine (desH), 2-amino-histidine, β-hydroxy-histidine, homohistidine, $N^\alpha$-acetyl-histidine, $N^\alpha$-formyl-histidine, α-fluoromethyl-histidine, α-methyl-histidine, 3-pyridylalanine, 2-pyridylalanine, or 4-pyridylalanine;

$Xaa_8$ is Ala, Gly, Val, Leu, Ile, Thr, Ser, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;

$Xaa_{12}$ is Phe or Leu;
$Xaa_{16}$ is Val or Leu;
$Xaa_{18}$ is Ser, Val, or Leu;
$Xaa_{19}$ is Tyr or Gln;
$Xaa_{20}$ is Leu or Met;
$Xaa_{22}$ is Gly, Glu, or Aib;
$Xaa_{23}$ is Gln, Glu, or Arg;
$Xaa_{25}$ is Ala or Val;
$Xaa_{27}$ is Glu or Leu;
$Xaa_{30}$ is Ala, Glu, or Arg;
$Xaa_{31}$ is Trp or His
$Xaa_{33}$ is Val;
$Xaa_{35}$ is Gly or Aib;
$Xaa_{36}$ is Arg or Gly;
$Xaa_{37}$ is Gly or Arg; and
$Xaa_{38}$ is Ser, Gly, Ala, Glu, Pro, Arg, or absent.

96. The derivative of embodiment 95, wherein the peptide of Formula I is an analogue of GLP-1(7-37) (SEQ ID NO:1).
97. The derivative of embodiment 95, wherein the peptide of Formula I is GLP-1(7-37) (SEQ ID NO:1).
98. The derivative of any of embodiments 95-97, wherein $Xaa_7$ is His or Imp (desH); $Xaa_8$ is Ala or Aib; $Xaa_{12}$ is Phe; $Xaa_{16}$ is Val; $Xaa_{18}$ is Ser; $Xaa_{19}$ is Tyr; $Xaa_{20}$ is Leu; $Xaa_{22}$ is Gly or Glu; $Xaa_{23}$ is Gln; $Xaa_{25}$ is Ala; $Xaa_{27}$ is Glu; $Xaa_{30}$ is Ala or Glu; $Xaa_{31}$ is Trp; $Xaa_{33}$ is Val; $Xaa_{34}$ is Gln; $Xaa_{35}$ is Gly; $Xaa_{36}$ is Arg; $Xaa_{37}$ is Gly; and $Xaa_{38}$ is absent.
99. The derivative of any of embodiments 95-98, wherein $Xaa_7$ is His.
100. The derivative of any of embodiments 95-98, wherein $Xaa_7$ is Imp.
101. The derivative of any of embodiments 95-100, wherein $Xaa_8$ is Ala.
102. The derivative of any of embodiments 95-100, wherein $Xaa_8$ is Aib.
103. The derivative of any of embodiments 95-102, wherein $Xaa_{12}$ is Phe.
104. The derivative of any of embodiments 95-103, wherein $Xaa_{16}$ is Val.
105. The derivative of any of embodiments 95-104, wherein $Xaa_{18}$ is Ser.
106. The derivative of any of embodiments 95-105, wherein $Xaa_{19}$ is Tyr.
107. The derivative of any of embodiments 95-106, wherein $Xaa_{20}$ is Leu.
108. The derivative of any of embodiments 95-107, wherein $Xaa_{22}$ is Gly.
109. The derivative of any of embodiments 95-107, wherein $Xaa_{22}$ is Glu.
110. The derivative of any of embodiments 95-108, wherein $Xaa_{22}$ is not Glu.
111. The derivative of any of embodiments 95-110, wherein $Xaa_{23}$ is Gln.
112. The derivative of any of embodiments 95-111, wherein $Xaa_{25}$ is Ala.
113. The derivative of any of embodiments 95-112, wherein $Xaa_{27}$ is Glu.
114. The derivative of any of embodiments 95-113, wherein $Xaa_{30}$ is Ala.
115. The derivative of any of embodiments 95-114, wherein $Xaa_{30}$ is Glu.
116. The derivative of any of embodiments 95-115, wherein $Xaa_{31}$ is Trp.
117. The derivative of any of embodiments 95-116, wherein $Xaa_{33}$ is Val.
118. The derivative of any of embodiments 95-117, wherein $Xaa_{35}$ is Gly.
119. The derivative of any of embodiments 95-118, wherein $Xaa_{36}$ is Arg.
120. The derivative of any of embodiments 95-119, wherein $Xaa_{37}$ is Gly.
121. The derivative of any of embodiments 95-120, wherein $Xaa_{38}$ is absent.
122. The derivative of any of embodiments 1-121, wherein the peptide comprises the following amino acid changes, as compared to GLP-1(7-37) (SEQ ID NO:1):
(i) 8Aib; (ii) 7Imp, 8Aib; (iii) 8Aib, 22E; or (iv) 8Aib, 22E, 30E.

123. The derivative of any of embodiments 1-122, wherein the peptide has the following amino acid changes, as compared to GLP-1(7-37) (SEQ ID NO:1):
(i) 8Aib; (ii) 7Imp, 8Aib; (iii) 8Aib, 22E; or (iv) 8Aib, 22E, 30E.
124. A compound, preferably according to any of embodiments 1-123, selected from the following: Chem. 21, Chem. 22, Chem. 23, Chem. 24, Chem. 25, Chem. 26, Chem. 27, Chem. 28, Chem. 29, Chem. 30, Chem. 31, and Chem. 32; or a pharmaceutically acceptable salt, amide, or ester thereof.
125. A compound, preferably a compound of embodiment 124, characterised by its name, and selected from a listing of each of the names of the compounds of Examples 1-12 herein; or a pharmaceutically acceptable salt, amide, or ester thereof.
126. The derivative of any of embodiments 1-125, which has GLP-1 activity.
127. The derivative of embodiment 126, wherein GLP-1 activity refers to the capability of activating the human GLP-1 receptor.
128. The derivative of embodiment 127, wherein activation of the human GLP-1 receptor is measured in an in vitro assay, as the potency of cAMP production.
129. The derivative of any of embodiments 1-128, which has a potency corresponding to an $EC_{50}$
a) below 10000 pM, preferably below 8000 pM, more preferably below 5000 pM, even more preferably below 4000 pM, or most preferably below 3000 pM;
b) below 2000 pM, preferably below 1200 pM, more preferably below 1000 pM, even more preferably below 800 pM, or most preferably below 600 pM;
c) below 400 pM, preferably below 300 pM, more preferably below 200 pM, even more preferably below 150 pM, or most preferably below 100 pM; or
d) below 80 pM, preferably below 60 pM, more preferably below 50 pM, even more preferably below 40 pM, or most preferably below 30 pM.
130. The derivative of embodiment 129, wherein the potency is determined as $EC_{50}$ for stimulation of the formation of cAMP in a medium containing the human GLP-1 receptor, such as a medium of the following composition (final in-assay concentrations) 50 mM TRIS-HCl; 5 mM HEPES; 10 mM $MgCl_2$, $6H_2O$; 150 mM NaCl; 0.01% Tween; 0.1% BSA; 0.5 mM IBMX; 1 mM ATP; 1 uM GTP, preferably using a stable transfected cell-line such as BHK467-12A (tk-ts13), and/or using for the determination of cAMP a functional receptor assay, e.g. based on competition between endogenously formed cAMP and exogenously added biotin-labelled cAMP, in which assay cAMP is more preferably captured using a specific antibody, and/or wherein an even more preferred assay is the AlphaScreen cAMP Assay, most preferably the one described in Example 20.
131. The derivative of any of embodiments 127-128, wherein activation of the human GLP-1 receptor is measured in an in vitro assay, in a reporter gene assay.
132. The derivative of embodiment 131, wherein the assay is performed in a stably transfected BHK cell line that expresses the human GLP-1 receptor and contains the DNA for the cAMP response element (CRE) coupled to a promoter and the gene for firefly luciferase (CRE luciferase).
133. The derivative of embodiment 132, wherein when assay incubation is completed luciferin is added and luminescence is measured.
134. The derivative of any of embodiments 131-133, wherein the assay is performed in the absence of serum albumin (0% HSA, final assay concentration).
135. The derivative of any of embodiments 131-134, wherein the assay is performed in the presence of 1% serum albumin (HSA, final assay concentration).
136. The derivative of any of embodiments 131-135, wherein the cells are BHK cells with BHK-ts13 as a parent cell line.
137. The derivative of any of embodiments 131-136, wherein the cells are derived from clone FCW467-12A.
138. The derivative of any of embodiments 131-137, wherein the cells are cultured at 5% $CO_2$ in cell culture medium, aliquoted and stored in liquid nitrogen.
139. The derivative of embodiment 138, wherein the cell culture medium is 10% FBS (Fetal Bovine Serum), 1 mg/ml G418, 240 nM MTX (methotrexate) and 1% pen/strep (penicillin/streptomycin).
140. The derivative of any of embodiments 131-139, wherein before each assay a cell culture aliquot is taken up and washed twice in PBS before being suspended at the desired concentration in assay buffer.
141. The derivative of any of embodiments 131-140, wherein for 96-well plates the suspension is made to give a final concentration of $5 \times 10^3$ cells/well.
142. The derivative of any of embodiments 140-141, wherein the assay buffer is 1% assay buffer, which consists of 2% ovalbumin, 0.2% Pluronic F-68 and 2% HSA in assay medium.
143. The derivative of any of embodiments 140-141, wherein the assay buffer is 0% assay buffer, which consists of 2% ovalbumin and 0.2% Pluronic F-68 in assay medium.
144. The derivative of any of embodiments 142-143, wherein assay medium consists of DMEM w/o phenol red, 10 mM Hepes and 1× Glutamax.
145. The derivative of any of embodiments 131-144, wherein the assay procedure comprises the following steps:
i) Cell stocks are thawed in a 37° C. water bath;
ii) cells are washed three times in PBS;
iii) the cells are counted and adjusted to $5 \times 10^3$ cells/50 μl ($1 \times 10^5$ cells/ml) in assay medium, and a 50 μl aliquot of cells is transferred to each well in the assay plate;
iv) stocks of the test compounds and reference compounds, if any, are diluted to a concentration of 0.2 μM in either 0% assay buffer for the 0% HSA assay or 1% assay buffer for the 1% HSA assay; and compounds are diluted 10-fold to give a suitable range of concentrations (such as: $2 \times 10^{-7}$ M, $2 \times 10^{-8}$ M; $2 \times 10^{-9}$ M, $2 \times 10^{-10}$ M, $2 \times 10^{-11}$ M, $2 \times 10^{-12}$ M and $2 \times 10^{-13}$ M), and for each compound a blank assay buffer control is also included;
v) a 50 μl aliquot of compound or blank is transferred in triplicate from the dilution plate to the assay plate, and compounds are tested at suitable concentrations (such as the following final concentrations: $1 \times 10^{-7}$ M, $1 \times 10^{-8}$ M; $1 \times 10^{-9}$ M, $1 \times 10^{-10}$ M, $1 \times 10^{-11}$ M, $1 \times 10^{-12}$ M and $1 \times 10^{-13}$ M);
vi) the assay plate is incubated for 3 h in a 5% $CO_2$ incubator at 37° C.;
vii) the assay plate is removed from the incubator and allowed to stand at room temperature for 15 min;
ixx) a 100 μl aliquot of luciferin (such as steadylite plus reagent) is added to each well of the assay plate;
ix) each assay plate is covered to protect it from light and shaken for 30 min at room temperature; and
x) each assay plate is read, for example in a Packard TopCount NXT instrument.

146. The derivative of embodiment 145, wherein the data from the TopCount instrument are transferred to GraphPad Prism 5 software for desired calculations.
147. The derivative of any of embodiments 131-146, wherein values for each triplicate is averaged, a non-linear regression performed, and the $EC_{50}$ values calculated.
148. The derivative of any of embodiments 145-147, wherein the regression is (log(agonist) vs response-Variable slope (four parameter)).
149. The derivative of any of embodiments 127-128, wherein the potency is determined as described in any of embodiments 131-148.
150. The derivative of embodiment 149, wherein the potency is determined as described in Example 21.
151. The derivative of any of embodiments 131-150, the $EC_{50}$ value of which is no more than 20 times the $EC_{50}$ value for semaglutide.
152. The derivative of any of embodiments 131-151, the $EC_{50}$ value of which is no more than 15 times the $EC_{50}$ value for semaglutide.
153. The derivative of any of embodiments 131-152, the $EC_{50}$ value of which is no more than 10 times the $EC_{50}$ value for semaglutide.
154. The derivative of any of embodiments 131-153, the $EC_{50}$ value of which is no more than 5 times the $EC_{50}$ value for semaglutide.
155. The derivative of any of embodiments 131-154, the $EC_{50}$ value of which is no more than 2.5 times the $EC_{50}$ value for semaglutide.
156. The derivative of any of embodiments 131-155, the $EC_{50}$ value of which is lower than the $EC_{50}$ value for semaglutide.
157. The derivative of any of embodiments 131-156, the $EC_{50}$ value of which is less than 0.75 times the $EC_{50}$ value for semaglutide.
158. The derivative of any of embodiments 131-157, the $EC_{50}$ value of which is less than 0.50 times the $EC_{50}$ value for semaglutide.
159. The derivative of any of embodiments 1-158, for which the GLP-1 receptor binding affinity ($IC_{50}$) in the presence of approximately 0.001% HSA (low albumin) is
a) below 500 nM, preferably below 250 nM, more preferably below 100 nM, or most preferably below 50 nM;
b) below 10 nM, preferably below 8.0 nM, still more preferably below 6.0 nM, even more preferably below 5.0 nM, or most preferably below 3.0 nM;
c) below 2.0 nM, preferably below 1.0 nM, even more preferably below 0.80 nM, or most preferably below 0.60 nM; or
d) below 0.40 nM, preferably below 0.30 nM, even more preferably below 0.20 nM, or most preferably below 0.10 nM.
160. The derivative of embodiment 127, wherein activation of the human GLP-1 receptor is measured as GLP-1 receptor binding affinity ($IC_{50}$) in the presence of approximately 0.001% HSA (low albumin).
161. The derivative of any of embodiments 1-160, for which the GLP-1 receptor binding affinity ($IC_{50}$) in the presence of 2.0% HSA (high albumin) is
a) below 1000 nM, preferably below 800 nM;
b) below 700 nM, preferably below 500 nM, more preferably below 300 nM; or
c) below 200 nM, preferably below 100 nM, or more preferably below 50 nM.
162. The derivative of any of embodiments 159-161, wherein the binding affinity to the GLP-1 receptor is measured by way of displacement of $^{125}$I-GLP-1 from the receptor, preferably using a SPA binding assay.
163. The derivative of embodiment 161, wherein the GLP-1 receptor is prepared using a stable, transfected cell line, preferably a hamster cell line, more preferably a baby hamster kidney cell line, such as BHK tk-ts13.
164. The derivative of any of embodiments 159-163, wherein the $IC_{50}$ value is determined as the concentration which displaces 50% of $^{125}$I-GLP-1 from the receptor.
165. The derivative of any of embodiments 1-164, which has an oral bioavailability, preferably an absolute oral bioavailability, which is higher than that of semaglutide.
166. The derivative of any of embodiments 1-165, which has an oral bioavailability, preferably an absolute oral bioavailability, which is higher than that of liraglutide.
167. The derivative of any of embodiments 1-166, wherein the derivative is effective at lowering blood glucose in vivo in db/db mice.
168. The derivative of any of embodiments 1-167, wherein the derivative is effective at lowering body weight in vivo in db/db mice.
169. The derivative of any of embodiments 1-168 which, in a PD study in pigs, reduces food intake on day 1, 2, 3, and/or 4 after s.c. administration of a single dose of the derivative, as compared to a vehicle-treated control group.
170. The derivative of embodiment 169 wherein the dose is 0.3, 1, 3, 10 or 30 nmol/kg; preferably 3.0 nmol/kg.
171. The derivative of any of embodiments 169-170, wherein the food intake on day 1 is reduced to 80% or lower, preferably to 60% or lower, more preferably to 50% or lower, or most preferably to 40% or lower.
172. The derivative of any of embodiments 169-171, wherein the food intake on day 2 is reduced to 80% or lower, preferably to 60% or lower, or more preferably to 40% or lower.
173. The derivative of any of embodiments 169-172, wherein the study is conducted and the data compiled and analysed as described in Example 25.
174. The derivative of any of embodiments 1-173, which has a more protracted profile of action than liraglutide.
175. The derivative of embodiment 174, wherein protraction means half-life in vivo in a relevant animal species, such as db/db mice, rat, pig, and/or, preferably, minipig; wherein the derivative is administered i) s.c., and/or, ii) i.v.; preferably ii) i.v.
176. The derivative of any of embodiments 1-175, wherein the terminal half-life ($T_{1/2}$) after i.v. administration in rat is higher than that of semaglutide.
177. The derivative of any of embodiments 1-176, wherein the terminal half-life ($T_{1/2}$) after i.v. administration in rat is at least a) 25% higher, b) 50% higher, c) 75% higher, or d) 100% higher (=twice) than the terminal half-life of semaglutide.
178. The derivative of any of embodiments 1-177, wherein the terminal half-life ($T_{1/2}$) after i.v. administration in rat is at least two times the terminal half-life of semaglutide.
179. The derivative of any of embodiments 174-178, wherein the half-life is determined in in vivo pharmacokinetic studies in rat, for example as described in Example 24.
180. The derivative of any of embodiments 1-179, wherein the terminal half-life ($T_{1/2}$) after i.v. administration in minipigs is
a) at least 8 hours, preferably at least 16 hours, more preferably at least 24 hours, even more preferably at least 32 hours, or most preferably at least 40 hours; or b) at least 50 hours, preferably at least 55 hours, more preferably at least 60 hours, or even more preferably at least 65 hours.
181. The derivative of embodiment 180, wherein the minipigs are male Göttingen minipigs.
182. The derivative of any of embodiments 180-181, wherein the minipigs are 7-14 months of age, and preferably weighing from 16-35 kg.
183. The derivative of any of embodiments 180-182, wherein the minipigs are housed individually, and fed once or twice daily, preferably with SDS minipig diet.
184. The derivative of any of embodiments 180-183, wherein the derivative is dosed, i.v., after at least 2 weeks of acclimatisation.
185. The derivative of any of embodiments 180-184, wherein the animals are fasted for approximately 18 h before dosing and from 0 to 4 h after dosing, and have ad libitum access to water during the whole period.
186. The derivative of any of embodiments 180-185, wherein the GLP-1 derivative is dissolved in 50 mM sodium phosphate, 145 mM sodium chloride, 0.05% tween 80, pH 7.4 to a suitable concentration, preferably from 20-60 nmol/ml.
187. The derivative of any of embodiments 180-188, wherein intravenous injections of the derivative are given in a volume corresponding to 1-2 nmol/kg.
188. An intermediate product in the form of a GLP-1 analogue selected from the following analogues of GLP-1(7-37) (SEQ ID NO:1): (i) 8aib; (ii) 7Imp, 8Aib; (iii) 8Aib, 22E; or (iv) 8Aib, 22E, 30E or a pharmaceutically acceptable salt, amide, or ester of any of the analogues of (i), (ii), (iii), or (iv).
189. The analogue of embodiment 188, wherein the comparison with GLP-1(7-37) (SEQ ID NO:1) is made by handwriting and eyeballing.
190. The analogue of any of embodiments 188-189, wherein the comparison with GLP-1(7-37) (SEQ ID NO:1) is made by use of a standard protein or peptide alignment program.
191. The analogue of embodiment 190, wherein the alignment program is a Needleman-Wunsch alignment.
192. The analogue of any of embodiments 188-191, wherein the default scoring matrix and the default identity matrix is used.
193. The analogue of any of embodiments 188-192, wherein the scoring matrix is BLOSUM62.
194. The analogue of any of embodiments 188-193, wherein the penalty for the first residue in a gap is −10 (minus ten).
195. The analogue of any of embodiments 188-194, wherein the penalties for additional residues in a gap is −0.5 (minus point five).
196. A pharmaceutical composition comprising a derivative according to any of embodiments 1-195, and a pharmaceutically acceptable excipient.
197. A derivative according to any of embodiments 1-195, for use as a medicament.
198. A derivative according to any of embodiments 1-195, for use in the treatment and/or prevention of all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression.
199. Use of a derivative according to any of embodiments 1-195 in the manufacture of a medicament for the treatment and/or prevention of all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression.
200. A method for treating or preventing all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression—by administering a pharmaceutically active amount of a derivative according to any of embodiments 1-195.

The invention also relates to a derivative of a GLP-1 analogue, which analogue comprises a first K residue at a position corresponding to position 26 of GLP-1(7-37) (SEQ ID NO:1), a second K residue at a position corresponding to position 34 of GLP-1(7-37) (SEQ ID NO:1), and a maximum of eight amino acid changes as compared to GLP-1 (7-37), which derivative comprises a first and a second protracting moiety attached to said first and second K residue, respectively, via a first and a second linker, respectively, wherein the first and the second protracting moiety is Chem. 2:

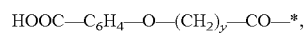  Chem. 2:

in which y is an integer in the range of 6-13; and the first and the second linker comprises

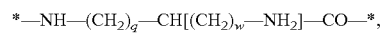  Chem. 3:

wherein q is an integer in the range of 0-5, and w is an integer in the range of 0-5; or a pharmaceutically acceptable salt, amide, or ester thereof; as well as any of the above embodiments 2-200 appended hereto as dependent embodiments.

The invention also relates to
a). A derivative of a GLP-1 peptide,
which peptide comprises a first K residue at a position corresponding to position 26 of GLP-1(7-37) (SEQ ID NO:1), a second K residue at a position corresponding to position 34 of GLP-1(7-37) (SEQ ID NO:1), and a maximum of eight amino acid changes as compared to GLP-1 (7-37);
which derivative comprises two protracting moieties attached to the first and second K residue, respectively, via a linker, wherein the protracting moiety is Chem. 2:

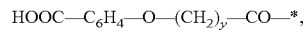  Chem. 2:

in which y is an integer in the range of 6-13, and the linker comprises Chem. 3:

  Chem. 3:

wherein q is an integer in the range of 0-5, and w is an integer in the range of 0-5;
or a pharmaceutically acceptable salt, amide, or ester thereof.
b). The derivative of embodiment a), wherein Chem. 3 is connected at its CO—* end to the epsilon amino group of the first or the second K residue of the GLP-1 peptide.
c). The derivative of any of embodiments a)-b), wherein the linker comprises z times Chem. 3, wherein z is an integer in the range of 1-2.
d). The derivative of any of embodiments a)-c), wherein w is 0.

e). The derivative of any of embodiments a)-d), wherein q is 4.

f). The derivative of any of embodiments a)-e), wherein the linker comprises

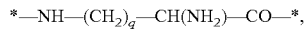

$$*-NH-(CH_2)_q-CH(NH_2)-CO-*,\qquad\text{Chem. 4:}$$

wherein q is an integer in the range of 3-5.

g). The derivative of any of embodiments a)-f), wherein the linker comprises

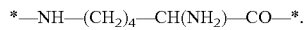

$$*-NH-(CH_2)_4-CH(NH_2)-CO-*.\qquad\text{Chem. 6:}$$

h). The derivative of any of embodiments a)-g), wherein y is 9, 10, or 11.

i). The derivative of any of embodiments a)-h), wherein the analogue comprises a GLP-1 analogue of Formula I:

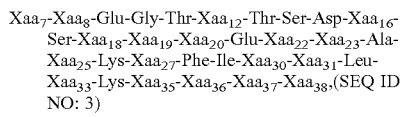

$$\text{Xaa}_7\text{-Xaa}_8\text{-Glu-Gly-Thr-Xaa}_{12}\text{-Thr-Ser-Asp-Xaa}_{16}\text{-}$$
$$\text{Ser-Xaa}_{18}\text{-Xaa}_{19}\text{-Xaa}_{20}\text{-Glu-Xaa}_{22}\text{-Xaa}_{23}\text{-Ala-}$$
$$\text{Xaa}_{25}\text{-Lys-Xaa}_{27}\text{-Phe-Ile-Xaa}_{30}\text{-Xaa}_{31}\text{-Leu-}$$
$$\text{Xaa}_{33}\text{-Lys-Xaa}_{35}\text{-Xaa}_{36}\text{-Xaa}_{37}\text{-Xaa}_{38},\text{(SEQ ID}$$
$$\text{NO: 3)}\qquad\text{Formula I:}$$

wherein $\text{Xaa}_7$ is L-histidine, imidazopropionyl (Imp), α-hydroxy-histidine, D-histidine, desamino-histidine (desH), 2-amino-histidine, β-hydroxy-histidine, homohistidine, $N^\alpha$-acetyl-histidine, $N^\alpha$-formyl-histidine, α-fluoromethyl-histidine, α-methyl-histidine, 3-pyridylalanine, 2-pyridylalanine, or 4-pyridylalanine;

$\text{Xaa}_8$ is Ala, Gly, Val, Leu, Ile, Thr, Ser, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;

$\text{Xaa}_{12}$ is Phe or Leu;
$\text{Xaa}_{16}$ is Val or Leu;
$\text{Xaa}_{18}$ is Ser, Val, or Leu;
$\text{Xaa}_{19}$ is Tyr or Gln;
$\text{Xaa}_{20}$ is Leu or Met;
$\text{Xaa}_{22}$ is Gly, Glu, or Aib;
$\text{Xaa}_{23}$ is Gln, Glu, or Arg;
$\text{Xaa}_{25}$ is Ala or Val;
$\text{Xaa}_{27}$ is Glu or Leu;
$\text{Xaa}_{30}$ is Ala, Glu, or Arg;
$\text{Xaa}_{31}$ is Trp or His;
$\text{Xaa}_{33}$ is Val;
$\text{Xaa}_{35}$ is Gly or Aib;
$\text{Xaa}_{36}$ is Arg or Gly;
$\text{Xaa}_{37}$ is Gly or Arg; and
$\text{Xaa}_{38}$ is Ser, Gly, Ala, Glu, Pro, Arg, or absent.

j). A compound selected from the following: Chem. 21, Chem. 22, Chem. 23, Chem. 24, Chem. 25, Chem. 26, Chem. 27, Chem. 28, Chem. 29, Chem. 30, Chem. 31, and Chem. 32; or a pharmaceutically acceptable salt, amide, or ester thereof.

k). A pharmaceutical composition comprising a derivative according to any of embodiments a)-j), and a pharmaceutically acceptable excipient.

l). A derivative according to any of embodiments a)-j), for use as a medicament.

m). A derivative according to any of embodiments a)-j), for use in the treatment and/or prevention of all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression.

n). Use of a derivative according to any of embodiments a)-j) in the manufacture of a medicament for the treatment and/or prevention of all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression.

o). A method for treating or preventing all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression—by administering a pharmaceutically active amount of a derivative according to any of embodiments a)-j).

EXAMPLES

This experimental part starts with a list of abbreviations, and is followed by a section including general methods for synthesising and characterising analogues and derivatives of the invention. Then follows a number of examples which relate to the preparation of specific GLP-1 derivatives, and at the end a number of examples have been included relating to the activity and properties of these analogues and derivatives (section headed pharmacological methods).

The examples serve to illustrate the invention.

LIST OF ABBREVIATIONS

Aib: α-aminoisobutyric acid
AcOH: acetic acid
API: Active Pharmaceutical Ingredient
AUC: Area Under the Curve
BG: Blood Glucose
BHK Baby Hamster Kidney
BW: Body Weight
Boc: t-butyloxycarbonyl
Bom: benzyloxymethyl
BSA: Bovine serum albumin
Bzl: benzyl
CAS: Chemical Abstracts Service
Clt: 2-chlorotrityl
collidine: 2,4,6-trimethylpyridine
DCM: dichloromethane
Dde: 1-(4,4-dimethyl-2,6-dioxocyclohexylidene)ethyl
DesH: des-amino histidine (may also be referred to as imidazopropionic acid, Imp)
DIC: diisopropylcarbodiimide
DIPEA: diisopropylethylamine
DMEM: Dulbecco's Modified Eagle's Medium (DMEM)
EDTA: ethylenediaminetetraacetic acid
EGTA: ethylene glycol tetraacetic acid
FBS: Fetal Bovine Serum
FCS: Fetal Calf Serum
Fmoc: 9-fluorenylmethyloxycarbonyl
HATU: (O-(7-azabenzotriazol-1-yl)-1,1,3,3-tetramethyluronium hexafluorophosphate)
HBTU: (2-(1H-benzotriazol-1-yl-)-1,1,3,3 tetramethyluronium hexafluorophosphate)
HEPES: 4-(2-hydroxyethyl)-1-piperazineethanesulfonic acid
HFIP 1,1,1,3,3,3-hexafluoro-2-propanol or hexafluoroisopropanol HOAt: 1-hydroxy-7-azabenzotriazole
HOBt: 1-hydroxybenzotriazole
HPLC: High Performance Liquid Chromatography
HSA: Human Serum Albumin
IBMX: 3-isobutyl-1-methylxanthine
Imp: Imidazopropionic acid (also referred to as des-amino histidine, DesH)
i.v. intravenously
ivDde: 1-(4,4-dimethyl-2,6-dioxocyclohexylidene)-3-methylbutyl
IVGTT: Intravenous Glucose Tolerance Test
LCMS: Liquid Chromatography Mass Spectroscopy
LYD: Landrace Yorkshire Duroc
MALDI-MS: See MALDI-TOF MS
MALDI-TOF MS: Matrix-Assisted Laser Desorption/Ionisation Time of Flight Mass Spectroscopy
MeOH: methanol
Mmt: 4-methoxytrityl
Mtt: 4-methyltrityl
MTX: methotrexate
NMP: N-methyl pyrrolidone
OBz: benzoyl ester
OEG: 8-amino-3,6-dioxaoctanic acid
OPfp: pentafluorophenoxy
OPnp: para-nitrophenoxy
OSu: O-succinimidyl esters (hydroxysuccinimide esters)
OtBu: tert butyl ester
Oxyma Pure®: Cyano-hydroxyirnino-acetic acid ethyl ester
Pbf: 2,2,4,6,7-pentamethyldihydrobenzofuran-5-sulfonyl
PBS: Phosphate Buffered Saline
PD: Pharmacodynamic
Pen/Strep: Pencillin/Streptomycin
PK: Pharmacokinetic
RP: Reverse Phase
RP-HPLC: Reverse Phase High Performance Liquid Chromatography
RT: Room Temperature
Rt: Retention time
s.c.: Subcutaneously
SD: Standard Deviation
SEC-HPLC: Size Exclusion High Performance Liquic Chromatography
SEM: Standard Error of Mean
SPA: Scintillation Proximity Assay
SPPS: Solid Phase Peptide Synthesis
tBu: tert. butyl
TFA: trifluoroacetic acid
TIS: triisopropylsilane
TLC: Thin Layer Chromatography
Tos: tosylate (or pare-toluenesulfonyl)
Tris: tris(hydroxymethyl)aminomethane or 2-amino-2-hydroxymethyl-propane-1,3-diol
Trt: triphenylmethyl (trityl)
Trx: tranexamic acid
UPLC: Ultra Performance Liquid Chromatography
Materials and Methods
Materials
α-picoline borane complex (CAS 3999-38-0)
Cyano-hydroxyimino-acetic acid ethyl ester (CAS 3849-21-6)
N-α,N-β-Di-Fmoc-L-2,3-Diaminopropionic Acid (CAS 201473-90-7)
3,5-Di-tert-butyl-4-hydroxybenzoic acid (CAS 1421-49-4)
3,5-Di-tert-butylbenzoic Acid (CAS 16225-26-6)
Fmoc-8-amino-3,6-dioxaoctanoic acid (CAS 166108-71-0)
17-(9-Fluorenylmethyloxycarbonyl-amino)-9-aza-3,6,12,15-tetraoxa-10-on-heptadecanoic acid (IRIS Biotech GmbH)
Fmoc-L-Glutamic acid 1-tert-butyl ester (CAS 84793-07-7)
2-(2-Methoxyethoxy)acetic acid (CAS 16024-56-9)
N-α,N-ε-Bis(9-fluorenylmethyloxycarbonyl)-L-lysine (CAS 78081-87-5)
1-[(9H-fluoren-9-ylmethoxy)carbonyl]piperidine-4-carboxylic acid (CAS 148928-15-8)
FMOC-8-Aminocapryl acid (CAS 126631-93-4)
4-Phenylbutyric acid (CAS 1716-12-7)
4-(4-Nitrophenyl)butyric acid (CAS 5600-62-4)
4-(4-Chlorophenyl)butyric acid (CAS 4619-18-5)
FMOC-6-Aminohexanoic acid (CAS 88574-06-5)
FMOC-12-Aminododecanoic acid (CAS 128917-74-8)
4-(9-carboxy-nonyloxy)-benzoic acid tert-butyl ester (prepared as described in Example 25, step 1 and 2 of WO 2006/082204)
4-(8-Carboxy-octyloxy)-benzoic acid tert-butyl ester (M.p.: 71-72° C.
$^1$H NMR (300 MHz, CDCl$_3$, δ$_H$): 7.93 (d, J=8.9 Hz, 2H); 6.88 (d, J=8.9 Hz, 2H); 4.00 (t, J=6.4 Hz, 2H); 2.36 (t, J=7.4 Hz, 2H); 1.80 (m, 2H); 1.65 (m, 2H); 1.59 (s, 9H); 1.53-1.30 (m, 8H) (prepared as described in Example 25, step 1 and 2 of WO 2006/082204, replacing methyl 10-bromodecanoate with ethyl 9-Bromononanoate (CAS 28598-81-4))
4-(7-Carboxy-heptyloxy)-benzoic acid tert-butyl ester ($^1$H NMR spectrum (300 MHz, CDCl$_3$, δ$_H$): 7.93 (d, J=9.0 Hz, 2H); 6.88 (d, J=9.0 Hz, 2H); 4.00 (t, J=6.5 Hz, 2H); 2.37 (t, J=7.4 Hz, 2H); 1.80 (m, 2H); 1.64 (m, 2H); 1.59 (s, 9H); 1.53-1.33 (m, 6H)) (prepared as described in Example 25, step 1 and 2 of WO 2006/082204, replacing methyl 10-bromodecanoate with ethyl 7-bromoheptanoate (CAS 29823-18-5))
Chemical Methods
This section is divided in two: Section A relating to general methods (of preparation (A1); and of detection and characterisation (A2)), and section B, in which the preparation and characterisation of a number of specific example compounds is described.

A. General Methods

A1. Methods of Preparation

This section relates to methods for solid phase peptide synthesis (SPPS methods, including methods for de-protection of amino acids, methods for cleaving the peptide from the resin, and for its purification), as well as methods for detecting and characterising the resulting peptide (LCMS, MALDI, and UPLC methods). The solid phase synthesis of peptides may in some cases be improved by the use of di-peptides protected on the di-peptide amide bond with a group that can be cleaved under acidic conditions such as, but not limited to, 2-Fmoc-oxy-4-methoxybenzyl, or 2,4,6-trimethoxybenzyl. In cases where a serine or a threonine is present in the peptide, pseudoproline di-peptides may be used (available from, e.g., Novabiochem, see also W. R. Sampson (1999), J. Pep. Sci. 5, 403). The Fmoc-protected amino acid derivatives used were the standard recommended: Fmoc-Ala-OH, Fmoc-Arg(Pbf)-OH, Fmoc-Asn(Trt)-OH, Fmoc-Asp(OtBu)-OH, Fmoc-Cys(Trt)-OH, Fmoc-Gln(Trt)-OH, Fmoc-Glu(OtBu)-OH, Fmoc-Gly-OH, Fmoc-His(Trt)-OH, Fmoc-Ile-OH, Fmoc-Leu-OH, Fmoc-Lys(Boc)-OH, Fmoc-Met-OH, Fmoc-Phe-OH, Fmoc-Pro-OH, Fmoc-Ser(tBu)-OH, Fmoc-Thr(tBu)-OH, Fmoc-Trp(Boc)-OH, Fmoc-Tyr(tBu)-OH, or, Fmoc-Val-OH etc. supplied from e.g. Anaspec, Bachem, Iris Biotech, or Novabiochem. Where nothing else is specified the natural L-form of the amino acids are used. The N-terminal amino acid was Boc protected at the alpha amino group (e.g. Boc-His(Boc)-OH, or Boc-His(Trt)-OH for peptides with His at the N-terminus). In case of modular albumin binding moiety attachment using SPPS the following suitably protected building blocks such as but not limited to Fmoc-8-amino-3,6-dioxaoctanoic acid, Fmoc-tranexamic acid, Fmoc-Glu-OtBu, octadecanedioic acid mono-tert-butyl ester, nonadecanedioic acid mono-tert-butyl ester, tetradecanedioic acid mono-tert-butyl ester, or 4-(9-carboxynonyloxy) benzoic acid tert-butyl ester were used. All operations stated below were performed at 250-µmol synthesis scale.

1. Synthesis of Resin Bound Protected Peptide Backbone

Method: SPPS_P

SPPS_P was performed on a Prelude Solid Phase Peptide Synthesiser from Protein Technologies (Tucson, Ariz. 85714 U.S.A.) at 250-µmol scale using six fold excess of Fmoc-amino acids (300 mM in NMP with 300 mM HOAt or Oxyma Pure®) relative to resin loading, e.g. low load Fmoc-Gly-Wang (0.35 mmol/g). Fmoc-deprotection was performed using 20% piperidine in NMP. Coupling was performed using 3:3:3:4 amino acid/(HOAt or Oxyma Pure®)/DIC/collidine in NMP. NMP and DCM top washes (7 ml, 0.5 min, 2×2 each) were performed between deprotection and coupling steps. Coupling times were generally 60 minutes. Some amino acids including, but not limited to Fmoc-Arg(Pbf)-OH, Fmoc-Aib-OH or Boc-His(Trt)-OH were "double coupled", meaning that after the first coupling (e.g. 60 min), the resin is drained and more reagents are added (amino acid, (HOAt or Oxyma Pure®), DIC, and collidine), and the mixture allowed to react again (e.g. 60 min).

Method: SPPS_L

SPPS_L was performed on a microwave-based Liberty peptide synthesiser from CEM Corp. (Matthews, N.C. 28106, U.S.A.) at 250-µmol or 100-µmol scale using six fold excess of Fmoc-amino acids (300 mM in NMP with 300 mM HOAt or Oxyma Pure®) relative to resin loading, e.g. low load Fmoc-Gly-Wang (0.35 mmol/g). Fmoc-deprotection was performed using 5% piperidine in NMP at up to 75° C. for 30 seconds where after the resin was drained and washed with NMP and the Fmoc-deprotection was repeated this time for 2 minutes at 75° C. Coupling was performed using 1:1:1 amino acid/(HOAt or Oxyma Pure®)/DIC in NMP. Coupling times and temperatures were generally 5 minutes at up to 75° C. Longer coupling times were used for larger scale reactions, for example 10 min. Histidine amino acids were double coupled at 50° C., or quadruple coupled if the previous amino acid was sterically hindered (e.g. Aib). Arginine amino acids were coupled at RT for 25 minutes and then heated to 75° C. for 5 min. Some amino acids such as but not limited to Aib, were "double coupled", meaning that after the first coupling (e.g. 5 min at 75° C.), the resin is drained and more reagents are added (amino acid, (HOAt or Oxyma Pure®) and DIC), and the mixture is heated again (e.g. 5 min at 75° C.). NMP washes (5×10 ml) were performed between deprotection and coupling steps.

Method: SPPS_A

The protected peptidyl resin was synthesised according to the Fmoc strategy on an Applied Biosystems 433 peptide synthesiser in a 250-µmol or 1000 µmol scale with three or four fold excess of Fmoc-amino acids, using the manufacturer supplied FastMoc UV protocols which employ HBTU (2-(1H-Benzotriazol-1-yl)-1,1,3,3 tetramethyluronium hexafluorophosphate) or HATU (O-(7-azabenzotriazol-1-yl)-1,1,3,3-tetramethyluronium hexafluorophosphate) mediated couplings in NMP and UV monitoring of the deprotection of the Fmoc protection group, in some cases double couplings were used, meaning that after the first coupling, the resin is drained and more Fmoc-amino acids and reagents are added. The starting resin used for the synthesis of the peptide amides was Rink-Amide resin and either preloaded Wang (e.g. low load Fmoc-Gly-Wang or Fmoc-Lys(Mtt)-wang) or chlorotrityl resin for peptides with a carboxy C-terminal. The protected amino acid derivatives used were standard Fmoc-amino acids (supplied from e.g. Anaspec, or Novabiochem) supplied in preweighed cartridges suitable for the AB1433A synthesiser with the exception of unnatural aminoacids such as Fmoc-Aib-OH (Fmoc-aminoisobutyric acid). The N terminal amino acid was Boc protected at the alpha amino group (e.g. Boc-His(Boc)-OH or Boc-His(Trt)-OH was used for peptides with His at the N-terminal). The epsilon amino group of lysines in the sequence were either protected with Mtt, Mmt, Dde, ivDde, or Boc, depending on the route for attachment of the albumin binding moiety and spacer. The synthesis of the peptides may in some cases be improved by the use of dipeptides protected on the dipeptide amide bond with a group that can be cleaved under acidic conditions such but not limited to 2-Fmoc-oxy-4-methoxybenzyl or 2,4,6-trimethoxybenzyl. In cases where a serine or a threonine is present in the peptide, the use of pseudoproline dipeptides may be used (see e.g. catalogue from Novobiochem 2009/2010 or newer version, or W. R. Sampson (1999), J. Pep. Sci. 5, 403).

Method: SPPS_M

SPPS_M refers to synthesis of the protected peptidyl resin using manual Fmoc chemistry. The coupling chemistry was DIC/(HOAt or Oxyma Pure®)/collidine in NMP at a 4-10 fold molar excess. Coupling conditions were 1-6 h at room temperature. Fmoc-deprotection was performed with 20-25% piperidine in NMP (3×20 ml, each 10 min) followed by NMP washings (4×20 mL).

2. Synthesis of Side Chains

Mono Esters of Fatty Diacids

Overnight reflux of the C8, C10, C12, C14, C16 and C18 diacids with Boc-anhydride DMAP t-butanol in toluene gives predominately the t-butyl mono ester. Obtained is after work-up a mixture of mono acid, diacid and diester. Purification is carried out by washing, short plug silica filtration and crystallisation.

3. Attachment of Side Chains to Resin Bound Protected Peptide Backbone

When an acylation is present on a lysine side chain, the epsilon amino group of lysine to be acylated was protected with either Mtt, Mmt, Dde, ivDde, or Boc, depending on the route for attachment of the protracting moiety and linker. Dde- or ivDde-deprotection was performed with 2% hydrazine in NMP (2×20 ml, each 10 min) followed by NMP washings (4×20 ml). Mtt- or Mmt-deprotection was performed with 2% TFA and 2-3% TIS in DCM (5×20 ml, each 10 min) followed by DCM (2×20 ml), 10% MeOH and 5% DIPEA in DCM (2×20 ml) and NMP (4×20 ml) washings, or by treatment with hexafluoroisopropanol/DCM (75:25, 5×20 ml, each 10 min) followed by washings as above. In some cases the Mtt group was removed by automated steps on the Liberty peptide synthesiser. Mtt deprotection was performed with hexafluoroisopropanol or hexafluoroisopropanol/DCM (75:25) at room temperature for 30 min followed by washing with DCM (7 ml×5), followed by NMP washings (7 ml×5). The protracting moiety and/or linker can be attached to the peptide either by acylation of the resin bound peptide or by acylation in solution of the unprotected peptide. In case of attachment of the protracting moiety and/or linker to the protected peptidyl resin the attachment can be modular using SPPS and suitably protected building blocks.

Method: SC_P

The N-ε-lysine protection group was removed as described above and the chemical modification of the lysine was performed by one or more automated steps on the Prelude peptide synthesiser using suitably protected building blocks as described above. Double couplings were performed as described in SPPS_P with 3 hours per coupling.

Method: SC_L

The N-ε-lysine protection group was removed as described above and the chemical modification of the lysine was performed by one or more automated steps on the Liberty peptide synthesiser using suitably protected building blocks as described above. Double couplings were performed as described in SPPS_L.

Method: SC_A

The N-ε-lysine protection group was removed as described above and the chemical modification of the lysine was performed by one or more automated steps on the ABI peptide synthesiser using suitably protected building blocks as described in SPPS_A.

Method: SC_M1

The N-ε-lysine protection group was removed as described above. Activated (active ester or symmetric anhydride) protracting moiety or linker such as octadecanedioic acid mono-(2,5-dioxo-pyrrolidin-1-yl) ester (Ebashi et al. EP511600, 4 molar equivalents relative to resin bound peptide) was dissolved in NMP (25 mL), added to the resin and shaken overnight at room temperature. The reaction mixture was filtered and the resin was washed extensively with NMP, DCM, 2-propanol, methanol and diethyl ether.

Method: SC_M2

The N-ε-lysine protection group was removed as described above. The protracting moiety was dissolved in NMP/DCM (1:1, 10 ml). The activating reagent such as HOBt or Oxyma Pure® (4 molar equivalents relative to resin) and DIC (4 molar equivalents relative to resin) was added and the solution was stirred for 15 min. The solution was added to the resin and DIPEA (4 molar equivalents relative to resin) was added. The resin was shaken 2 to 24 hours at room temperature. The resin was washed with NMP (2×20 ml), NMP/DCM (1:1, 2×20 ml) and DCM (2×20 ml).

Method: SC_M3

Activated (active ester or symmetric anhydride) protracting moiety or linker such as octadecanedioic acid mono-(2,5-dioxo-pyrrolidin-1-yl) ester (Ebashi et al. EP511600) 1-1.5 molar equivalents relative to the peptide was dissolved in an organic solvent such as acetonitrile, THF, DMF, DMSO or in a mixture of water/organic solvent (1-2 ml) and added to a solution of the peptide in water (10-20 ml) together with 10 molar equivalents of DIPEA. In case of protecting groups on the protracting moiety such as tert-butyl, the reaction mixture was lyophilised overnight and the isolated crude peptide deprotected afterwards. In case of tert-butyl protection groups the deprotection was performed by dissolving the peptide in a mixture of trifluoroacetic acid, water and triisopropylsilane (90:5:5). After 30 min the mixture was evaporated in vacuo and the crude peptide purified by preparative HPLC as described later.

4. Cleavage of Resin Bound Peptide with or without Attached Side Chains and Purification Method: CP_M1

After synthesis the resin was washed with DCM, and the peptide was cleaved from the resin by a 2-3 hour treatment with TFA/TIS/water (95/2.5/2.5 or 92.5/5/2.5) followed by precipitation with diethylether. The peptide was dissolved in a suitable solvent (such as, e.g., 30% acetic acid) and purified by standard RP-HPLC on a C18, 5 µM column, using acetonitrile/water/TFA. The fractions were analysed by a combination of UPLC, MALDI and LCMS methods, and the appropriate fractions were pooled and lyophilised.

Method: CP_L1

After synthesis the resin was washed with DCM, and the peptide was cleaved from the resin by the use of a CEM Accent Microwave Cleavage System (CEM Corp., North Carolina). Cleavage from the resin was performed at 38° C. for 30 minutes by the treatment with TFA/TIS/water (95/2.5/2.5) followed by precipitation with diethylether. The peptide was dissolved in a suitable solvent (such as, e.g., 30% acetic acid) and purified by standard RP-HPLC on a C18, 5 µM column, using acetonitrile/water/TFA. The fractions were analysed by a combination of UPLC, MALDI and LCMS methods, and the appropriate fractions were pooled and lyophilised.

A2. General Methods for Detection and Characterisation

1. LC-MS Methods

Method: LCMS01v1

LCMS01v1 was performed on a setup consisting of Waters Acquity UPLC system and LCT Premier XE mass spectrometer from Micromass. Eluents: A: 0.1% Formic acid in water B: 0.1% Formic acid in acetonitrile The analysis was performed at RT by injecting an appropriate volume of the sample (preferably 2-10 µl) onto the column which was eluted with a gradient of A and B. The UPLC conditions, detector settings and mass spectrometer settings were: Column: Waters Acquity UPLC BEH, C-18, 1.7 µm, 2.1 mm×50 mm. Gradient: Linear 5%-95% acetonitrile during 4.0 min (alternatively 8.0 min) at 0.4 ml/min. Detection: 214 nm (analogue output from TUV (Tunable UV detector)) MS ionisation mode: API-ES Scan: 100-2000 amu (alternatively 500-2000 amu), step 0.1 amu.

2. UPLC Methods

Method: UPLC02v1

The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing: A: 99.95% $H_2O$, 0.05% TFA; B: 99.95% $CH_3CN$, 0.05% TFA. The following linear gradient was used: 95% A, 5% B to 95% A, 5% B over 16 minutes at a flow-rate of 0.40 ml/min.

Method: UPLC07v1

The RP-analysis was performed using a Waters UPLC system fitted with a dual band detector. UV detections at 215 nm and 254 nm were collected using an kinetex 1.7 u C18, 100A 2.1×150 mm column, 60° C. The UPLC system was connected to two eluent reservoirs containing: A: 90% water and 10% $CH_3CN$ with 0,045M $(NH_4)_2HPO_4$, pH 3.6, B: 20% isopropanole, 20% water and 60% $CH_3CN$. The following step gradient was used: 35% B and 65% A over 2 minutes, then 35% B, 65% A to 65% B, 35% A over 15 minutes, then 65% B, 35% A to 80% B, 20% A over 3 minutes at a flowrate of 0.5 ml/min.

Method: UPLC06v1

The RP-analysis was performed using a Waters UPLC system fitted with a dual band detector. UV detections at 215 nm and 254 nm were collected using an kinetex 1.7 u C18, 100A 2.1×150 mm column, 60° C. The UPLC system was connected to two eluent reservoirs containing: A: 90% water and 10% MeCN with 0.045M $(NH_4)_2HPO_4$, pH 3.6, B: 20% isopropanole, 20% water and 60% $CH_3CN$. The following step gradient was used: 25% B and 75% A over 2 minutes, then 25% B, 75% A to 55% B, 45% A over 15 minutes, then 55% B, 45% A to 80% B, 20% A over 3 minutes at a flowrate of 0.5 ml/min.

3. MALDI-MS Method

Method: MALDI01v1

Molecular weights were determined using matrix-assisted laser desorption and ionisation time-of-flight mass spectroscopy, recorded on a Microflex or Autoflex (Bruker). A matrix of alpha-cyano-4-hydroxy cinnamic acid was used.

B. Example Compounds

Example 1

$N^{\varepsilon 26}$-[(2S)-2-amino-6-[[(2S)-2-amino-6-[[(4 S)-4-carboxy-4-[10-(4-carboxyphenoxy)decanoylamino]butanoyl]amino]hexanoyl]amino]hexanoyl], $N^{\varepsilon 34}$-[(2S)-2-amino-6-[[(2S)-2-amino-6-[[(4S)-4-carboxy-4-[10-(4-carboxyphenoxy)decanoylamino]butanoyl]amino]hexanoyl]amino]hexanoyl]-[Aib$^8$]-GLP-1-(7-37)-peptide (SEQ ID NO: 4)

Chem. 21

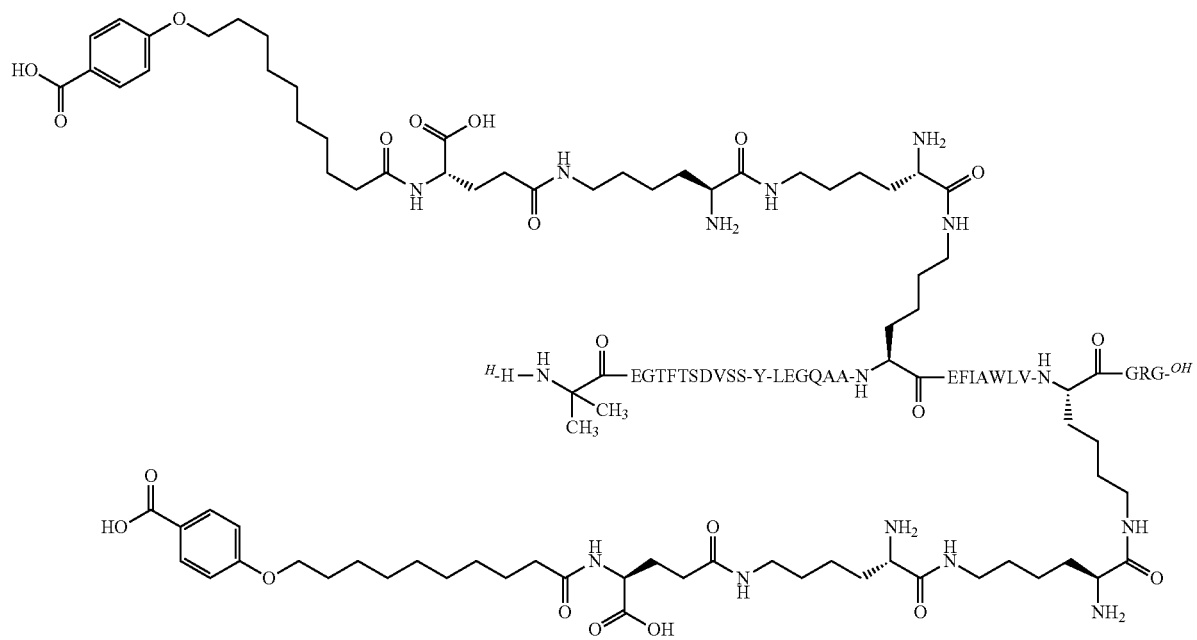

Preparation method: SPPS_P; SC_P; CP_M1
MALDI01v01: calc. m/z: 4721 found m/z: 4720
UPLC Method: UPLC07v1: Rt=9.2 min
UPLC Method: UPLC02v1: Rt=7.8 min

Example 2

N$^{\varepsilon26}$-[(2S)-2-amino-6-[[2-[2-[2-[[2-[2-[2-[[(4S)-4-carboxy-4-[12-(4-carboxyphenoxy)dodecanoylamino]butanoyl]amino]ethoxy]ethoxy]acetyl]amino]ethoxy]ethoxy]acetyl]amino]hexanoyl], N$^{\varepsilon34}$-[(2S)-2-amino-6-[[2-[2-[2-[[2-[2-[2-[[(4S)-4-carboxy-4-[12-(4-carboxyphenoxy)dodecanoylamino]butanoyl]amino]ethoxy]ethoxy]acetyl]amino]ethoxy]ethoxy]acetyl]amino]hexanoyl]-[Aib$^8$]-GLP-1-(7-37)-peptide (SEQ ID NO: 4)

Chem. 22

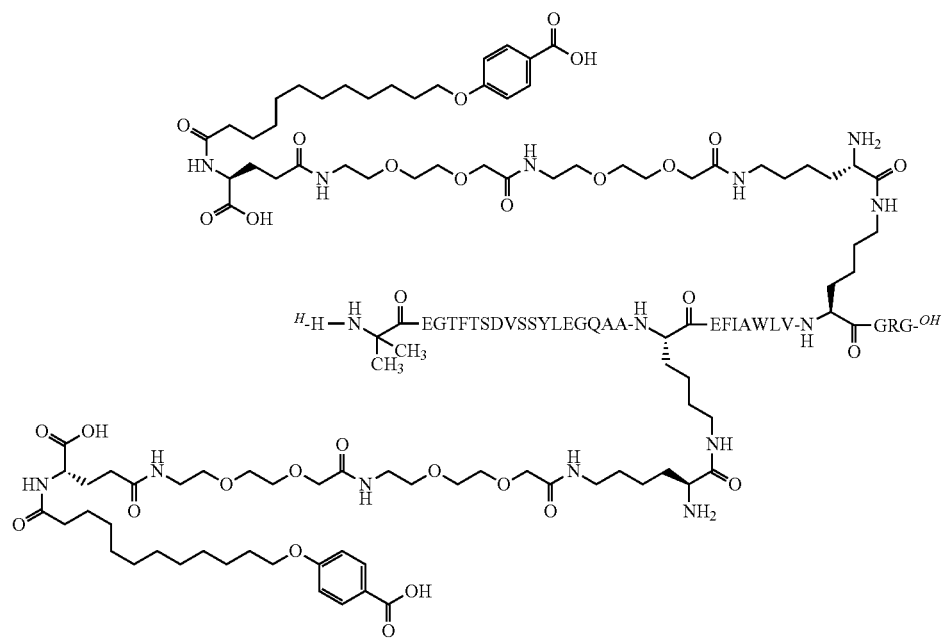

Preparation method: SPPS_P; SC_P; CP_M1
MALDI01v01: calc. m/z: 5101.8 found m/z: 5100.3
UPLC Method: UPLC07v01: Rt=12.9 min

Example 3

$N^{\varepsilon 26}$-[(2S)-2-amino-6-[[(2S)-2-amino-6-[[(4S)-4-carboxy-4-[12-(4-carboxyphenoxy)dodecanoylamino]butanoyl]amino]hexanoyl]amino]hexanoyl], $N^{\varepsilon 34}$-[(2S)-2-amino-6-[[(2S)-2-amino-6-[[(4S)-4-carboxy-4-[12-(4-carboxyphenoxy)dodecanoylamino]butanoyl]amino]hexanoyl]amino]hexanoyl]-[Imp$^7$,Aib$^8$]-GLP-1-(7-37)-peptide (SEQ ID NO: 5)

Chem. 23

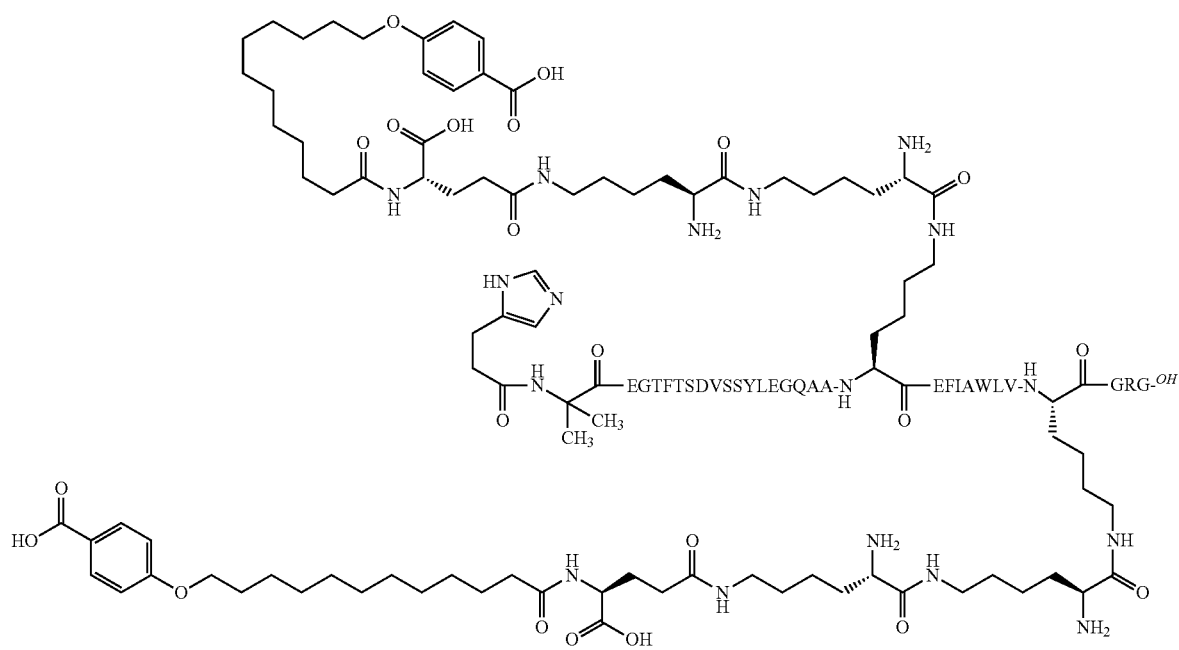

Preparation method: SPPS_P; SC_P; CP_M1
MALDI01v01: calc. m/z: 4762.5 found m/z: 4759.4
UPLC Method: UPLC07v01: Rt=13.2 min

Example 4

$N^{\epsilon 26}$-[(2S)-2-amino-6-[[2-[2-[2-[[2-[2-[2-[[(4S)-4-carboxy-4-[12-(4-carboxyphenoxy)dodecanoylamino]butanoyl]amino]ethoxy]ethoxy]acetyl]amino]ethoxy]ethoxy]acetyl]amino]hexanoyl], $N^{\epsilon 34}$-[(2S)-2-amino-6-[[2-[2-[[2-[2-[2-[[(4S)-4-carboxy-4-[12-(4-carboxyphenoxy)dodecanoylamino]butanoyl]amino]ethoxy]ethoxy]acetyl]amino]ethoxy]ethoxy]acetyl]amino]hexanoyl]-GLP-1-(7-37)-peptide (SEQ ID NO: 1)

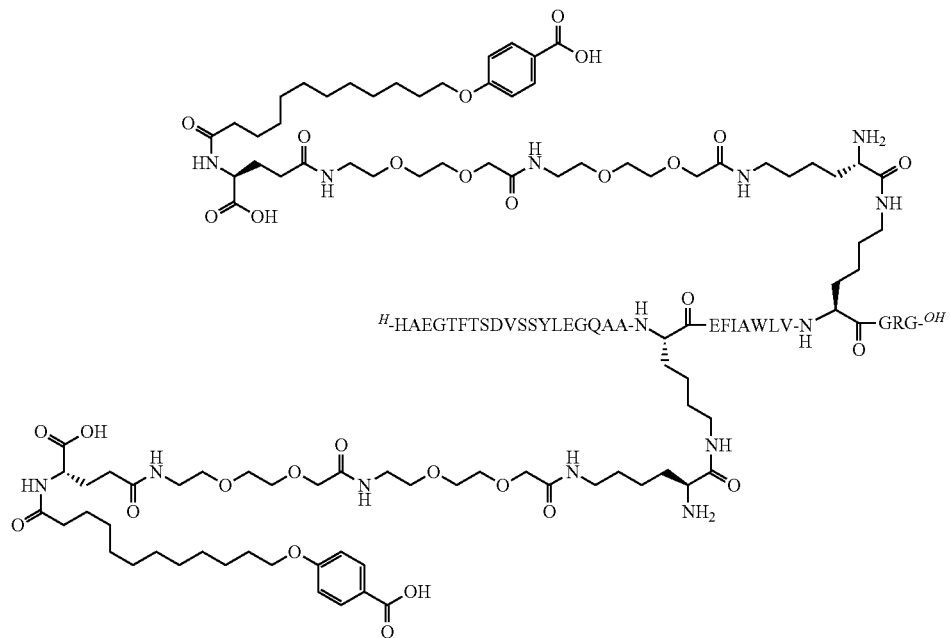

Chem. 24

Preparation method: SPPS_P; SC_P; CP_M1
MALDI01v01: calc. m/z: 5087.8 found m/z: 5086.1
UPLC Method: UPLC07v01: Rt=12.6 min

Example 5

N^ε26^-[(2S)-2-amino-6-[[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]amino]hexanoyl], N^ε34^-[(2S)-2-amino-6-[[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]amino]hexanoyl]-GLP-1-(7-37)-peptide (SEQ ID NO: 1)

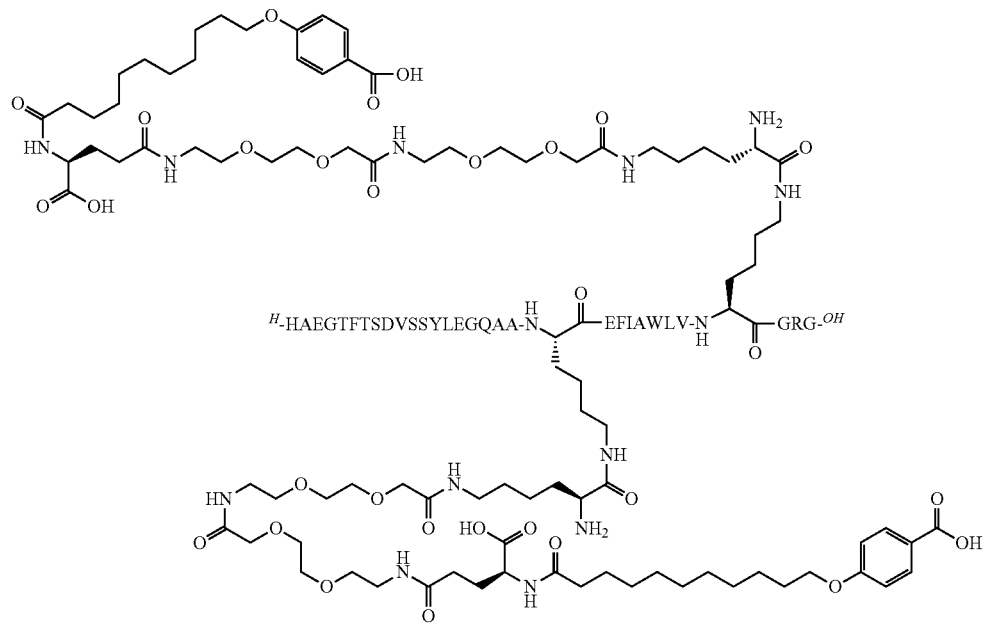

Chem. 25

Preparation method: SPPS_P; SC_P; CP_M1
MALDI01v01: calc. m/z: 5059.7 found m/z: 5057.5
UPLC Method: UPLC07v01: Rt=11.1 min

Example 6

N^ε26^-[(2S)-2-amino-6-[[(2S)-2-amino-6-[[2-[2-[2-[[2-[2-[2-[[(4S)-4-carboxy-4-[12-(4-carboxyphenoxy)dodecanoylamino]butanoyl]amino]ethoxy]ethoxy]acetyl]amino]ethoxy]ethoxy]acetyl]amino]hexanoyl]amino]hexanoyl], N^ε34^-[(2S)-2-amino-6-[[(2S)-2-amino-6-[[2-[2-[2-[[2-[2-[2-[[(4S)-4-carboxy-4-[12-(4-carboxyphenoxy)dodecanoylamino]butanoyl]amino]ethoxy]ethoxy]acetyl]amino]ethoxy]ethoxy]acetyl]amino]hexanoyl]amino]hexanoyl]-[Aib⁸]-GLP-1-(7-37)-peptide
(SEQ ID NO: 4)

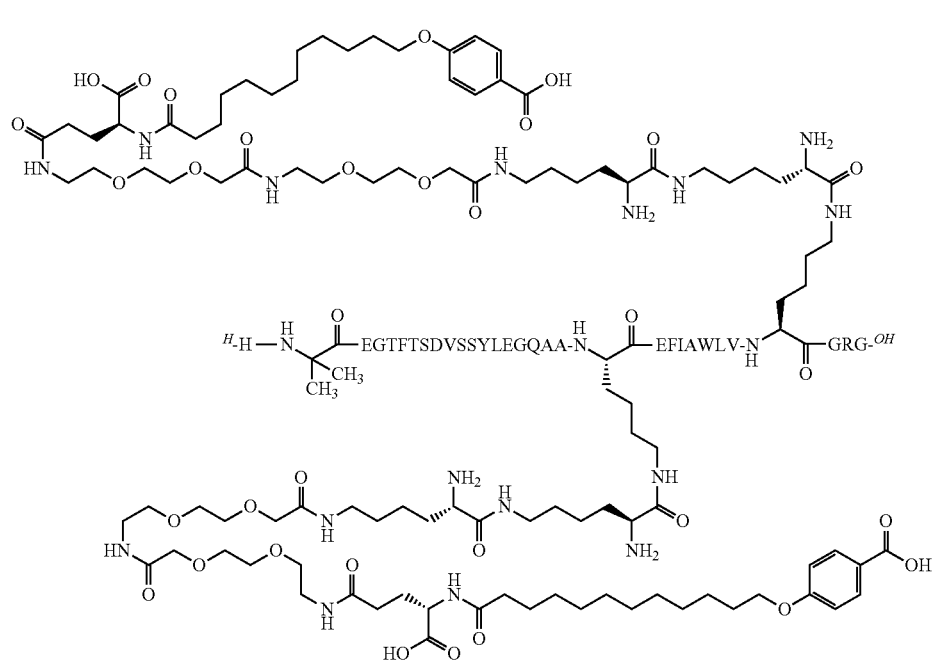

Chem. 26

Preparation method: SPPS_P; SC_P; CP_M1
MALDI01v01: calc. m/z: 5358.2 found m/z: 5356.2
UPLC Method: UPLC07v01: Rt=11.3 min

Example 7

N$^{\varepsilon 26}$-[(2S)-2-amino-6-[[(2S)-2-amino-6-[[2-[2-[2-[[2-[2-[2-[[(4S)-4- carboxy-4-[11-(4-carboxyphenoxy)undecanoylamino]butanoyl]amino]ethoxy]ethoxy]acetyl]amino]ethoxy]ethoxy]acetyl]amino]hexanoyl]amino]hexanoyl], N$^{\varepsilon 34}$-[(2S)-2-amino-6-[[(2S)-2-amino-6-[[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]amino]hexanoyl]amino]hexanoyl]-[Aib$^8$]-GLP-1-(7-37)-peptide
(SEQ ID NO: 4)

Chem. 27

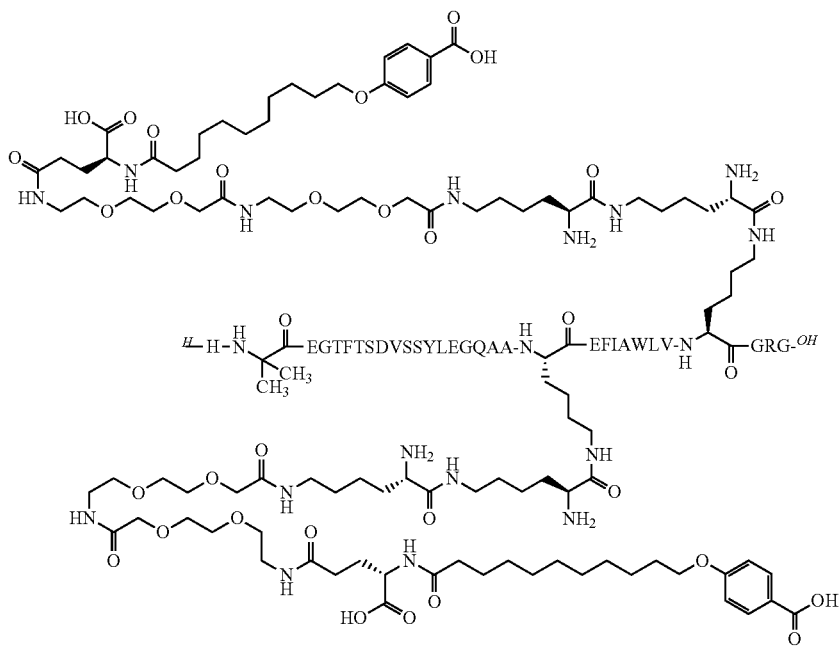

Preparation method: SPPS_P; SC_P; CP_M1
MALDI01v01: calc. m/z: 5330.1 found m/z: 5328.8
UPLC Method: UPLC07v01: Rt=9.8 min

Example 8

N$^{\epsilon 26}$-[(2S)-2-amino-6-[[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]amino]hexanoyl], N$^{\epsilon 34}$-[(2S)-2-amino-6-[[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]amino]hexanoyl]-[Aib$^8$]-GLP-1-(7-37)-peptide (SEQ ID NO: 4)

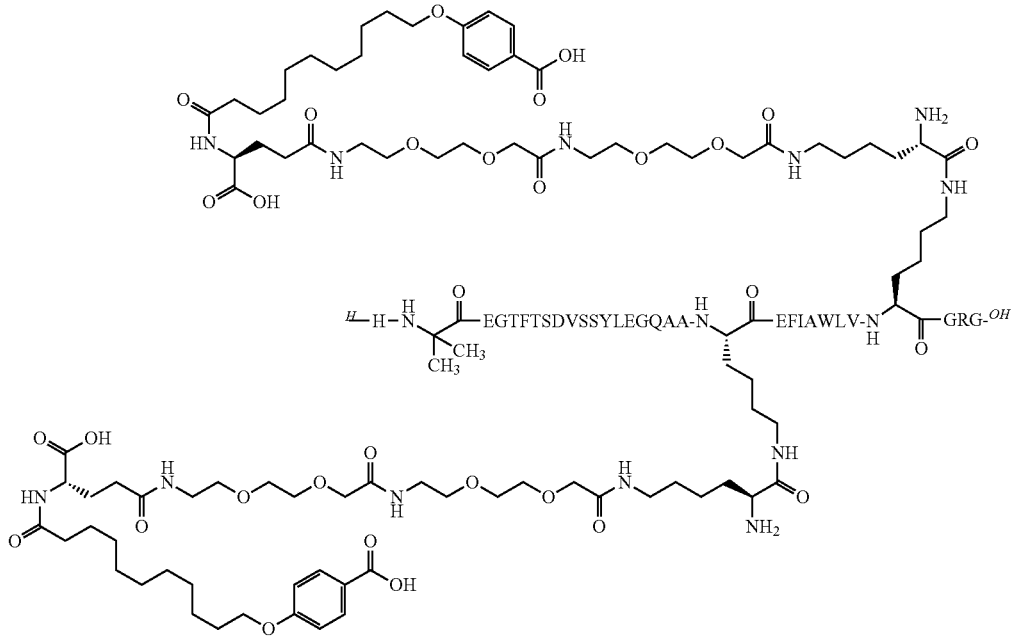

Chem. 28

Preparation method: SPPS_P; SC_L; SC_M1; CP_M1

LCMS Method: LCMS01v01: m/z: found m/3 1692, m/4 1269, m/5 1016; Rt=2.17 min

UPLC Method: UPLC07v01: Rt=11.5 min

Example 9

N$^{\varepsilon 26}$-[(2S)-2-amino-6-[[2-[2-[2-[[2-[2-[2-[[(4S)-4-carboxy-4-[12-(4-carboxyphenoxy)dodecanoylamino]butanoyl]amino]ethoxy]ethoxy]acetyl]amino]ethoxy]ethoxy]acetyl]amino]hexanoyl], N$^{\varepsilon 34}$-[(2S)-2-amino-6-[[2-[2-[[2-[2-[2-[[(4S)-4-carboxy-4-[12-(4-carboxyphenoxy)dodecanoylamino]butanoyl]amino]ethoxy]ethoxy]acetyl]amino]ethoxy]ethoxy]acetyl]amino]hexanoyl]-[Aib$^8$,Glu$^{22}$]-GLP-1-(7-37)-peptide (SEQ ID NO: 6)

Chem. 29

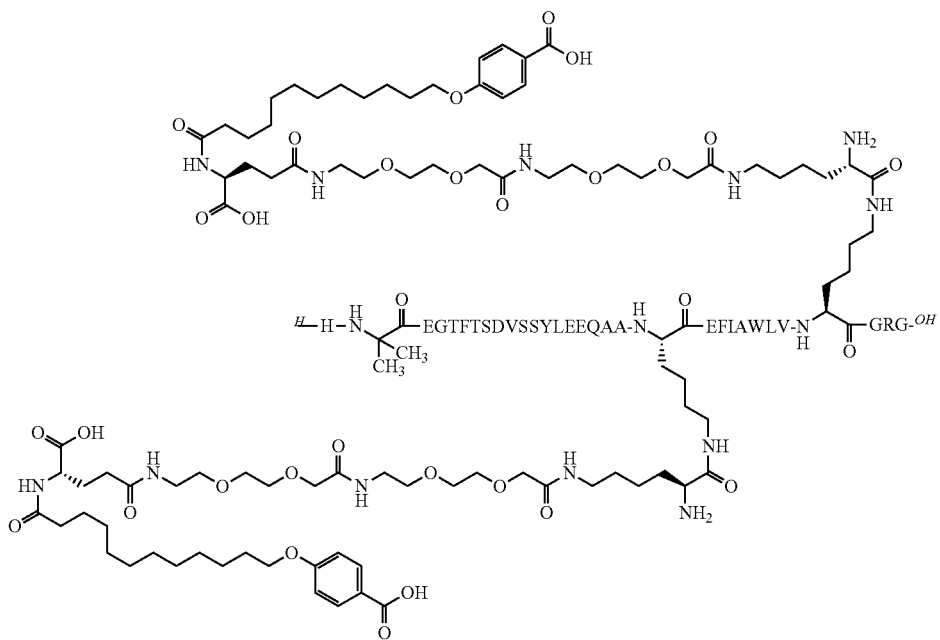

Preparation method: SPPS_P; SC_P; CP_M1
MALDI01v01: calc. m/z: 5173.8 found m/z: 5170.4
UPLC Method: UPLC07v01: Rt=12.9 min

Example 10

N^ε26-[(2S)-2-amino-6-[[2-[2-[2-[[2-[2-[2-[[(4S)-4-carboxy-4-[12-(4-carboxyphenoxy)dodecanoylamino]butanoyl]amino]ethoxy]ethoxy]acetyl]amino]ethoxy]ethoxy]acetyl]amino]hexanoyl], N^ε34-[(2S)-2-amino-6-[[2-[2-[2-[[2-[2-[2-[[(4S)-4-carboxy-4-[12-(4-carboxyphenoxy)dodecanoylamino]butanoyl]amino]ethoxy]ethoxy]acetyl]amino]ethoxy]ethoxy]acetyl]amino]hexanoyl]-[Aib$^8$,Glu$^{22}$,Glu$^{30}$]-GLP-1-(7-37)-peptide (SEQ ID NO: 7)

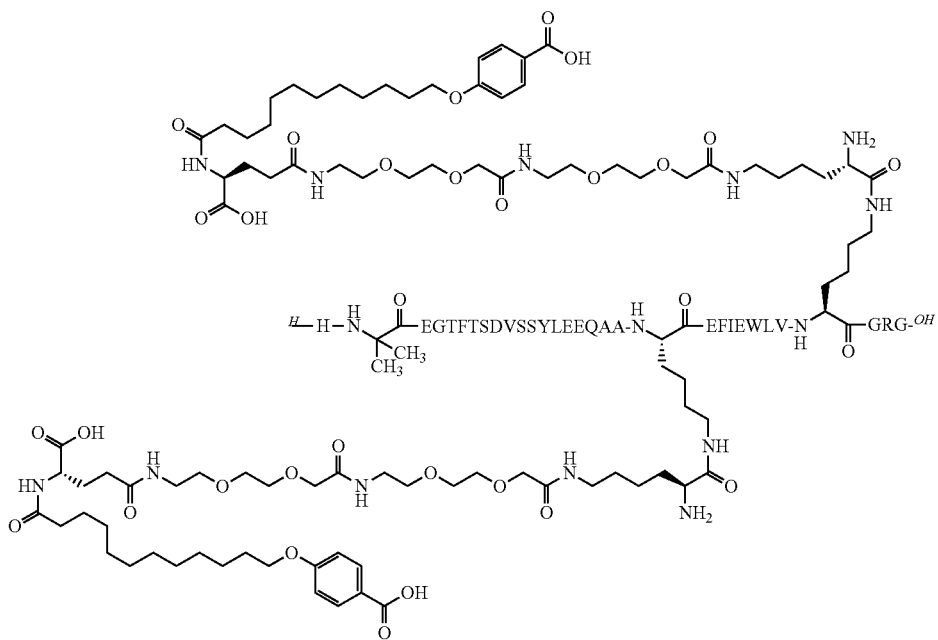

Chem. 30

Preparation method: SPPS_P; SC_P; CP_M1
MALDI01v01: calc. m/z: 5231.9 found m/z: 5230.5
UPLC Method: UPLC07v01: Rt=13.2 min

Example 11
N$^{\varepsilon26}$-[(2S)-2-amino-6-[[(2S)-2-amino-6-[[(4S)-4-carboxy-4-[11-(4-carboxyphenoxy)undecanoylamino]butanoyl]amino]hexanoyl]amino]hexanoyl], N$^{\varepsilon34}$-[(2S)-2-amino-6-[[(2S)-2-amino-6-[[(4S)-4-carboxy-4-[11-(4-carboxyphenoxy)undecanoylamino]butanoyl]amino]hexanoyl]amino]hexanoyl]-[Aib$^8$]-GLP-1-(7-37)-peptide (SEQ ID NO: 4)
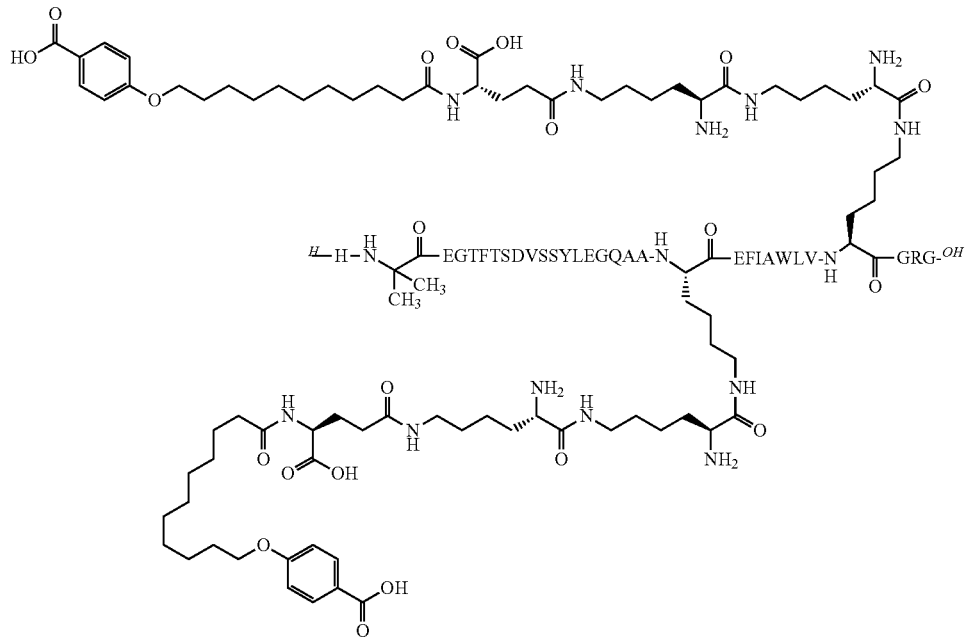
Chem. 31
Preparation method: SPPS_P; SC_P; CP_M1
MALDI01v01: calc. m/z: 4749.5 found m/z: 4749.6
UPLC07v01: Rt=11.4 min

Example 12

$N^{\varepsilon 26}$-[(2S)-2-amino-6-[[(2S)-2-amino-6-[[(4S)-4-carboxy-4-[12-(4-carboxyphenoxy)dodecanoylamino]butanoyl]amino]hexanoyl]amino]hexanoyl], $N^{\varepsilon 34}$-[(2S)-2-amino-6-[[(2S)-2-amino-6-[[(4S)-4-carboxy-4-[12-(4-carboxyphenoxy)dodecanoylamino]butanoyl]amino]hexanoyl]amino]hexanoyl]-[Aib$^8$]-GLP-1-(7-37)-peptide (SEQ ID NO: 4)

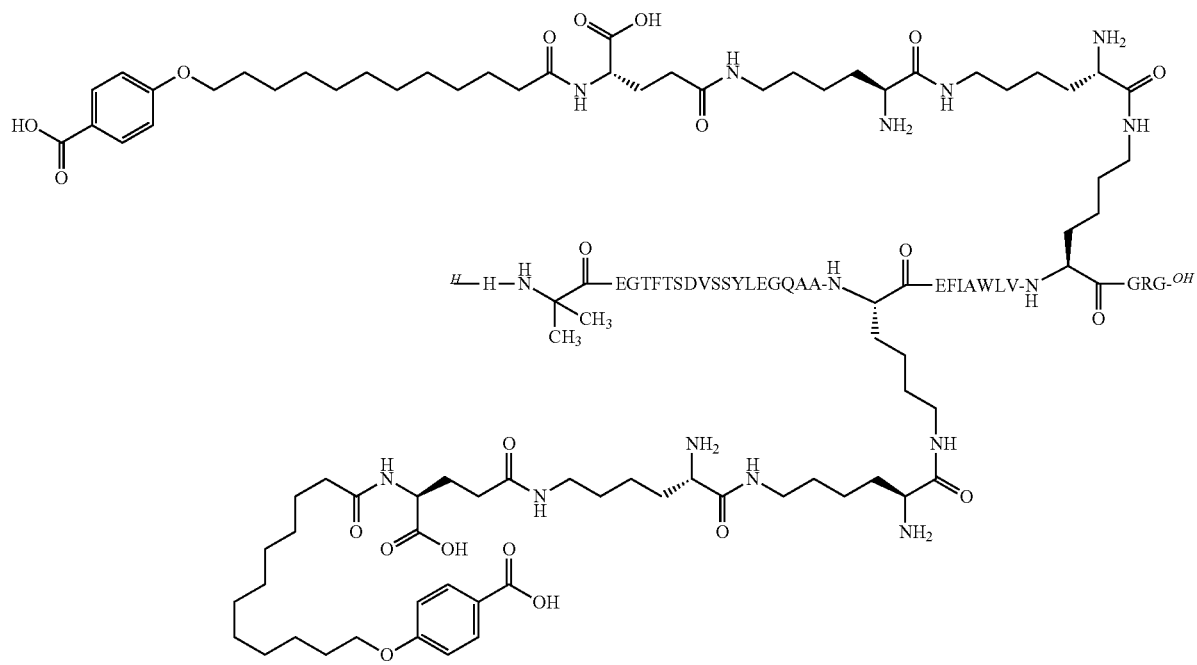

Chem. 32

Preparation method: SPPS_P; SC_P; CP_M1
MALDI01v01: calc. m/z: 4777.4 found m/z: 4777.5
UPLC Method: UPLC07v01: Rt=13.2 min

Example 13

N^ε26-[(2S)-6-[[(2S)-6-[[(4S)-4-carboxy-4-[12-(4-carboxyphenoxy)dodecanoylamino]butanoyl]amino]-2-(dimethylamino)hexanoyl]amino]-2-(dimethylamino)hexanoyl], N^ε34-[(2S)-6-[[(2S)-6-[[(4S)-4-carboxy-4-[12-(4-carboxyphenoxy)dodecanoylamino]butanoyl]amino]-2-(dimethylamino)hexanoyl]amino]-2-(dimethylamino)hexanoyl]-[Imp^7,Aib^8]-GLP-1-(7-37)-peptide (SEQ ID NO: 5)

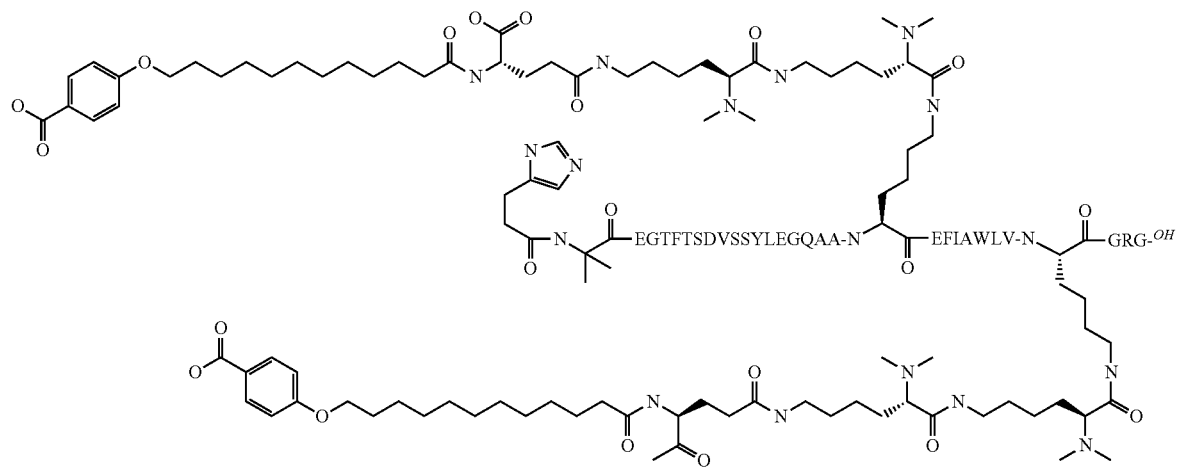

Chem. 33

Preparation Method:

To a 2 M aqueous AcOH solution containing 10% NMP (3 ml) of the compound in Example 3 (14500 nmol) was added formaldehyde (25 ul, 37%). The mixture was stirred for 10 min and a 1 M solution of α-picoline borane complex in NMP (150 ul) was added. The mixture was stirred for 40 min. After complete conversion the pH was raised to about 11.5 with 1 M NaOH and stirred for 30 min. Then pH was adjusted to 7.4 with 1 N HCl. The solution was diluted with 45 ml H$_2$O and purified with standard RP-HPLC on a C18, 5 μM column, using acetonitrile/water/TFA. The fractions were analysed by a combination of UPLC, MALDI and LCMS methods, and the appropriate fractions were pooled and lyophilised.

UPLC Method: UPLC02v1: Rt=9.1 min

LCMS Method: LCMS01v1: Rt=2.2 min, m/z 1625 (m/3), 1219 (m/4), 975 (m/5), 813 (m/6)

Example 14

N^ε26^-[(2S)-2-amino-6-[[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethxy]acetyl]amino]hexanoyl], N^ε34^-[(2S)-2-amino-6-[[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]amino]hexanoyl]-[Aib$^8$,Glu$^{22}$,Glu$^{30}$]-GLP-1-(7-37)-peptide (SEQ ID NO: 7) o

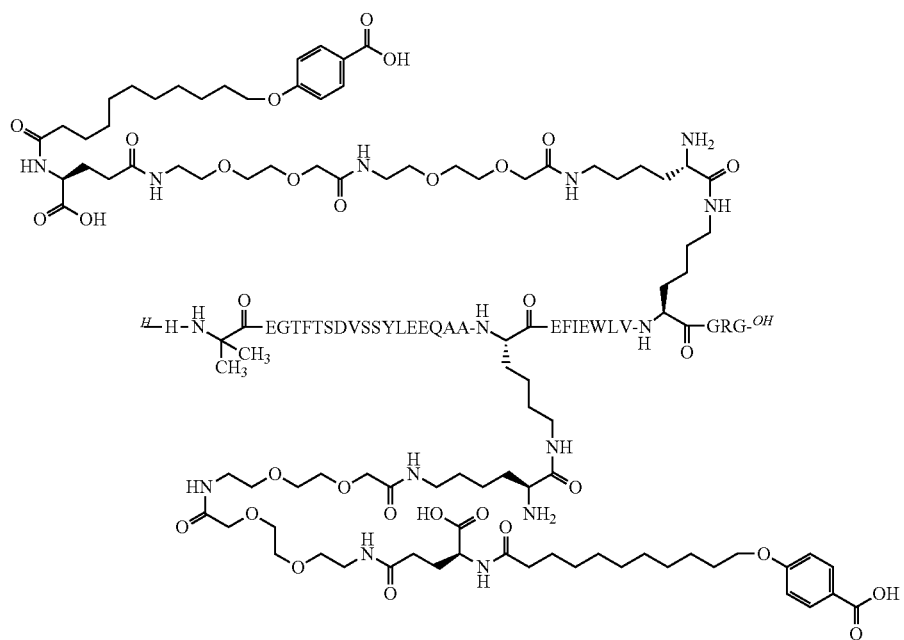

Chem. 34

Preparation method: SPPS_P; SC_P; CP_M1
UPLC Method: UPLC02v1: Rt=8.5 min
MALDI01v1: calc. m/z: 5203.9 found m/z: 5204.3

Example 15

$N^{\epsilon 26}$-[(2S)-2-amino-6-[[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]amino]hexanoyl], $N^{\epsilon 34}$-[(2S)-2-amino-6-[[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]amino]hexanoyl]-[Aib$^8$,Glu$^{22}$]-GLP-1-(7-37)-peptide (SEQ ID NO: 6)

Chem. 35

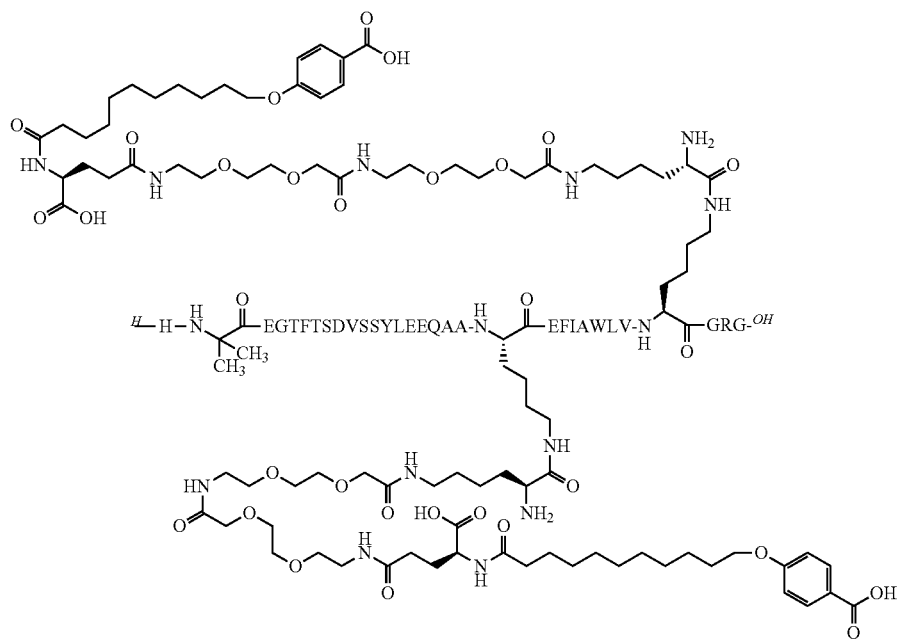

Preparation method: SPPS_P; SC_P; CP_M1
UPLC Method: UPLC02v1: Rt=8.6 min
MALDI01v1: calc. m/z: 5145.8  found m/z: 5146.6

Example 16
N^ε26^-[(2S)-2-amino-6-[[(2S)-2-amino-6-[[(4S)-4-carboxy-4-[10-(3-carboxyphenoxy)decanoylamino]butanoyl]amino]hexanoyl]amino]hexanoyl], N^ε34^-[(2S)-2-amino-6-[[(2S)-2-amino-6-[[(4S)-4-carboxy-4-[10-(3-carboxyphenoxy)decanoylamino]butanoyl]amino]hexanoyl]amino]hexanoyl]-[Aib⁸]-GLP-1-(7-37)-peptide (SEQ ID NO: 4)
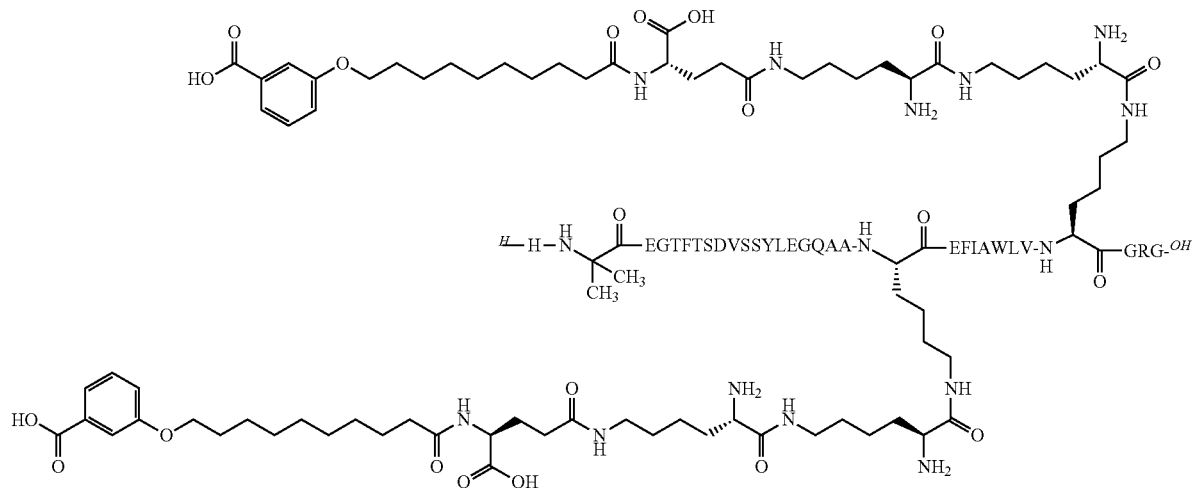
Chem. 36
Preparation method: SPPS_P; SC_M2; CP_M1
UPLC Method: UPLC02v1: Rt=8.2 min
LCMS01v1: Rt=1.7 min, m/z 1574 (m/3), 1181 (m/4), 945 (m/5), 788 (m/6)

Example 17
N^ε26-[(2S)-2-amino-6-[[(2S)-2-amino-6-[[(4S)-4-carboxy-4-[11-(4-carboxyphenoxy)undecanoylamino]butanoyl]amino]hexanoyl]amino]hexanoyl], N^ε34-[(2S)-2-amino-6-[[(2S)-2-amino-6-[[(4S)-4-carboxy-4-[11-(4-carboxyphenoxy)undecanoylamino]butanoyl]amino]hexanoyl]amino]hexanoyl]-[Imp⁷,Aib⁸]-GLP-1-(7-37)-peptide (SEQ ID NO: 5)
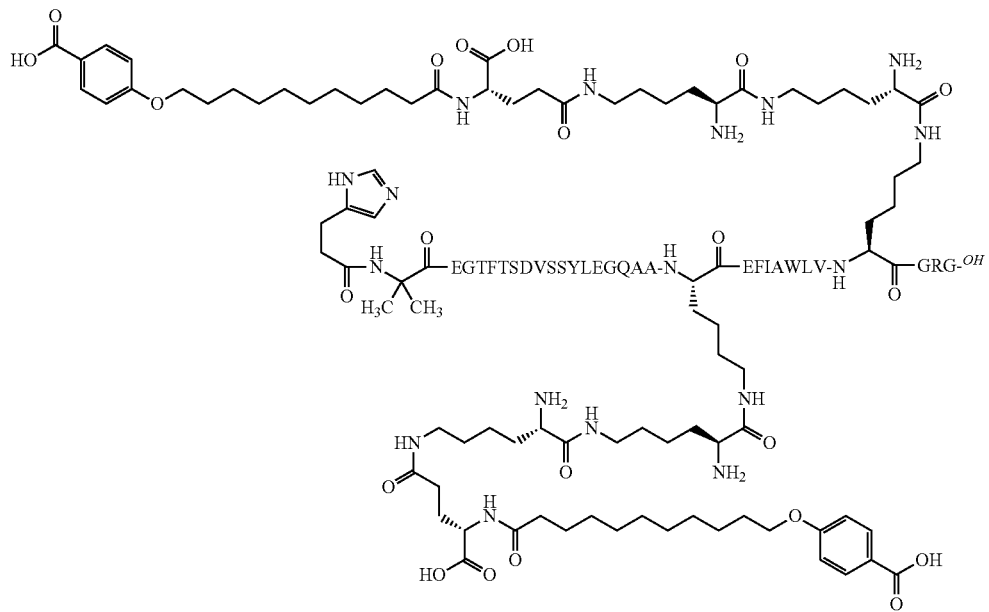
Chem. 37
Preparation method: SPPS_P; SC_P; CP_M1
UPLC method: UPLC01v1: Rt=12.56 min
LCMS method: LCMS01v1: Rt=2.1 min, m/z 1578 (m/3), 1184 (m/4), 947 (m/5)

Example 18

N^ε26-[(2S)-2-amino-6-[[(2S)-2-amino-6-[[(4S)-4-carboxy-4-[11-(4-carboxyphenoxy)undecanoylamino]butanoyl]amino]hexanoyl]amino]hexanoyl], N^ε34-[(2S)-2-amino-6-[[(2S)-2-amino-6-[[(4S)-4-carboxy-4-[11-(4-carboxyphenoxy)undecanoylamino]butanoyl]amino]hexanoyl]amino]hexanoyl]-GLP-1-(7-37)-peptide (SEQ ID NO: 1)

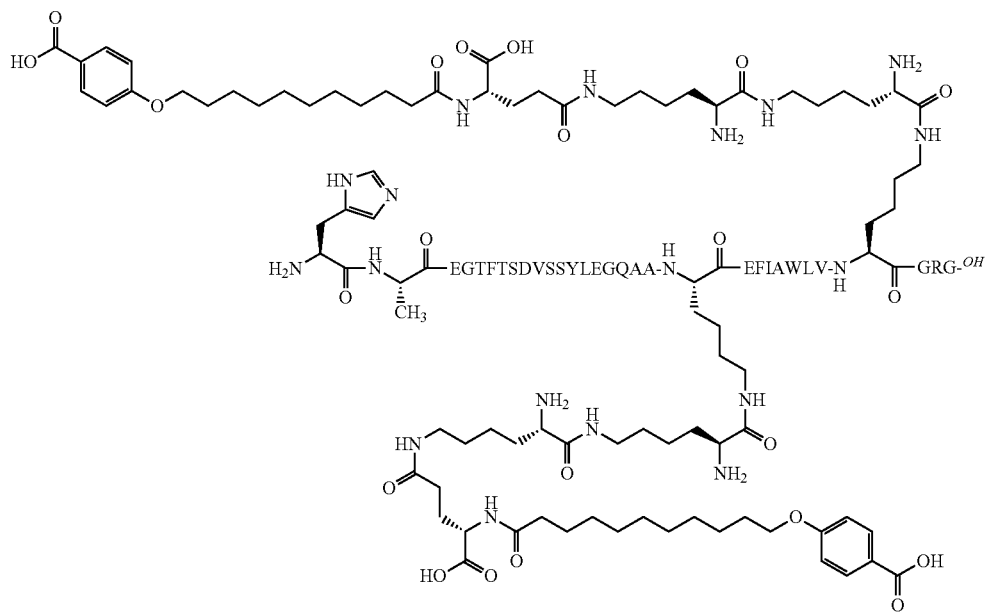

Chem. 38

Preparation method: SPPS_P; SC_P; CP_M1

UPLC method: UPLC01v1, Rt=12.08 min

LCMS method: LCMS01v1: Rt=2.0 min, m/z 1579 (m/3), 1185 (m/4), 948 (m/5)

Example 19

(S)-2-Dimethylamino-6-(9H-fluoren-9-ylmethoxycarbonylamino)-hexanoic acid

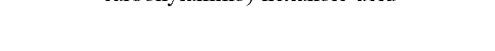

Chem. 39

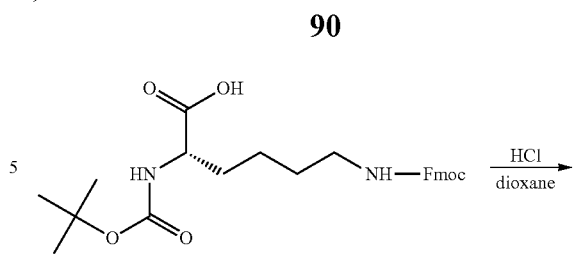

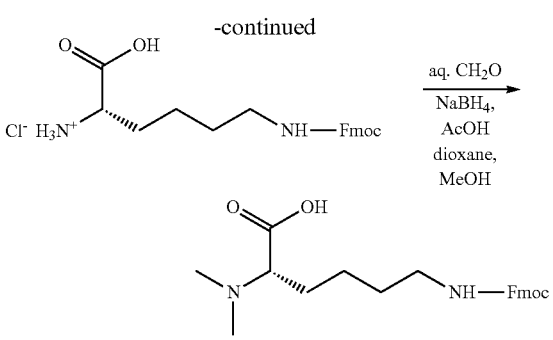

The compound of Chem. 39 is prepared as follows (further detail below):

The starting material, (S)-2-tert-Butoxycarbonylamino-6-(9H-fluoren-9-ylmethoxycarbonylamino)-hexanoic acid (Novabiochem F04-12-0069; 28.0 g, 59.8 mmol), was suspended in 1,4-dioxane (800 mL) and a solution of hydrogen chloride in 1,4-dioxane (7.2 M, 500 mL) was added and the resulting suspension was stirred at room temperature overnight. Then it was filtered and thoroughly washed with 1,4-dioxane and diethylether prior to drying in vacuo. The hydrochloride of (S)-2-amino-6-(9H-fluoren-9-ylmethoxycarbonylamino)hexanoic acid was obtained as a white solid.

Yield: 23.58 g (96%)

NMR: 1H NMR spectrum (300 MHz, MeOD-d4, dH): 7.80 (d, J=7.4 Hz, 2H); 7.64 (d, J=7.4 Hz, 2H); 7.47-7.25 (m, 4H); 4.58-4.29 (m, 2H); 4.14-4.25 (m, 1H); 3.95 (t, J=6.3 Hz, 1H); 3.19-2.73 (m, 2H); 2.09-1.71 (m, 2H); 1.65-1.14 (m, 4H)

The product from the above reaction (13.1 g, 32.4 mmol) and an aqueous solution of formaldehyde (approx. 35%, 13.2 mL) were dissolved in a mixture of 1,4-dioxane/methanol (300 mL, 1:1) and the resulting solution was cooled down to 0° C. Then sodium borohydride (5.50 g, 145 mmol) was carefully added in three portions within 15 minutes and pH of the reaction mixture was adjusted by addition of acetic acid (14.4 mL) to pH 5.5. Then a second portion of aqueous formaldehyde (approx. 35%, 13.2 mL) was added into the reaction mixture and another part of sodium borohydride (5.50 g, 145 mmol) was carefully added in three portions. The reaction mixture was allowed to warm up to the room temperature and stirred for further 60 minutes. HPLC-MS analysis revealed full conversion of the starting material thus the reaction was quenched by addition of 10% aqueous sodium hydrogencarbonate solution (approx. 20 mL) until pH 7.0. Then the reaction mixture was diluted with saturated aqueous solution of sodium chloride and extracted with chloroform (5×500 mL). Fractions containing the desired product (TLC) were collected and dried with anhydrous magnesium sulfate. Then the solution was filtered and the solvents removed under reduced pressure. The crude product was dissolved in warm chloroform (300 mL) and a mixture of diethylether/hexane (2:1, 700 mL) was added. The formed precipitate was filtered, washed with diethylether prior to drying in vacuo to give the title compound as a white powder.

Yield: 14.26 g

LC-MS (Sunfire 4.6 mm×100 mm, acetonitrile/water 35:65 to 100:0+0.1% FA): Rt=3.71 min LC-MS m/z: 397.4 (M+H)+.

The collected crude product (36.5 g) from 3 batches of the above was subjected to RP-column chromatography (Cromasil C18, 100 Å, 13 µm. 7.5×41 cm, flow rate 200 mL/min, acetonitrile/water 20:80 to 45:55, detection UV 220 nm). Fractions containing the product were collected and freeze dried. (S)-2-Dimethylamino-6-(9H-fluoren-9-ylmethoxycarbonylamino)-hexanoic acid was obtained as fine white powder.

Yield: 20.21 g

NMR: 1H NMR spectrum (300 MHz, AcOD-d4, dH): 7.87-7.72 (m, 2H); 7.70-7.57 (m, 2H); 7.53-7.20 (m, 4H); 4.66-4.36 (m, 2H); 4.35-4.12 (m, 1H); 3.98-3.77 (m, 1H); 3.32-3.10 (m, 2H); 2.95 (s, 6H); 2.16-1.73 (m, 2H, overlapped); 1.69-1.16 (m, 4H)

LC-MS (Sunfire 4.6 mm×100 mm, acetonitrile/water 35:65 to 100:0+0.1% FA): Rt=3.11 min LC-MS m/z: 397.2 (M+H)+

This intermediate product may be used in the synthesis of the compound of Example 13 and other compounds with the same linker.

Pharmacological Methods

Example 20: In Vitro Potency (AlphaScreen; Membranes)

The purpose of this example is to test the activity, or potency, of the GLP-1 derivatives in vitro.

The potencies of the GLP-1 derivatives of Examples 1-3 were determined as described below, i.e. as the stimulation of the formation of cyclic AMP (cAMP) in a medium containing membranes expressing the human GLP-1 receptor.

Principle

Purified plasma membranes from a stable transfected cell line, BHK467-12A (tk-ts13), expressing the human GLP-1 receptor were stimulated with the GLP-1 analogue or derivative in question, and the potency of cAMP production was measured using the AlphaScreen™ cAMP Assay Kit from Perkin Elmer Life Sciences. The basic principle of the AlphaScreen Assay is a competition between endogenous cAMP and exogenously added biotin-cAMP. The capture of cAMP is achieved by using a specific antibody conjugated to acceptor beads.

Cell Culture and Preparation of Membranes

A stable transfected cell line and a high expressing clone were selected for screening. The cells were grown at 5% $CO_2$ in DMEM, 5% FCS, 1% Pen/Strep (Penicillin/Streptomycin) and 0.5 mg/ml of the selection marker G418.

Cells at approximately 80% confluence were washed 2× with PBS and harvested with Versene (aqueous solution of the tetrasodium salt of ethylenediaminetetraacetic acid), centrifuged 5 min at 1000 rpm and the supernatant removed. The additional steps were all performed on ice. The cell pellet was homogenised by the Ultrathurax for 20-30 s in 10 ml of Buffer 1 (20 mM Na-HEPES, 10 mM EDTA, pH=7.4), centrifuged 15 min at 20,000 rpm and the pellet resuspended in 10 ml of Buffer 2 (20 mM Na-HEPES, 0.1 mM EDTA, pH=7.4). The suspension was homogenised for 20-30 s and centrifuged 15 min at 20,000 rpm. Suspension in Buffer 2, homogenisation and centrifugation was repeated once and the membranes were resuspended in Buffer 2. The protein concentration was determined and the membranes stored at −80° C. until use.

The assay was performed in flat-bottom 96-well plates (Costar cat. no: 3693). The final volume per well was 50 µl.

Solutions and Reagents

AlphaScreen cAMP Assay Kit from Perkin Elmer Life Sciences (cat. No: 6760625M); containing Anti-cAMP Acceptor beads (10 U/µl), Streptavidin Donor beads (10 U/µl) and Biotinylated-cAMP (133 U/µl).

AlphaScreen Buffer, pH=7.4: 50 mM TRIS-HCl (Sigma, cat. no: T3253); 5 mM HEPES (Sigma, cat. no: H3375); 10 mM $MgCl_2$, $6H_2O$ (Merck, cat. no: 5833); 150 mM NaCl (Sigma, cat. no: S9625); 0.01% Tween (Merck, cat. no: 822184). The following was added to the AlphaScreen Buffer prior to use (final concentrations indicated): BSA (Sigma, cat. no. A7906): 0.1%; IBMX (Sigma, cat. no. 15879): 0.5 mM; ATP (Sigma, cat. no. A7699): 1 mM; GTP (Sigma, cat. no. G8877): 1 uM.

cAMP standard (dilution factor in assay=5): cAMP Solution: 5 µL of a 5 mM cAMP-stock+495 µL AlphaScreen Buffer.

Suitable dilution series in AlphaScreen Buffer were prepared of the cAMP standard as well as the GLP-1 analogue or derivative to be tested, e.g. the following eight concentrations of the GLP-1 compound: $10^{-7}$, $10^{-8}$, $10^{-9}$, $10^{-10}$, $10^{-11}$, $10^{-12}$, $10^{-13}$ and $10^{-14}$M, and a series from, e.g., $10^{-6}$ to $3×10^{-11}$ of cAMP.

Membrane/Acceptor Beads

Membranes were prepared from hGLP-1/BHK 467-12A cells with a concentration of 6 µg/well corresponding to 0.6 mg/ml (the amount of membranes used pr. well may vary)

"No membranes": Acceptor Beads (15 µg/ml final) in AlphaScreen buffer

"6 µg/well membranes": membranes+Acceptor Beads (15 µg/ml final) in AlphaScreen buffer An aliquot (10 µl) of "No membranes" was added to the cAMP standard (per well in duplicate wells) and the positive and negative controls An aliquot (10 µl) of "6 µg/well membranes" was added to GLP-1 and analogues (per well in duplicate or triplicate wells)

Pos. Control: 10 µl "no membranes"+10 µl AlphaScreen Buffer

Neg. Control: 10 µl "no membranes"+10 µl cAMP Stock Solution (50 µM)

As the beads are sensitive to direct light, any handling was in the dark (as dark as possible), or in green light. All dilutions were made on ice.

Procedure
1. Make the AlphaScreen Buffer.
2. Dissolve and dilute the GLP-1/Analogues/cAMP standard in AlphaScreen Buffer.
3. Make the Donor Beads Solution by mixing streptavidin donor beads (2 units/well) and biotinylated cAMP (1.2 units/well) and incubate 20-30 min in the dark at room temperature
4. Add the cAMP/GLP-1/Analogues to the plate: 10 µl per well.
5. Prepare membrane/Acceptor Beads solution and add this to the plates: 10 µl per well.
6. Add the Donor Beads: 30 µl per well.
7. Wrap the plate in aluminum foil and incubate on the shaker for 3 hours (very slowly) at RT.
8. Count on AlphaScreen—each plate pre incubates in the AlphaScreen for 3 minutes before counting.

Results

The $EC_{50}$ [pM] values were calculated using the GraphPad Prism software (version 5) and are shown in Table 1 below. The potency of all derivatives in vitro was confirmed.

TABLE 1

| In vitro potency (AlphaScreen; membranes) | |
|---|---|
| Compound of Example no. | $EC_{50}$/pM |
| 1 | 77 |
| 2 | 205 |
| 3 | 295 |

All derivatives except two had a good in vitro potency corresponding to an $EC_{50}$ of below 1200 pM.

For comparison, compound no. 13 in Table 1 of Journal of Medicinal Chemistry (2000), vol. 43, no. 9, p. 1664-669 (GLP-1(7-37) acylated at $K^{26,34}$ with bis-C12-diacid) had an in vitro potency corresponding to an $EC_{50}$ of 1200 pM.

Example 21: In Vitro Potency (CRE Luciferase; Whole Cells)

The purpose of this example is to test the activity, or potency, of the GLP-1 derivatives in vitro. The in vitro potency is the measure of human GLP-1 receptor activation in a whole cell assay.

The potencies of the GLP-1 derivatives of Examples 3-18 were determined as described below. Semaglutide was included for comparison.

Principle

In vitro potency was determined by measuring the response of human GLP-1 receptor in a reporter gene assay. The assay was performed in a stably transfected BHK cell line that expresses the human GLP-1 receptor and contains the DNA for the cAMP response element (CRE) coupled to a promoter and the gene for firefly luciferase (CRE luciferase). When the human GLP-1 receptor was activated it results in the production of cAMP, which in turn results in the luciferase protein being expressed. When assay incubation was completed the luciferase substrate (luciferin) was added and the enzyme converts luciferin to oxyluciferin and produces bioluminescence. The luminescence was measured and was the readout for the assay.

In order to test the binding of the derivatives to albumin, the assay was performed in the absence of serum albumin as well as in the presence of a considerably higher concentration of serum albumin (1.0% final assay concentration). An increase of the in vitro potency, $EC_{50}$ value, in the presence of serum albumin indicates an affinity to serum albumin and represents a method to predict a protracted pharmacokinetic profile of the test substance in animal models.

Cell Culture and Preparation

The cells used in this assay (clone FCW467-12A/KZ10-1) were BHK cells with BHKTS13 as a parent cell line. The cells were derived from a clone (FCW467-12A) that expresses the human GLP-1 receptor and were established by further transfection with CRE luciferase to obtain the current clone.

The cells were cultured at 5% $CO_2$ in cell culture medium. They were aliquoted and stored in liquid nitrogen. Before each assay an aliquot was taken up and washed twice in PBS before being suspended at the desired concentration in the assay specific buffer. For 96-well plates the suspension was made to give a final concentration of $5 \times 10^3$ cells/well.

Materials

The following chemicals were used in the assay: Pluronic F-68 (10%) (Gibco 2404), human serum albumin (HSA) (Sigma A9511), ovalbumin (Sigma A5503), DMEM w/o phenol red (Gibco 11880-028), 1 M Hepes (Gibco 15630), Glutamax 100× (Gibco 35050), and steadylite plus (PerkinElmer 6016757).

Buffers

Cell culture medium consisted of 10% FBS (Fetal Bovine Serum), 1 mg/ml G418, 240 nM MTX (methotrexate) and 1% pen/strep (penicillin/streptomycin). Assay medium consisted of DMEM w/o phenol red, 10 mM Hepes and 1× Glutamax. The 1% assay buffer consisted of 2% ovalbumin, 0.2% Pluronic F-68 and 2% HSA in assay medium. The 0% assay buffer consisted of 2% ovalbumin and 0.2% Pluronic F-68 in assay medium.

Procedure
1) Cell stocks were thawed in a 37° C. water bath.
2) Cells were washed three times in PBS.
3) The cells were counted and adjusted to $5 \times 10^3$ cells/50 µl ($1 \times 10^5$ cells/ml) in assay medium. A 50 µl aliquot of cells was transferred to each well in the assay plate.
4) Stocks of the test compounds and reference compounds were diluted to a concentration of 0.2 µM in 0% assay buffer for the 0% HSA CRE luciferase assay and 1% assay buffer for the HSA CRE luciferase assay. Compounds were diluted 10-fold to give the following concentrations: $2 \times 10^{-7}$ M, $2 \times 10^{-8}$ M; $2 \times 10^{-9}$ M, $2 \times 10^{-10}$ M, $2 \times 10^{-11}$ M, $2 \times 10^{-12}$ M and $2 \times 10^{-13}$ M. For each compound a blank assay buffer control was also included.
5) A 50 µl aliquot of compound or blank was transferred in triplicate from the dilution plate to the assay plate. Compounds were tested at the following final concentrations: $1 \times 10^{-7}$ M, $1 \times 10^{-8}$ M; $1 \times 10^{-9}$ M, $1 \times 10^{-10}$ M, $1 \times 10^{-11}$ M, $1 \times 10^{-12}$ M and $1 \times 10^{-13}$ M.
6) The assay plate was incubated for 3 h in a 5% $CO_2$ incubator at 37° C.
7) The assay plate was removed from the incubator and allowed to stand at room temperature for 15 min.
8) A 100 µl aliquot of steadylite plus reagent was added to each well of the assay plate (reagent was light sensitive).
9) Each assay plate was covered with aluminum foil to protect it from light and shaken for 30 min at room temperature.

10) Each assay plate was read in a Packard TopCount NXT instrument.

Calculations and Results

The data from the TopCount instrument were transferred to GraphPad Prism software. The software averages the values for each replicate and performs a non-linear regression. $EC_{50}$ values were calculated by the software and are shown in Table 2 below (in pM).

TABLE 2

| | In vitro potency (CRE luciferase) | | |
|---|---|---|---|
| Compound of Example no. | $EC_{50}$/pM (0% HSA) | $EC_{50}$/pM (1% HSA) | $EC_{50}$/pM (ratio 1% HSA/0% HSA) |
| 1 | 6.4 | 236 | 37 |
| 2 | 10 | 827 | 82 |
| 3 | 146 | 158 | 1.1 |
| 4 | 34 | 320 | 9.4 |
| 5 | 52 | 165 | 3.2 |
| 6 | 17 | 102 | 6.0 |
| 7 | 36 | 68 | 1.9 |
| 8 | 25 | 78 | 3.2 |
| 9 | 5.7 | 136 | 24 |
| 10 | 8.7 | 251 | 29 |
| 11 | 4.3 | 47 | 11 |
| 12 | 5.4 | 99 | 18 |
| 13 | 30 | 367 | 12 |
| 14 | 13 | 1263 | 108 |
| 15 | 7.0 | 683 | 96 |
| 16 | 16 | 56 | 3.5 |
| 17 | 16 | 379 | 24 |
| 18 | 8.7 | 296 | 34 |

All derivatives had a good in vitro potency corresponding to an $EC_{50}$ at 0% HSA of below 200 pM.

For comparison, compound no. 13 in Table 1 of Journal of Medicinal Chemistry (2000), vol. 43, no. 9, p. 1664-669 (GLP-1(7-37) acylated at $K^{26,34}$ with bis-C12-diacid) had an in vitro potency corresponding to an $EC_{50}$ at 0% HSA of 440 pM, an $EC_{50}$ at 1% HSA of 3317 pM, and a ratio (1% HSA/0% HSA) of 7.5.

Example 22: GLP-1 Receptor Binding

The purpose of this experiment is to investigate the binding to the GLP-1 receptor of the GLP-1 derivatives, and how the binding is potentially influenced by the presence of albumin. This is done in an in vitro experiment as described below.

The binding affinity of the GLP-1 derivatives of Examples 1-18 to the human GLP-1 receptor was measured by way of their ability to displace of $^{125}$I-GLP-1 from the receptor. In order to test the binding of the derivatives to albumin, the assay was performed with a low concentration of albumin (approximately 0.001%—corresponding to the residual amount thereof in the tracer), as well as with a high concentration of albumin (2.0% added). A shift in the binding affinity, $IC_{50}$, is an indication that the peptide in question binds to albumin, and thereby a prediction of a potential protracted pharmacokinetic profile of the peptide in question in animal models.

Conditions

Species (in vitro): Hamster
Biological End Point: Receptor Binding
Assay Method: SPA
Receptor: GLP-1 receptor
Cell Line: BHK tk-ts13

Cell Culture and Membrane Purification

A stable transfected cell line and a high expressing clone were selected for screening. The cells were grown at 5% $CO_2$ in DMEM, 10% FCS, 1% Pen/Strep (Penicillin/Streptomycin) and 1.0 mg/ml of the selection marker G418.

The cells (approx. 80% confluence) were washed twice in PBS and harvested with Versene (aqueous solution of the tetrasodium salt of ethylenediaminetetraacetic acid), following which they were separated by centrifugation at 1000 rpm for 5 min. The cells/cell pellet must be kept on ice to the extent possible in the subsequent steps. The cell pellet was homogenised with Ultrathurrax for 20-30 seconds in a suitable amount of Buffer 1 (depending on the amount of cells, but e.g. 10 ml). The homogenate was centrifuged at 20000 rpm for 15 minutes. The pellet was resuspended (homogenised) in 10 ml Buffer 2 and re-centrifuged. This step was repeated once more. The resulting pellet was resuspended in Buffer 2, and the protein concentration was determined. The membranes were stored at minus 80° C.

Buffer 1: 20 mM Na-HEPES+10 mM EDTA, pH 7.4
Buffer 2: 20 mM Na-HEPES+0.1 mM EDTA, pH 7.4

Binding Assay:

SPA:

Test compounds, membranes, SPA-particles and $[^{125}I]$-GLP-1(7-36)$NH_2$ were diluted in assay buffer. 50 ul (micro liter) HSA ("high albumin" experiment containing 2% HSA), or buffer ("low albumin" experiment containing 0.001% HSA) was added to Optiplate, and 25 ul of test compounds were added. 5-10 ug membrane protein/sample was added (50 ul) corresponding to 0.1-0.2 mg protein/ml (to be preferably optimised for each membrane preparation). SPA-particles (Wheatgerm agglutinin SPA beads, Perkin Elmer, #RPNQ0001) were added in an amount of 0.5 mg/well (50 ul). The incubation was started with $[^{125}I]$-GLP-1]-(7-36)$NH_2$ (final concentration 0.06 nM corresponding to 49.880 DPM, 25 ul). The plates were sealed with PlateSealer and incubated for 120 minutes at 30° C. while shaking. The plates were centrifuged (1500 rpm, 10 min) and counted in Topcounter.

Assay Buffer:

50 mM HEPES
5 mM EGTA
5 mM $MgCl_2$
0.005% Tween 20
pH 7.4
HSA was SIGMA A1653

Calculations

The $IC_{50}$ value was read from the curve as the concentration which displaces 50% of $^{125}$I-GLP-1 from the receptor.

Generally, the binding to the GLP-1 receptor at low albumin concentration should be as good as possible (good potency), corresponding to a low $IC_{50}$ value.

The $IC_{50}$ value at high albumin concentration is a measure of the influence of albumin on the binding of the derivative to the GLP-1 receptor. As is known, the GLP-1 derivatives also bind to albumin. This is a generally desirable effect, which extends their lifetime in plasma. Therefore, the $IC_{50}$ value at high albumin will generally be higher than the $IC_{50}$ value at low albumin, corresponding to a reduced binding to the GLP-1 receptor, caused by albumin binding competing with the binding to the GLP-1 receptor.

Results
The following results were obtained:

TABLE 3

Receptor binding affinity

| Compound of Example no. | IC$_{50}$/nM(low HSA) | IC$_{50}$/nM (high HSA) |
|---|---|---|
| 1 | 0.52 | 21 |
| 2 | 0.73 | 448 |
| 3 | 0.82 | 218 |
| 4 | 0.93 | 264 |
| 5 | 2.35 | 244 |
| 6 | 1.02 | 163 |
| 7 | 1.37 | 89 |
| 8 | 2.08 | 295 |
| 9 | 0.84 | ≥1000 |
| 10 | 1.36 | ≥1000 |
| 11 | 0.49 | 68 |
| 12 | 0.26 | 150 |
| 13 | 1.63 | 958 |
| 14 | 2.01 | 618 |
| 15 | 1.13 | 329 |
| 16 | 0.63 | 53 |
| 17 | 11.1 | ≥1000 |
| 18 | 0.04 | 35 |

All derivatives had an IC$_{50}$ (low albumin) below 12.0 nM. As regards IC$_{50}$ (high albumin), all but three derivatives had an IC$_{50}$ (high albumin) below 1000 nM.

For comparison, compound no. 13 in Table 1 of Journal of Medicinal Chemistry (2000), vol. 43, no. 9, p. 1664-669 (GLP-1(7-37) acylated at K$^{26,34}$ with bis-C12-diacid) had an IC$_{50}$ (low albumin) of 17.7 nM, and an IC$_{50}$ (high albumin) of 908 nM.

Example 23: Pharmacokinetic (PK) Study in Minipig

The purpose of this study is to determine the protraction in vivo of the GLP-1 derivatives after i.v. administration to minipigs, i.e. the prolongation of their time of action. This is done in a pharmacokinetic (PK) study, where the terminal half-life of the derivative in question is determined. By terminal half-life is generally meant the period of time it takes to halve a certain plasma concentration, measured after the initial distribution phase.

The derivatives of Examples 3 and 6 were subjected to PK study A (see below), whereas the derivatives of Examples 2 and 13 were subjected to PK study B (see below).

Study A: Male Göttingen minipigs were obtained from Ellegaard Göttingen Minipigs (Dalmose, Denmark) approximately 7-14 months of age and weighing from approximately 16-35 kg were used in the studies. The minipigs were housed individually and fed restrictedly once or twice daily with SDS minipig diet (Special Diets Services, Essex, UK). After at least 2 weeks of acclimatisation two permanent central venous catheters were implanted in vena cava caudalis or cranialis in each animal. The animals were allowed 1 week recovery after the surgery, and were then used for repeated pharmacokinetic studies with a suitable wash-out period between successive GLP-1 derivative dosings.

The animals were fasted for approximately 18 h before dosing and from 0 to 4 h after dosing, but had ad libitum access to water during the whole period.

The GLP-1 derivatives were dissolved in 50 mM sodium phosphate, 145 mM sodium chloride, 0.05% tween 80, pH 7.4 to a concentration of usually from 20-60 nmol/ml. Intravenous injections (the volume corresponding to usually 1-2 nmol/kg, for example 0.033 ml/kg) of the compounds were given through one catheter, and blood was sampled at predefined time points for up till 13 days post dosing (preferably through the other catheter). Blood samples (for example 0.8 ml) were collected in EDTA buffer (8 mM) and then centrifuged at 4° C. and 1942 G for 10 minutes.

Study B: Male Göttingen minipigs were obtained from Ellegaard Göttingen Minipigs (Dalmose, Denmark) approximately 5 months of age and weighing from approximately 9 kg were used in the studies. The minipigs were housed in pens with straw as bedding, six together in each pen and fed restrictedly once or twice daily with Altromin 9023 minipig diet (Chr. Petersen NS, DK-4100 Ringsted). The pigs were used for repeated pharmacokinetic studies with a suitable wash-out period between successive GLP-1 derivative dosings. An acclimatisation period of 1 week was allowed during which time the minipigs was trained to be fixated on the backs for blood sampling and in slings for i.v. dosing. All handling, dosing and blood sampling of the animals will be performed by trained and skilled staff.

The animals were fasted for approximately 18 h before dosing and from 0 to 4 h after dosing, but had ad libitum access to water during the whole period.

The GLP-1 derivatives were dissolved in 50 mM sodium phosphate, 145 mM sodium chloride, 0.05% tween 80, pH 7.4 to a concentration of usually from 20-60 nmol/ml. Intravenous injections (the volume corresponding to usually 2 nmol/kg, for example 0.1 ml/kg) of the compounds were given as intravenous injections via a Venflon inserted in an ear vein, while they are placed unanaesthetised in a sling. The dose volume was 0.1 ml/kg, and blood was sampled at predefined time points for up till 17 days post dosing (samples was taken with syringe from a jugular vein). Blood samples (for example 0.8 ml) were collected in EDTA buffer (8 mM) and then centrifuged at 4° C. and 2000 G for 10 minutes.

Sampling and analysis (study A and B): Plasma was pippetted into Micronic tubes on dry ice, and kept at −20° C. until analyzed for plasma concentration of the respective GLP-1 compound using ELISA or a similar antibody based assay or LC-MS. Individual plasma concentration-time profiles were analyzed by a non-compartmental model in Phoenix WinNonLin ver. 6.2. (Pharsight Inc., Mountain View, Calif., USA), and the resulting terminal half-lives (harmonic mean) determined.

Results

The compounds of Examples 2, 3, 6, and 13 were tested, and the results are shown in Table 4, below.

TABLE 4

Half-life in minipigs

| Compound of Example no. | Minipig iv PK, T½ (hours) |
|---|---|
| 2 | 68 |
| 3 | 66 |
| 6 | 93 |
| 13 | 79 |

All compounds tested had a very fine half-life well above 50 hours.

For comparison, compound no. 13 in Table 1 of Journal of Medicinal Chemistry (2000), vol. 43, no. 9, p. 1664-669 (GLP-1(7-37) acylated at K$^{26,34}$ with bis-C12-diacid) had a half-life of 5 hours.

Example 24: Pharmacokinetic (PK) Study in Rat

The purpose of this Example is to investigate half-life in vivo in rat.

In vivo pharmacokinetic studies in rats were performed with the GLP-1 derivatives of a number of the Example compounds, as described in the following. Semaglutide was included for comparison.

Male Sprague Dawley rats of same age with a body weight of approximately 400 g were obtained from Taconic (Denmark) and assigned to the treatments by simple randomisation on body weight, approximately 4 rats per group.

The GLP-1 derivatives (approximately 6 nmol/ml) were dissolved in 50 mM sodium phosphate, 145 mM sodium chloride, 0.05% tween 80, pH 7.4. Intravenous injections (1.0 ml/kg) of the compounds were given with a syringe in the tail vein of conscious rats. Blood was sampled from vena sublingualis for 5 days post dosing. Blood samples (200 μl) were collected in EDTA buffer (8 mM) and then centrifuged at 4° C. and 10000 G for 5 minutes. Plasma samples were kept at −20° C. until analyzed for plasma concentration of the respective GLP-1 compound.

The plasma concentrations of the GLP-1 compounds were determined using a Luminescence Oxygen Channeling Immunoassay (LOCI), generally as described for the determination of insulin by Poulsen and Jensen in Journal of Biomolecular Screening 2007, vol. 12, p. 240-247. The donor beads were coated with streptavidin, while acceptor beads were conjugated with a monoclonal antibody recognising a mid-/C-terminal epitope of the peptide. Another monoclonal antibody, specific for the N-terminus, was biotinylated. The three reactants were combined with the analyte and formed a two-sited immuno-complex. Illumination of the complex released singlet oxygen atoms from the donor beads, which were channeled into the acceptor beads and triggered chemiluminescence which was measured in an Envision plate reader. The amount of light was proportional to the concentration of the compound.

Plasma concentration-time profiles were analyzed using Phoenix WinNonLin ver. 6.2, Pharsight Inc., Mountain View, Calif., USA), and the half-life ($T_{1/2}$) calculated using individual plasma concentration-time profiles from each animal.

Results

The results are shown in Table 5, below.

TABLE 5

| Half-life in rat | |
| --- | --- |
| Compound of Example no. | PK in ratT½ (hours) |
| 1 | 13 |
| 2 | 17 |
| 8 | 14 |
| 11 | 10 |

All tested compounds had a half-life of 10 hours or above. The half-life of semaglutide tested in the same set-up but with n=8 was 11 hours.

Example 25: Pharmacodynamic (PD) Study in Pigs

The purpose of this experiment was to investigate the effect of a couple of Example compounds on food intake in pigs. This was done in a pharmacodynamic (PD) study as described below, in which food intake was measured from 1 to 4 days after administration of a single dose of the GLP-1 derivative, as compared to a vehicle-treated control group.

Female Landrace Yorkshire Duroc (LYD) pigs, approximately 3 months of age, weighing approximately 30-35 kg were used (n=3-4 per group). The animals were housed in a group for approximately 1 week during acclimatisation to the animal facilities. During the experimental period the animals were placed in individual pens at least 2 days before dosing and during the entire experiment for measurement of individual food intake. The animals were fed ad libitum with pig fodder (Svinefoder Danish Top) at all times both during the acclimatisation and the experimental period. Food intake was monitored on line by logging the weight of fodder every 15 minutes. The system used was Mpigwin (Ellegaard Systems, Faaborg, Denmark).

The GLP-1 derivatives were dissolved in a phosphate buffer (50 mM sodium phosphate, 145 mM sodium chloride, 0.05% tween 80, pH 7.4) at concentrations of 12, 40, 120, 400 or 1200 nmol/ml corresponding to doses of 0.3, 1, 3, 10 or 30 nmol/kg. The phosphate buffer serves as vehicle. Animals are dosed with a single subcutaneous dose of the GLP-1 derivative or vehicle (dose volume 0.025 ml/kg) on the morning of day 1, and food intake is measured for 1 day after dosing. On the last day of each study, 1-4 days after dosing, a blood sample for measurement of plasma exposure of the GLP-1 derivative is taken from the heart in anaesthetised animals. The animals are thereafter euthanised with an intra-cardial overdose of pentobarbitone. Plasma content of the GLP-1 derivatives is analysed using ELISA or a similar antibody based assay or LC-MS.

Food intake is calculated as mean±SEM food intake in 24 h intervals (0-24 h, 24-48 h, and 48-72 h). In Table 6 below the food intake is indicated as percentage of the food intake of the vehicle group in the same time interval (dosage 3.0 nmol/kg).

Statistical comparisons of the food intake in the 24 hour intervals in the vehicle vs. GLP-1 derivative group are done using two-way-ANOVA repeated measures, followed by Bonferroni post-test.

Results

The results are shown in Table 6, below.

TABLE 6

| Effect on food intake in pigs | | | |
| --- | --- | --- | --- |
| Compound of | PD in pig, food intake (% of vehicle) for hours (x-y) Time interval (h) | | |
| Example no. | 0-24 | 24-48 | 48-72 |
| 2 | 58 | 73 | — |
| 8 | 50 | 94 | — |

The tested compounds showed a very nice reduction in food intake.

For comparison, compound no. 13 in Table 1 of Journal of Medicinal Chemistry (2000), vol. 43, no. 9, p. 1664-669 (GLP-1(7-37) acylated at $K^{26,34}$ with bis-C12-diacid) when tested in the same way had a food intake (% of vehicle) for hours 0-24, 24-48, and 48-72, of 95%, 96%, and 103%, respectively.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

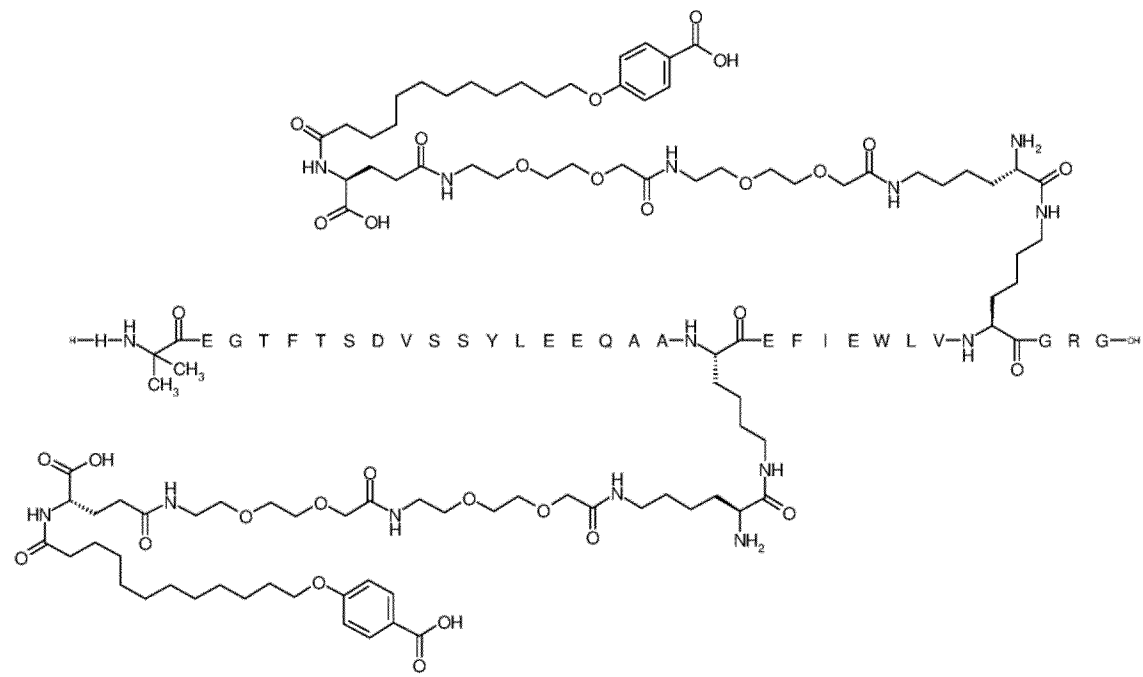

The invention claimed is:
1. A compound selected from the following:
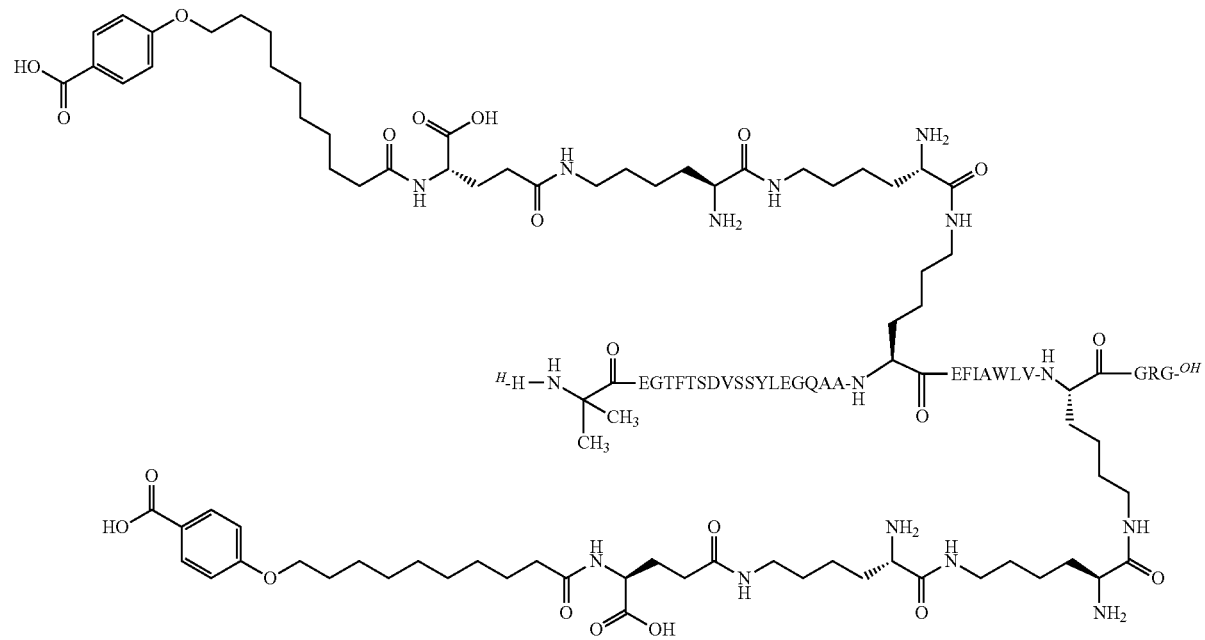
Chem.21
where the amino acid sequence is that of SEQ ID NO: 4,
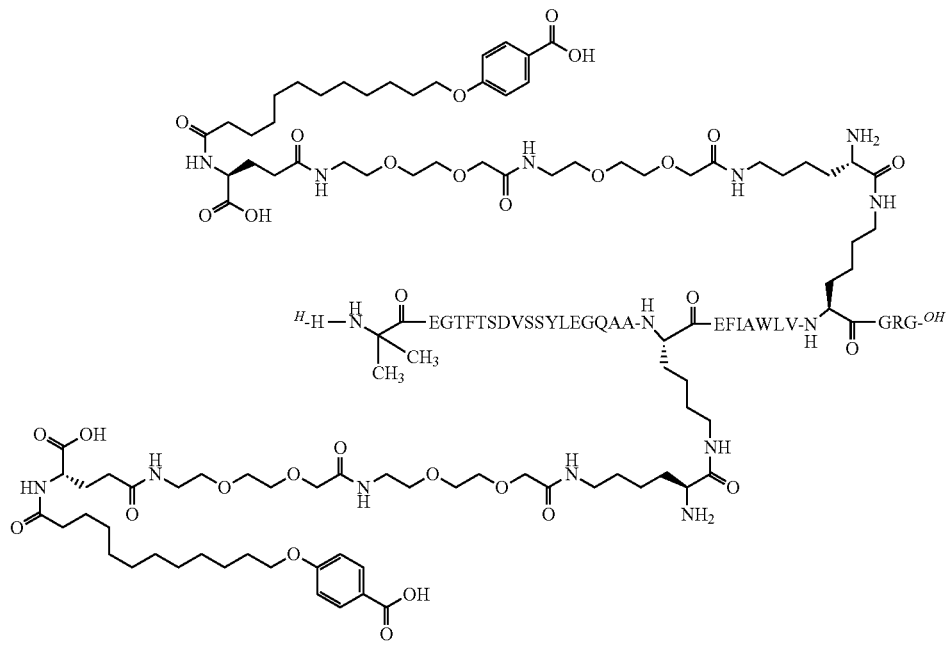
Chem. 22
where the amino acid sequence is that of SEQ ID NO: 4,

Chem. 23
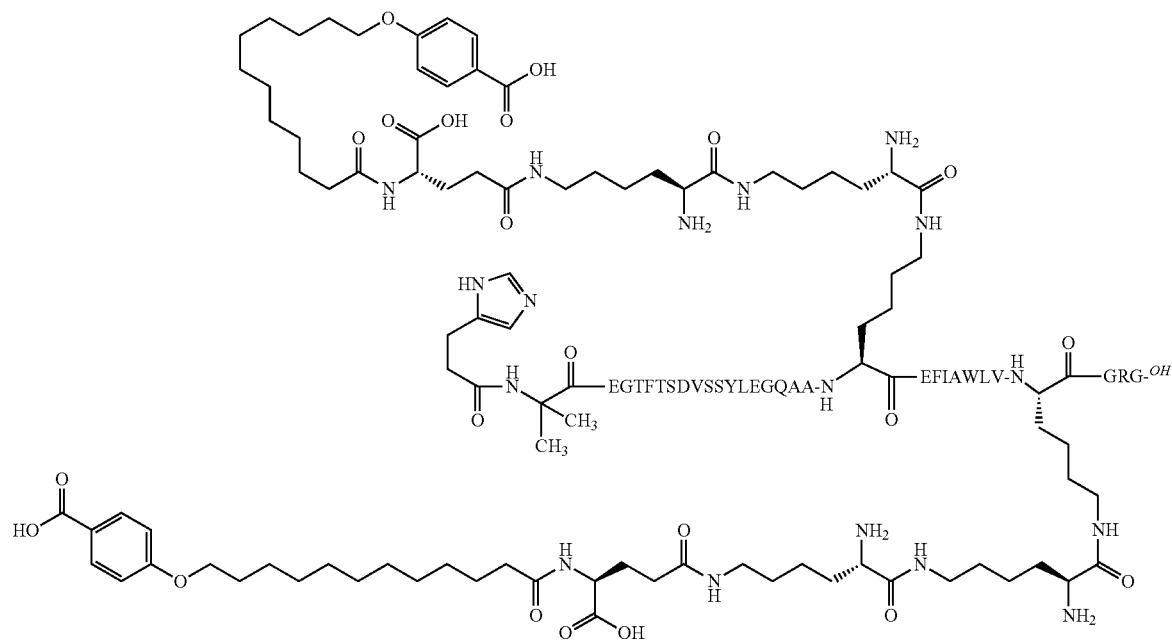
where the amino acid sequence is that of SEQ ID NO: 5,
Chem. 24
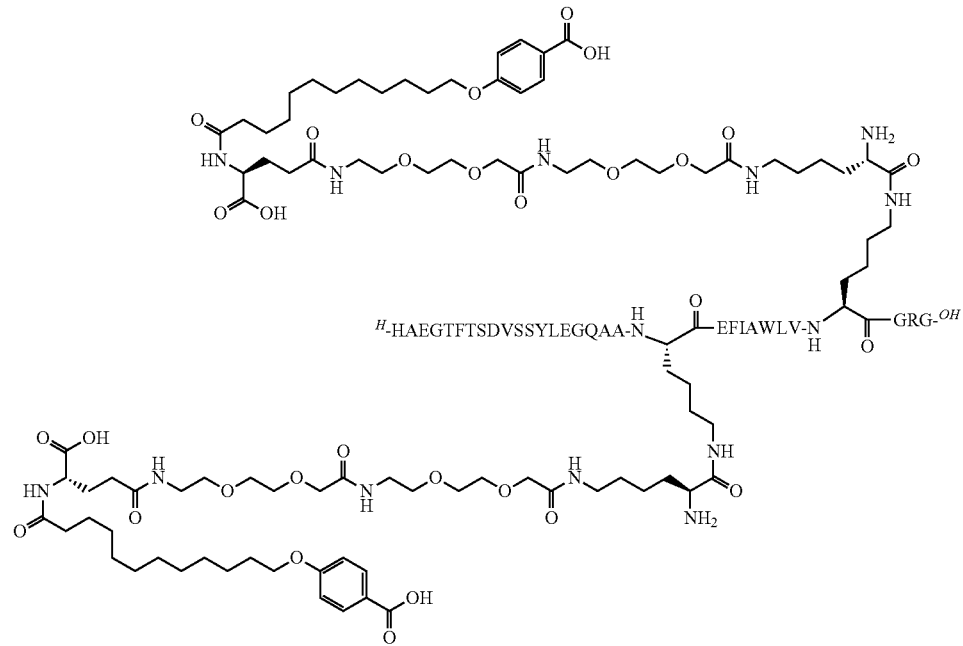
where the amino acid sequence is that of SEQ ID NO: 1, Chem. 25
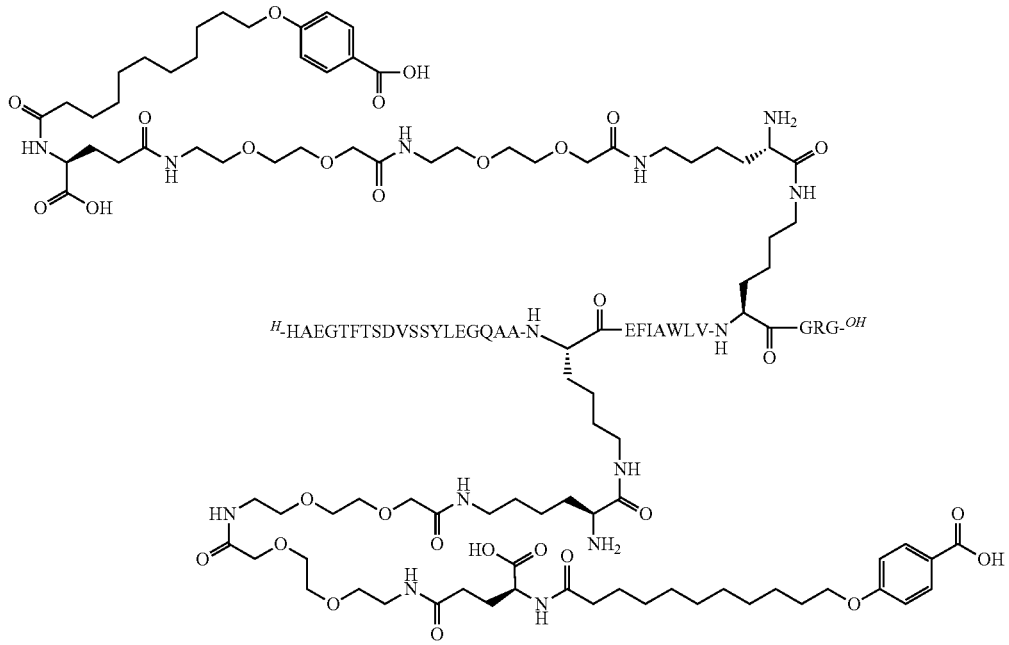
where the amino acid sequence is that of SEQ ID NO: 1,
Chem. 26
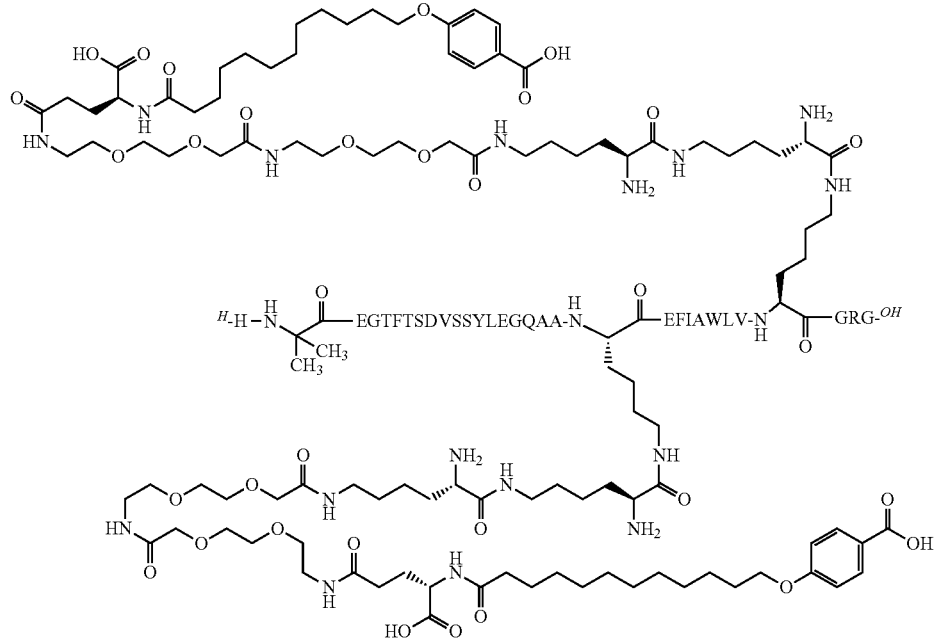
where the amino acid sequence is that of SEQ ID NO: 4, Chem. 27
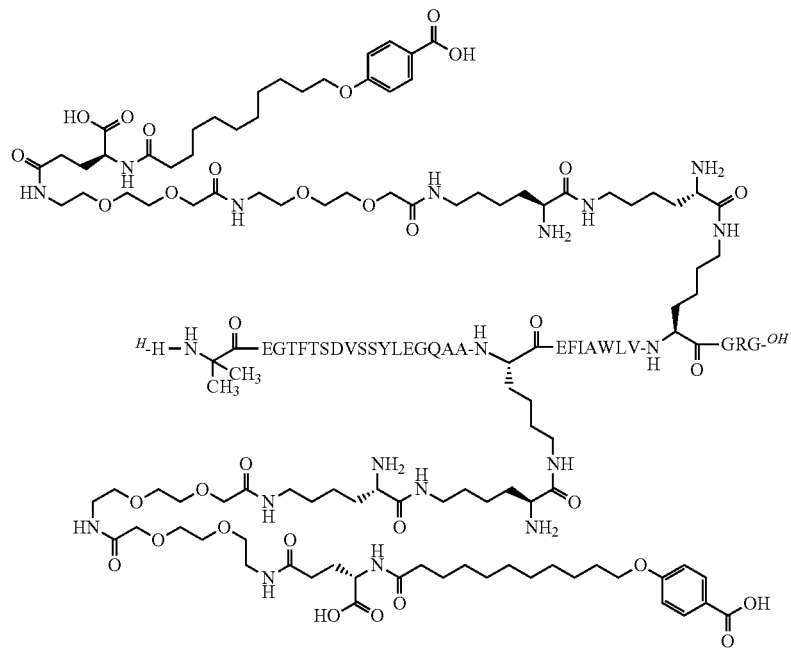
where the amino acid sequence is that of SEQ ID NO: 4,
Chem. 28
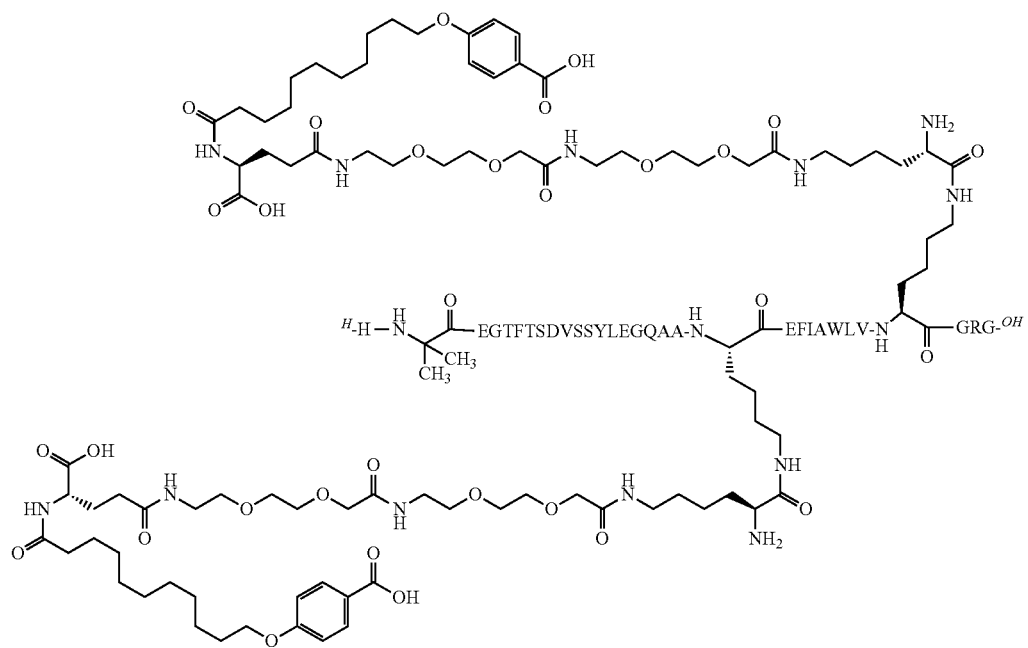
where the amino acid sequence is that of SEQ ID NO: 4, Chem. 29
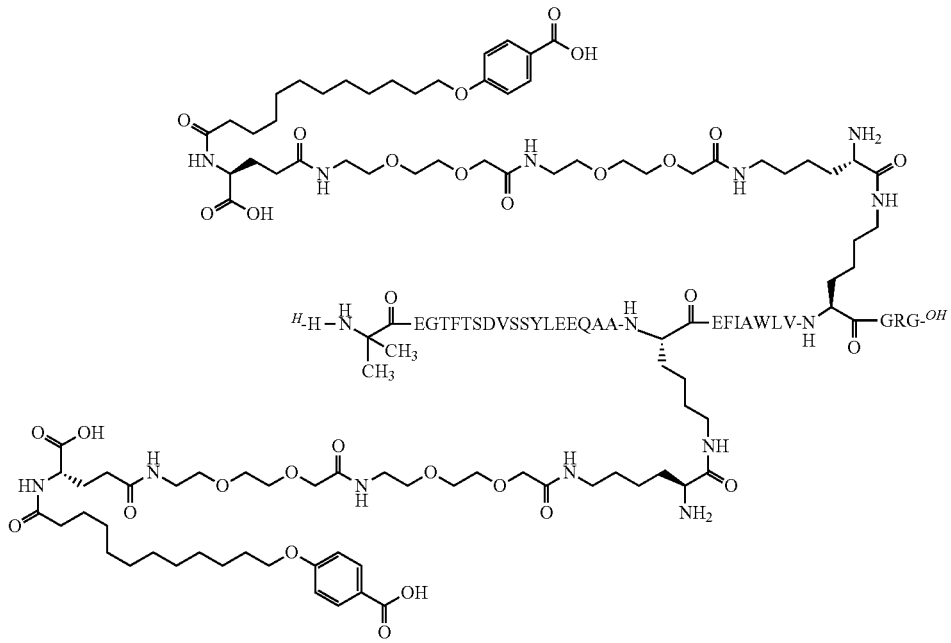
where the amino acid sequence is that of SEQ ID NO: 6,
Chem. 30
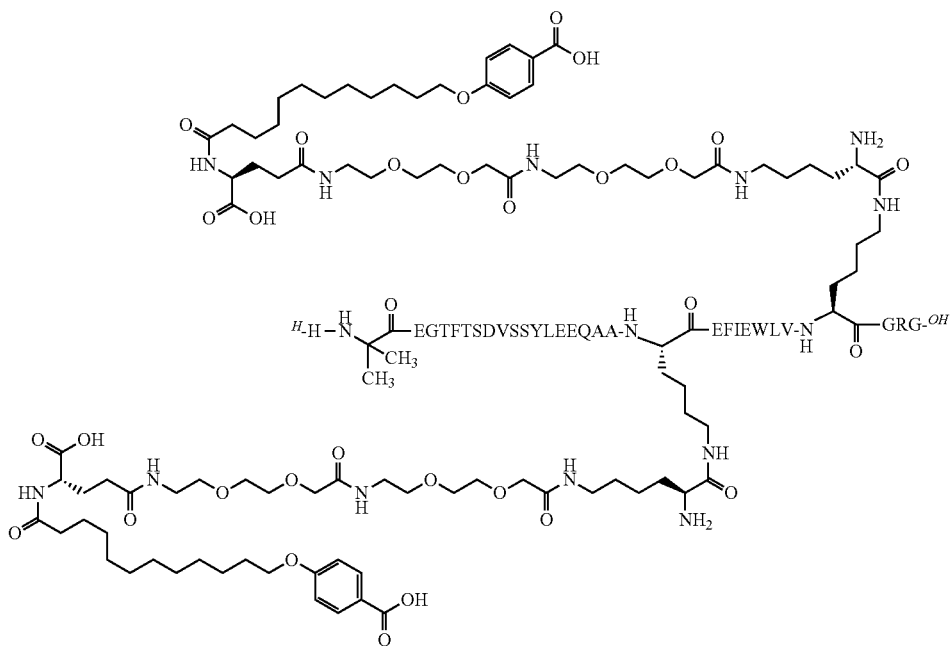
where the amino acid sequence is that of SEQ ID NO: 7, Chem 31
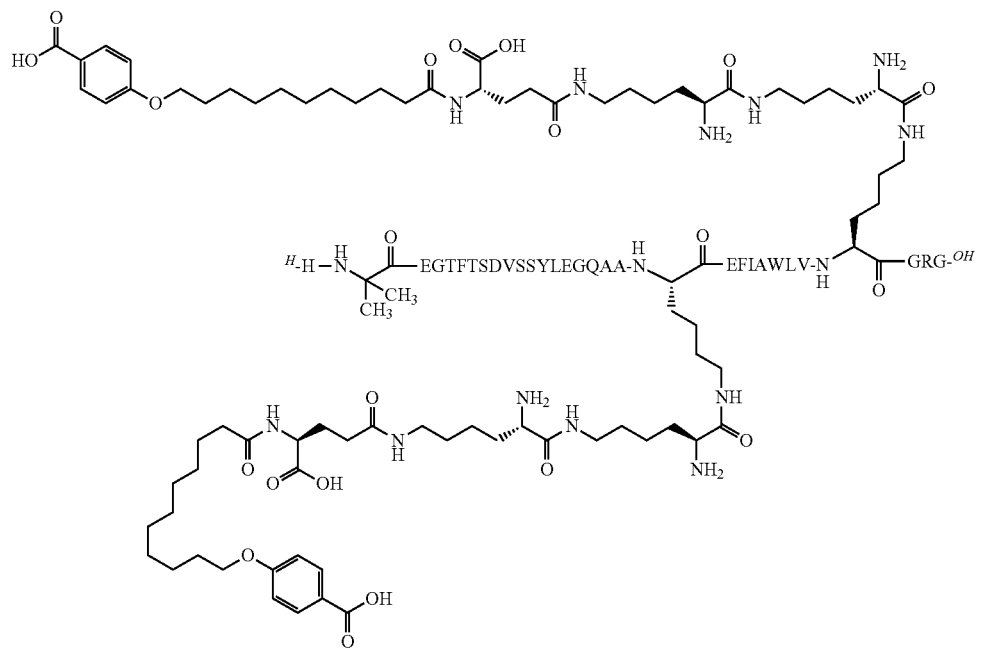
where the amino acid sequence is that of SEQ ID NO: 4, and
Chem. 32
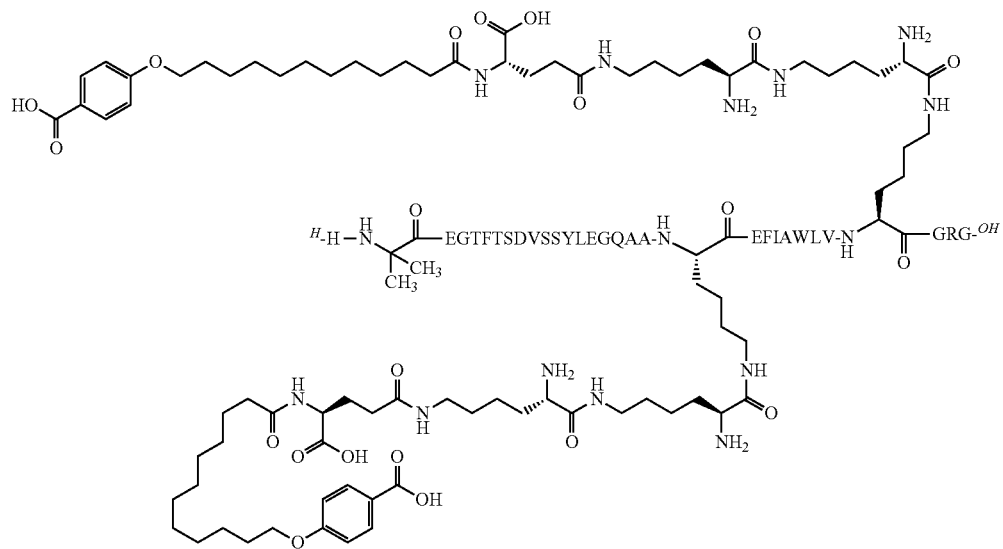
where the amino acid sequence is that of SEQ ID NO: 4,
or a pharmaceutically acceptable salt, amide, or ester of any of the preceding compounds.

2. The compound of claim 1, wherein the compound is
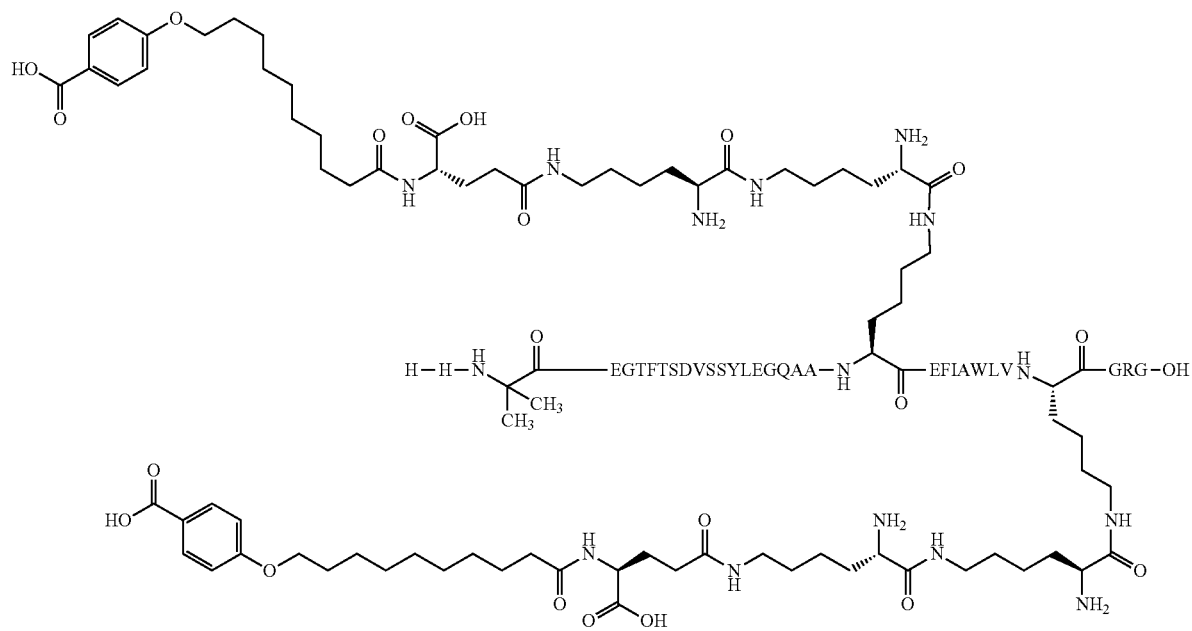
Chem. 21
where the amino acid sequence is that of SEQ ID NO: 4, or a pharmaceutically acceptable salt, amide, or ester thereof.
3. The compound of claim 1, wherein the compound is
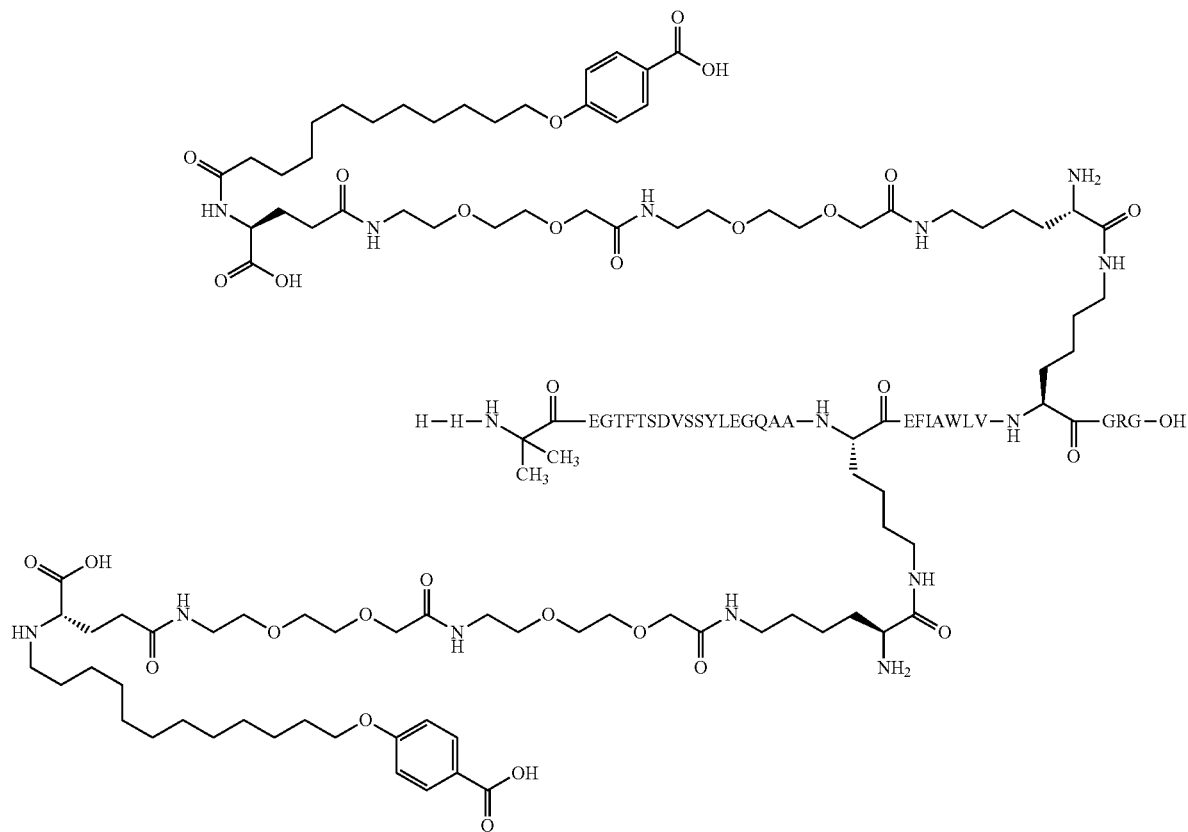
Chem. 22 where the amino acid sequence is that of SEQ ID NO: 4, or a pharmaceutically acceptable salt, amide, or ester thereof.
4. The compound of claim 1, wherein the compound is
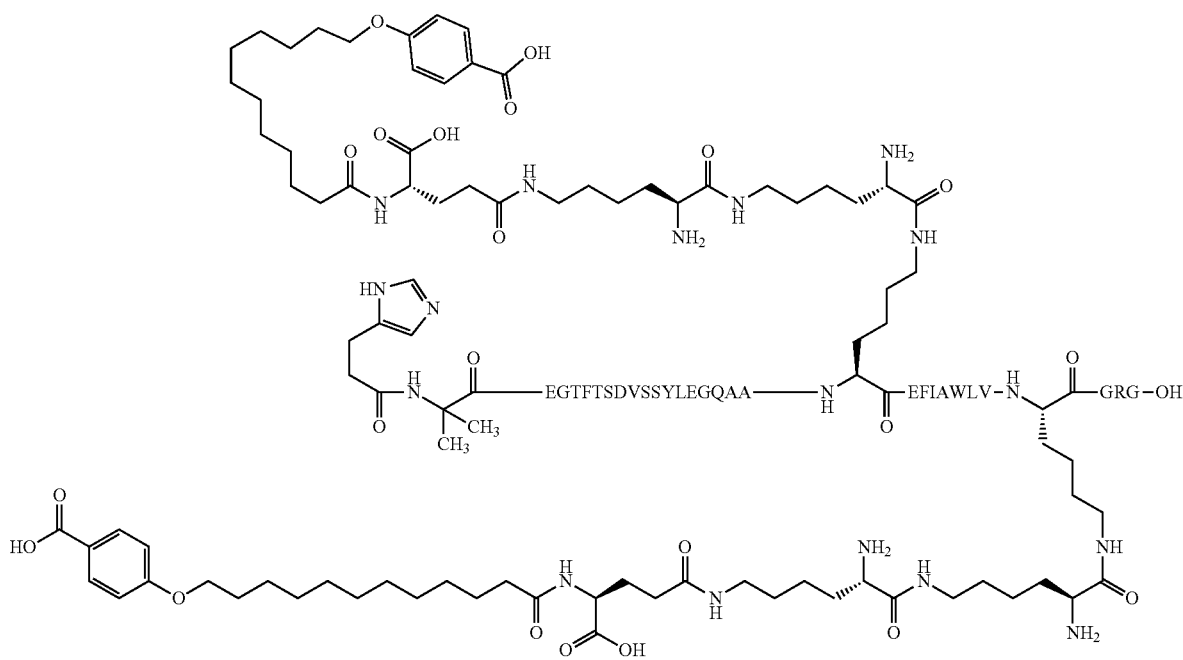
where the amino acid sequence is that of SEQ ID NO: 5, or a pharmaceutically acceptable salt, amide, or ester thereof.

5. The compound of claim 1, wherein the compound is
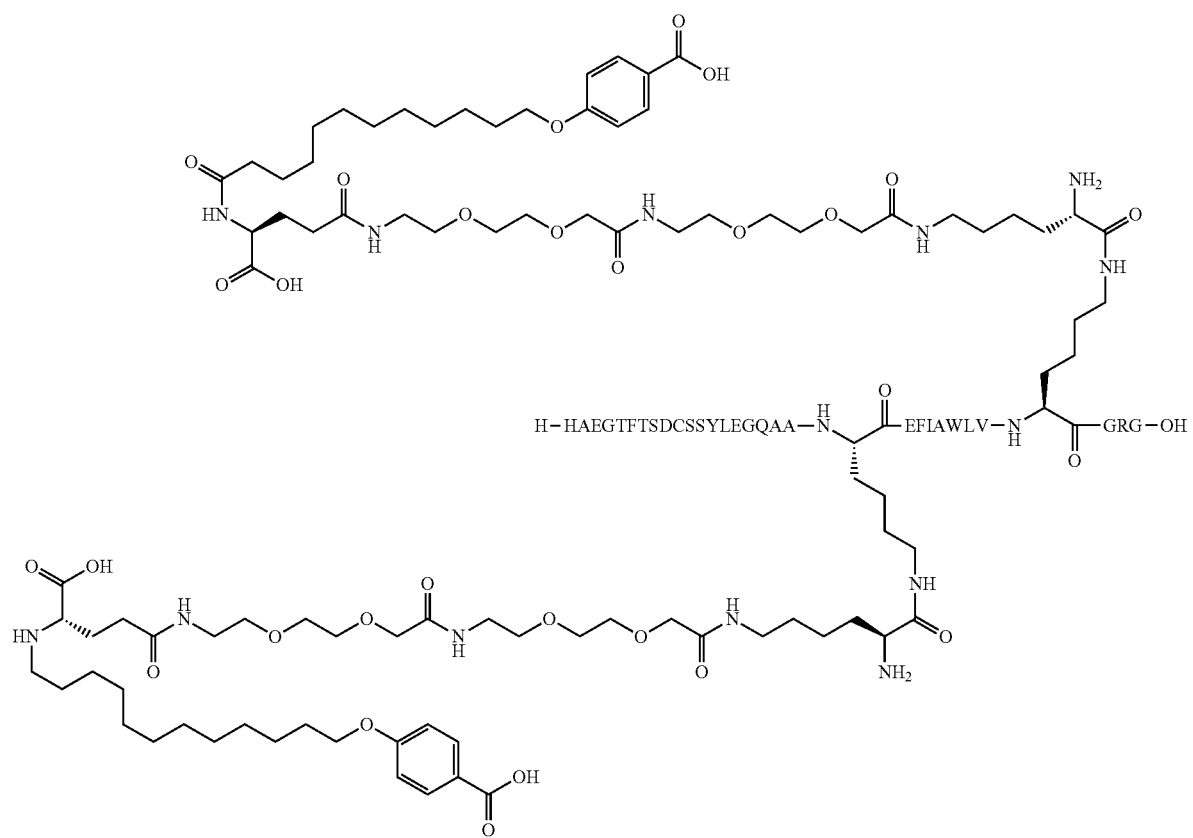
Chem. 24
where the amino acid sequence is that of SEQ ID NO: 1, or a pharmaceutically acceptable salt, amide, or ester thereof.

6. The compound of claim 1, wherein the compound is
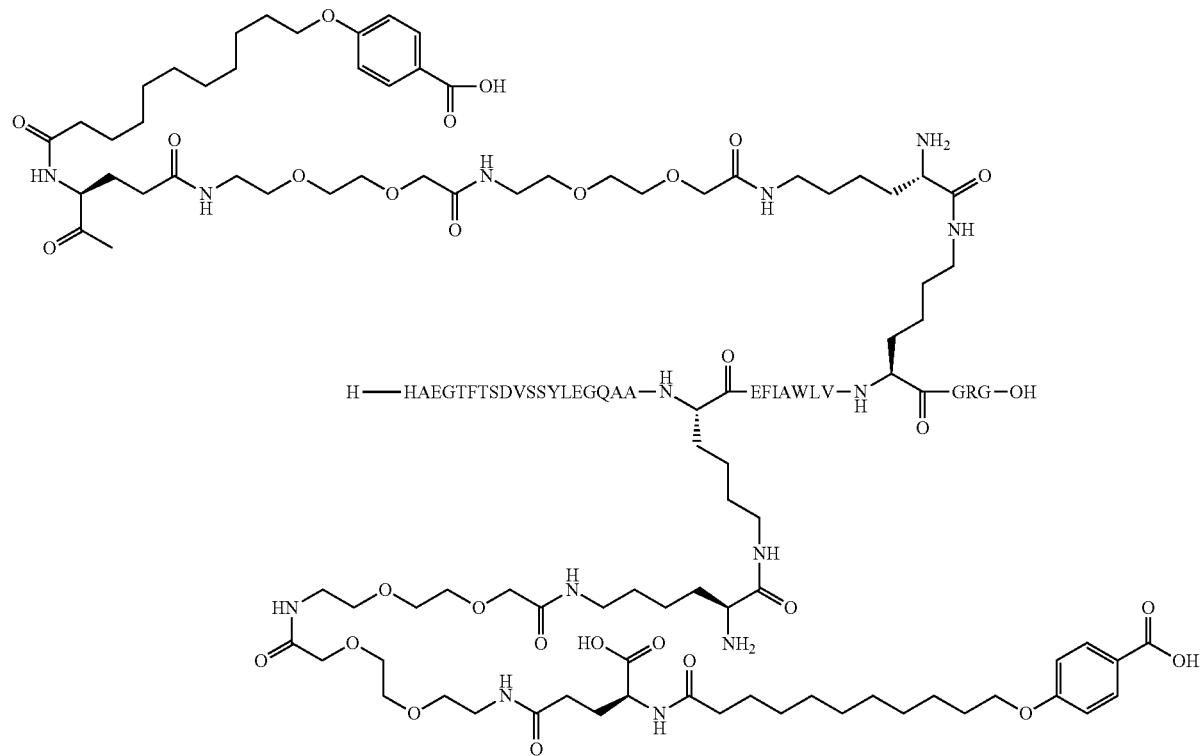
Chem. 25
where the amino acid sequence is that of SEQ ID NO: 1, or a pharmaceutically acceptable salt, amide, or ester thereof.

7. The compound of claim 1, wherein the compound is
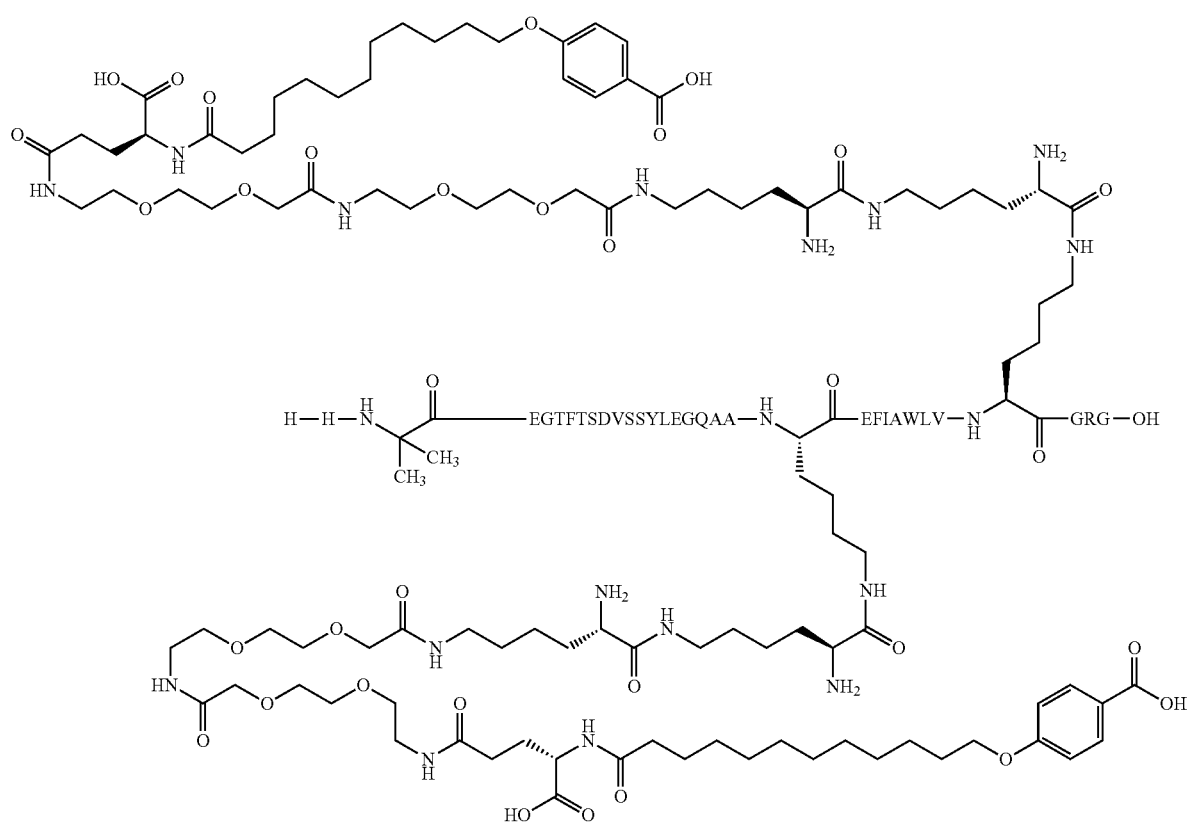
Chem. 26
where the amino acid sequence is that of SEQ ID NO: 4, or a pharmaceutically acceptable salt, amide, or ester thereof.

8. The compound of claim 1, wherein the compound is
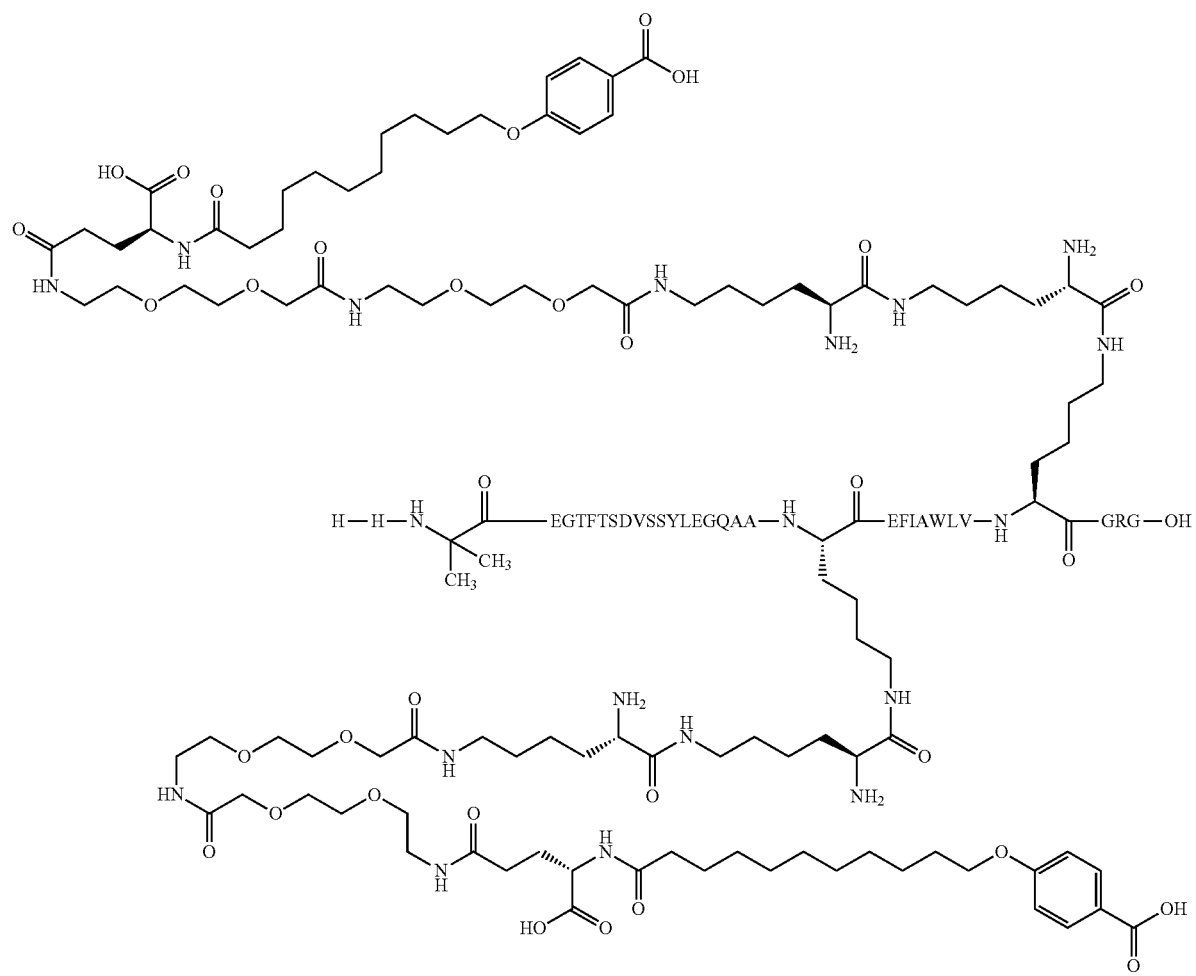
Chem. 27
where the amino acid sequence is that of SEQ ID NO: 4, or a pharmaceutically acceptable salt, amide, or ester thereof.

9. The compound of claim 1, wherein the compound is
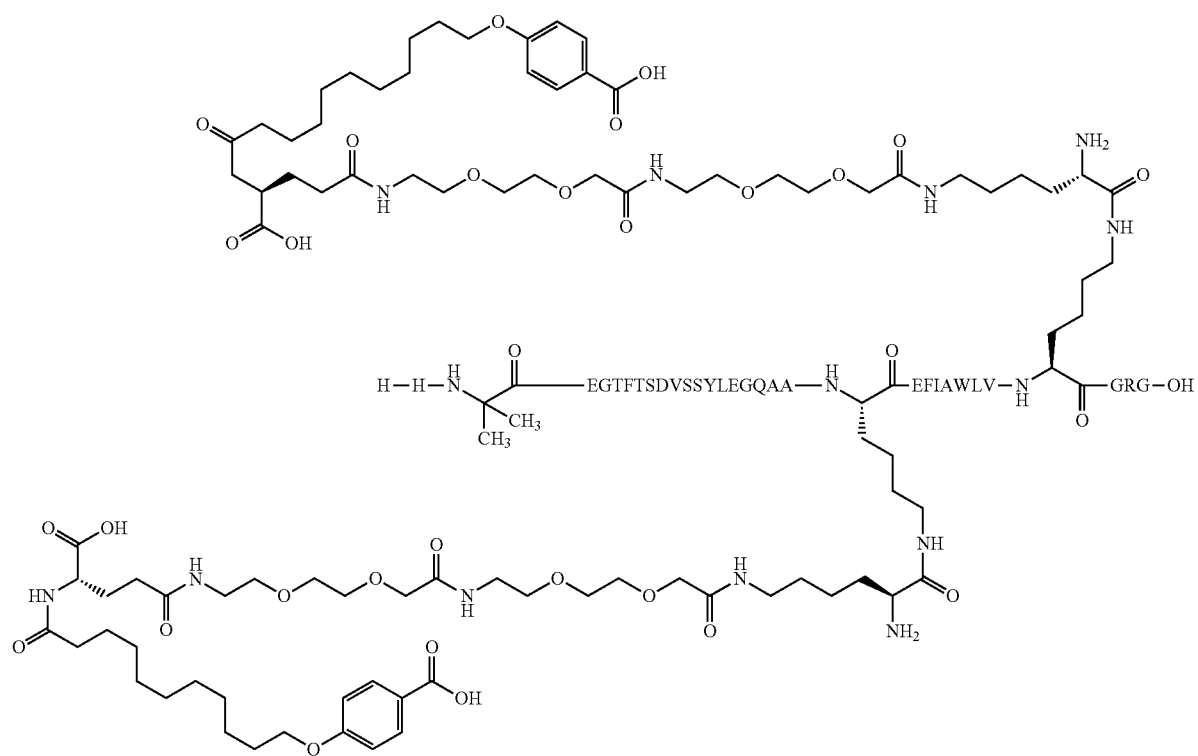
Chem. 28
where the amino acid sequence is that of SEQ ID NO: 4, or a pharmaceutically acceptable salt, amide, or ester thereof.

10. The compound of claim 1, wherein the compound is
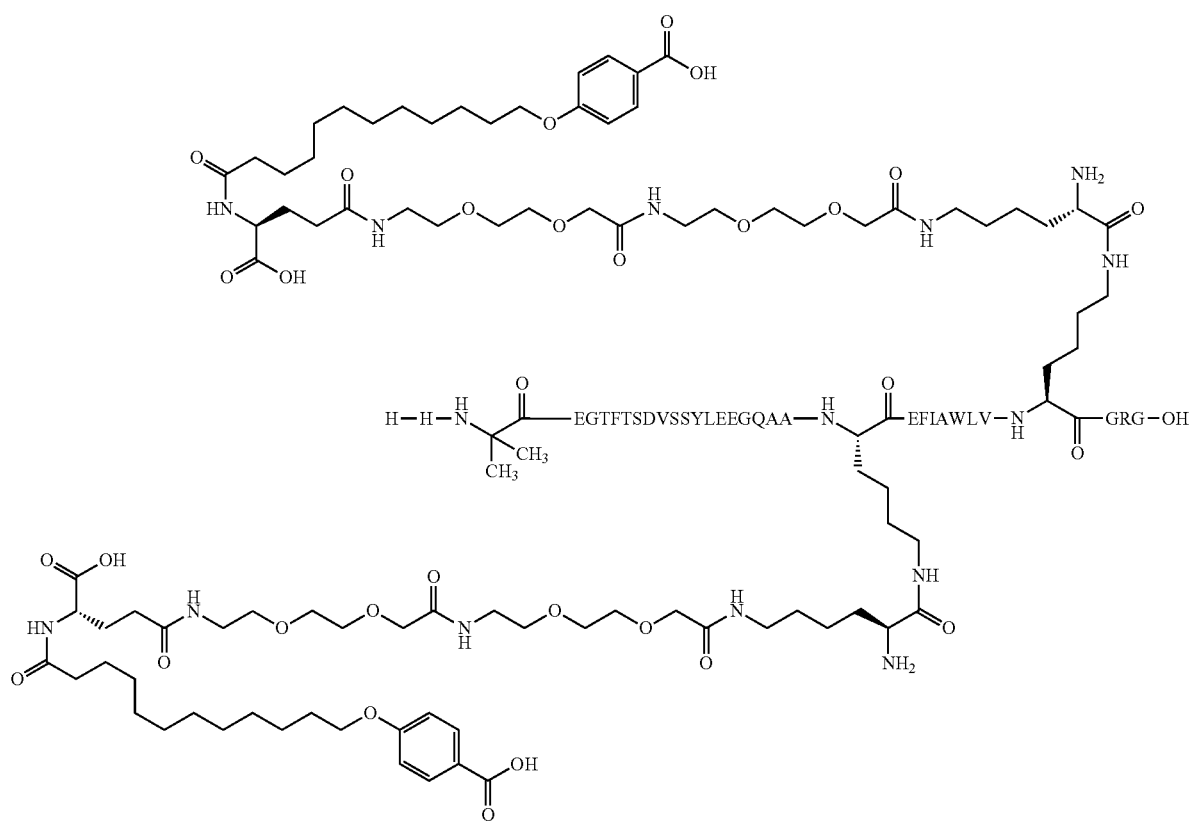
Chem. 29
where the amino acid sequence is that of SEQ ID NO: 6, or a pharmaceutically acceptable salt, amide, or ester thereof.

11. The compound of claim 1, wherein the compound is
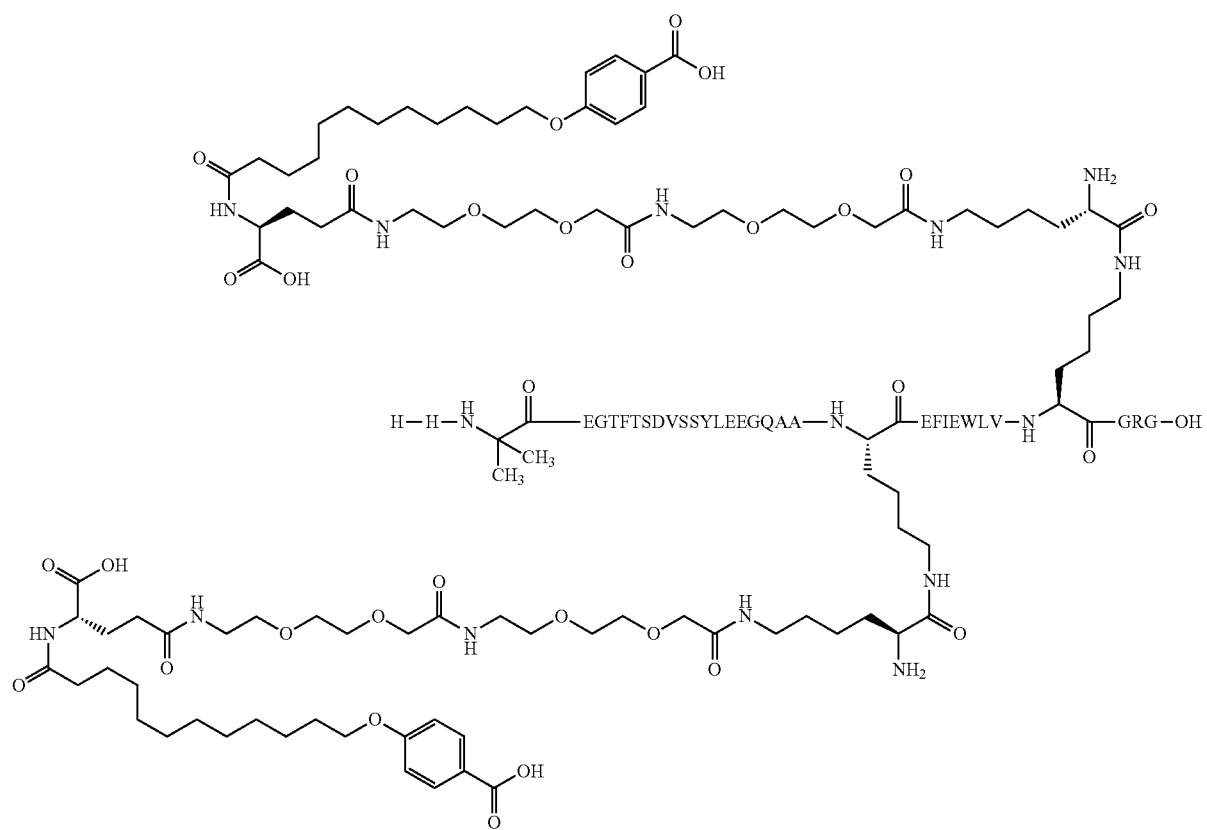
Chem. 30
where the amino acid sequence is that of SEQ ID NO: 7, or a pharmaceutically acceptable salt, amide, or ester thereof.

12. The compound of claim 1, wherein the compound is

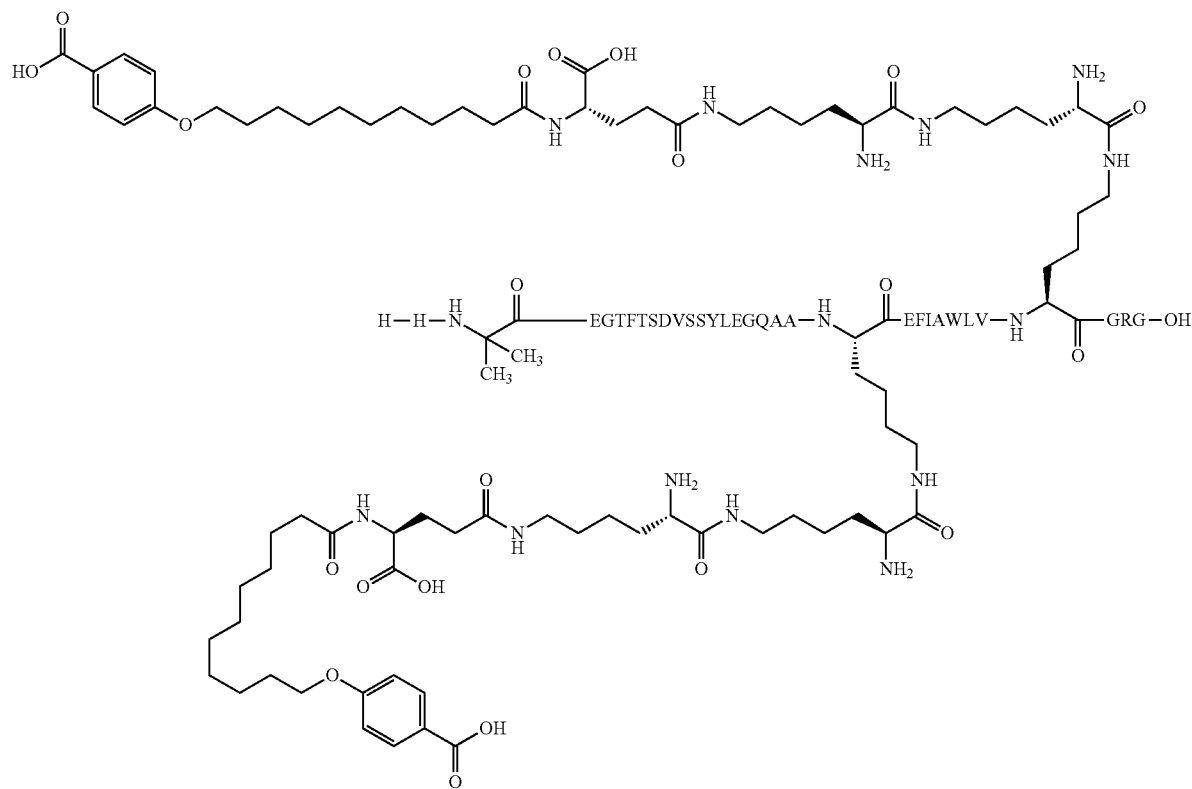

Chem. 31 where the amino acid sequence is that of SEQ ID NO: 4, or a pharmaceutically acceptable salt, amide, or ester thereof.

13. A method for treating diabetes in a subject in need of such treatment, said method comprising administering to a subject a pharmaceutically active amount of the compound of claim 1.

14. A composition comprising the compound of claim 1 and an antidiabetic agent.

15. The composition of claim 14, wherein the antidiabetic agent is insulin.

* * * * *

UNITED STATES PATENT AND TRADEMARK OFFICE
CERTIFICATE OF CORRECTION

PATENT NO. : 11,274,135 B2
APPLICATION NO. : 14/399086
DATED : March 15, 2022
INVENTOR(S) : Jacob Kofoed et al.

Page 1 of 2

It is certified that error appears in the above-identified patent and that said Letters Patent is hereby corrected as shown below:

In the Claims

At Column 123-124, Claim number 5, please replace with the following formula:

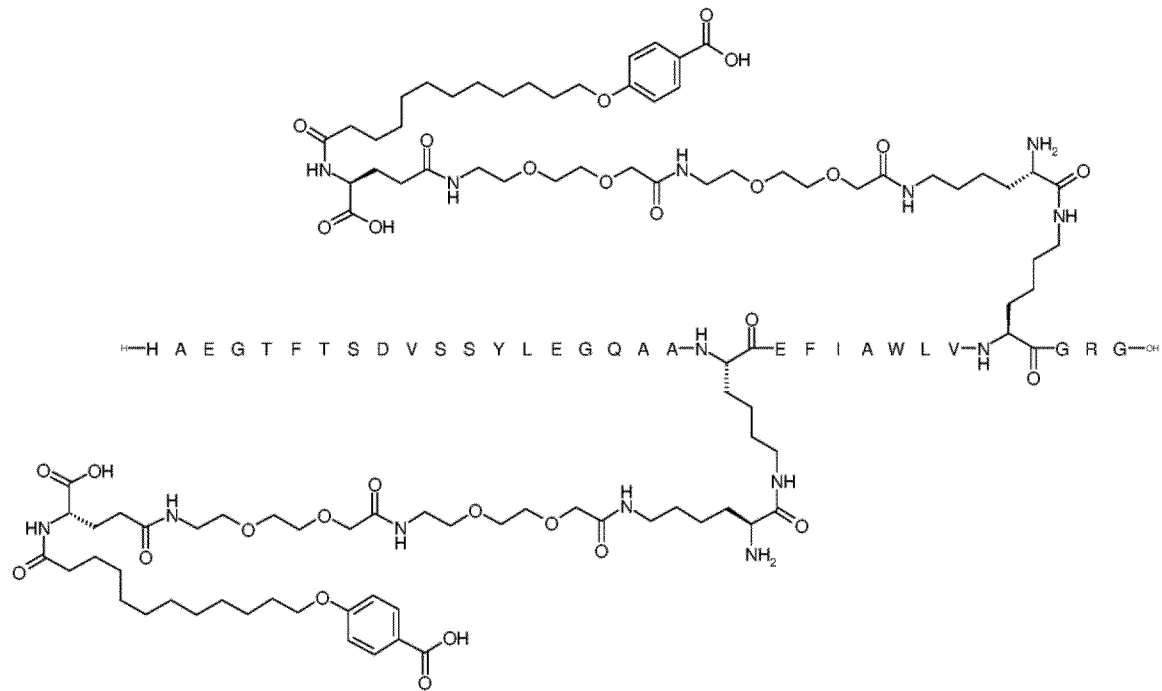

Signed and Sealed this
Fifteenth Day of November, 2022

Katherine Kelly Vidal
*Director of the United States Patent and Trademark Office*

CERTIFICATE OF CORRECTION (continued)
U.S. Pat. No. 11,274,135 B2

At Column 133-134, Claim number 10, please replace with the following formula:

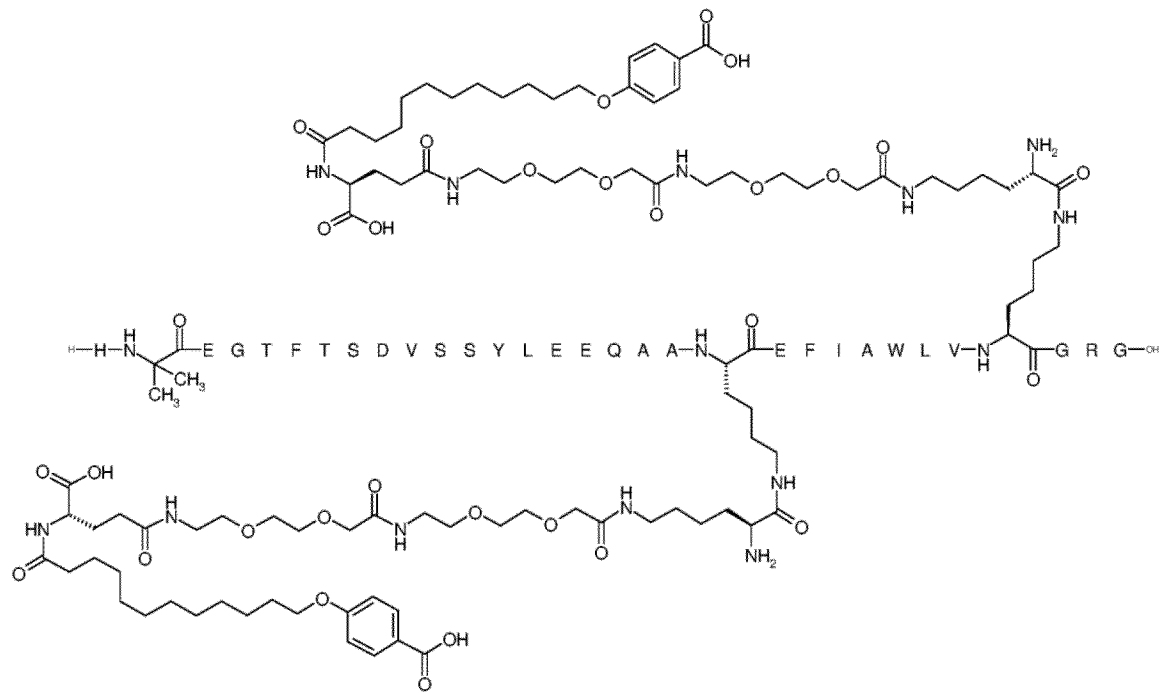

At Column 135-136, Claim number 11, please replace with the following formula: